(12) United States Patent
Gill et al.

(10) Patent No.: US 12,397,975 B2
(45) Date of Patent: Aug. 26, 2025

(54) MULTI-COMPONENT SAMPLE CONTAINER CAP

(71) Applicants: Sarvjit Gill, Loveland, CO (US); William J. Gillette, Loveland, CO (US); Keith Dirks, Loveland, CO (US); Casey Bollig, Rio, WI (US)

(72) Inventors: Sarvjit Gill, Loveland, CO (US); William J. Gillette, Loveland, CO (US); Keith Dirks, Loveland, CO (US); Casey Bollig, Rio, WI (US)

(73) Assignee: Gill, LLC, Fort Collins, CO (US)

( * ) Notice: Subject to any disclaimer, the term of this patent is extended or adjusted under 35 U.S.C. 154(b) by 236 days.

(21) Appl. No.: 17/984,723

(22) Filed: Nov. 10, 2022

(65) Prior Publication Data

US 2023/0061233 A1  Mar. 2, 2023

Related U.S. Application Data

(63) Continuation-in-part of application No. 17/160,366, filed on Jan. 27, 2021, now Pat. No. 11,761,946.

(51) Int. Cl.
*B65D 51/18* (2006.01)
*B65D 43/02* (2006.01)
(Continued)

(52) U.S. Cl.
CPC ......... *B65D 51/18* (2013.01); *B65D 43/0231* (2013.01); *B65D 47/00* (2013.01);
(Continued)

(58) Field of Classification Search
None
See application file for complete search history.

(56) References Cited

U.S. PATENT DOCUMENTS

| 3,855,997 A | 12/1974 | Sauer |
| 4,150,578 A | 4/1979 | Swartz |

(Continued)

FOREIGN PATENT DOCUMENTS

| EP | 487490 A2 * | 5/1992 | .......... B01L 3/50825 |
| EP | 0487490 B1 | 2/1995 | |

(Continued)

OTHER PUBLICATIONS

PCT; International Search Report dated Aug. 8, 2023 in Application No. PCT/US2023/017338.

(Continued)

*Primary Examiner* — Huy Q Phan
*Assistant Examiner* — Carl F. R. Tchatchouang
(74) *Attorney, Agent, or Firm* — SNELL & WILMER L.L.P.

(57) ABSTRACT

A sample container cap (or "cap") is configured to be used with a sample container for collecting fluids. The cap has a body and a shutter connected to the body. The cap has a (1) first, open position in which at least one body opening and at least one shutter opening are not aligned and the cap is configured so that fluid cannot readily pass therethrough, (2) second, open position in which the at least one body opening and the at least one shutter opening are aligned and the cap is configured so that fluid can pass therethrough, and (3) third, closed and locked position, in which the at least one shutter opening and the at least one body opening are not aligned and fluid cannot readily pass through the cap, and the cap is configured to not be moved to an open position.

20 Claims, 39 Drawing Sheets

(51) Int. Cl.
  *B65D 47/00*  (2006.01)
  *G01N 1/20*  (2006.01)
(52) U.S. Cl.
  CPC ... *G01N 1/2035* (2013.01); *B65D 2251/0018* (2013.01); *B65D 2251/0081* (2013.01); *G01N 2001/205* (2013.01)

(56) References Cited

U.S. PATENT DOCUMENTS

| | | |
|---|---|---|
| 8,393,487 B1 | 3/2013 | Pillers et al. |
| 2006/0115385 A1* | 6/2006 | Jon Meyer ......... A61B 10/0096 422/547 |
| 2010/0176080 A1 | 7/2010 | Grunert et al. |
| 2010/0291619 A1* | 11/2010 | Robinson ........... G01N 35/0099 435/288.7 |
| 2011/0098590 A1* | 4/2011 | Garbutt ................ A61B 5/0059 600/532 |
| 2013/0075398 A1* | 3/2013 | Morewitz, II ....... B65D 47/265 220/253 |
| 2013/0109009 A1* | 5/2013 | Kessel .................. B01L 3/5082 435/5 |
| 2014/0076937 A1 | 3/2014 | Cavalier |
| 2017/0102308 A1 | 4/2017 | Gillette et al. |
| 2017/0152080 A1* | 6/2017 | Zoppas ............... B65D 41/3428 |
| 2018/0037382 A1 | 2/2018 | Huss |
| 2019/0145658 A1 | 5/2019 | Hodgkinson et al. |
| 2019/0352059 A1 | 11/2019 | Mutch |
| 2021/0354889 A1 | 11/2021 | Wong et al. |
| 2023/0061233 A1 | 3/2023 | Gill et al. |

FOREIGN PATENT DOCUMENTS

| | | |
|---|---|---|
| EP | 0753741 A1 * | 1/1997 |
| EP | 2127750 A2 * | 12/2009 .......... B01L 3/50825 |
| KR | 200256569 Y1 | 12/2001 |

OTHER PUBLICATIONS

PCT; Written Opinion of the International Searching Authority dated Aug. 8, 2023 in Application No. PCT/US2023/017338.

IP Australia; Examination Report No. 1 dated May 18, 2023 for Application No. 2022203082.

United States Patent and Trademark Office, Non-Final Office Action Received in U.S. Appl. No. 17/711,645, dated Sep. 6, 2024.

* cited by examiner

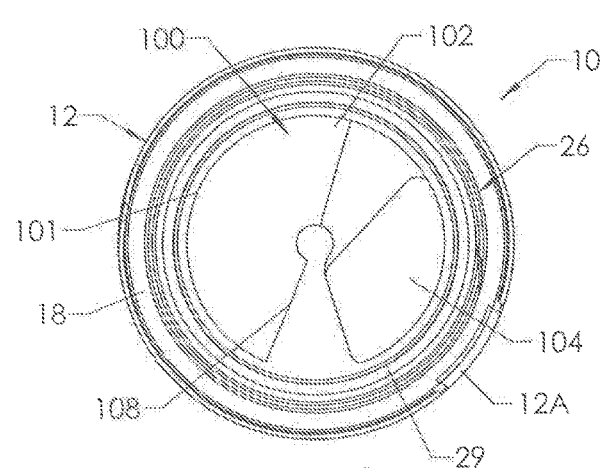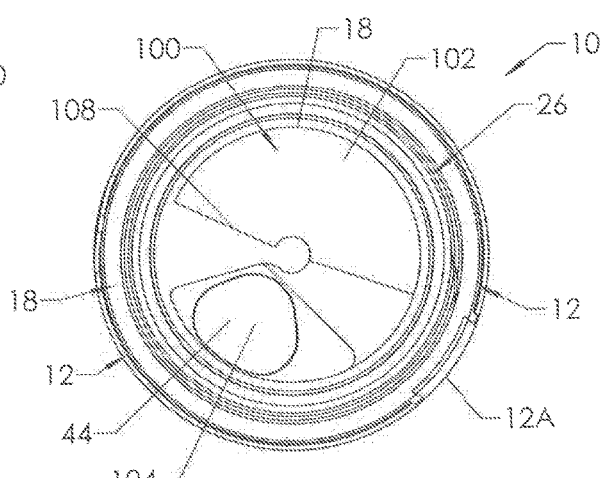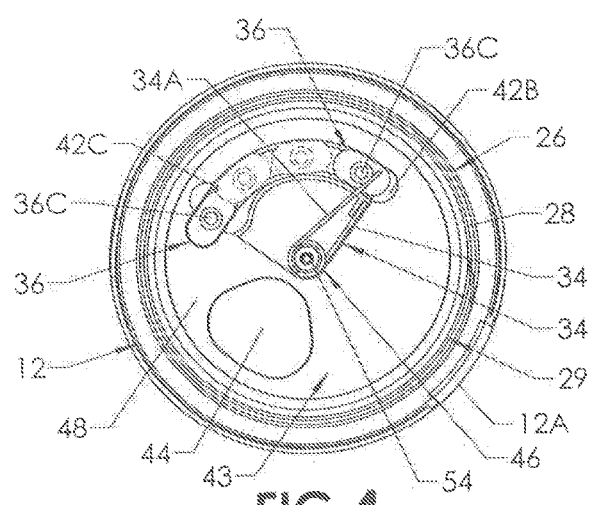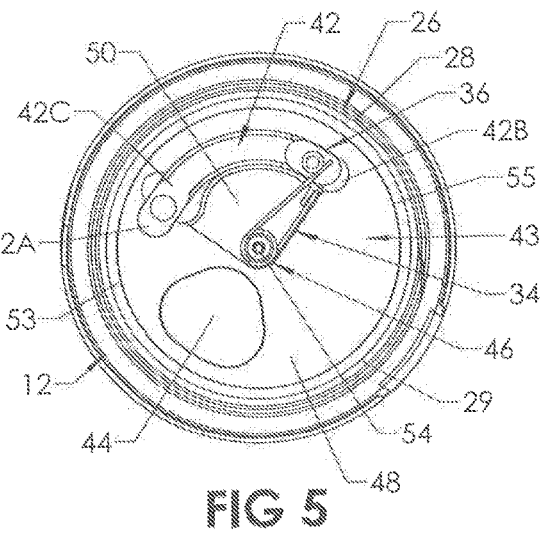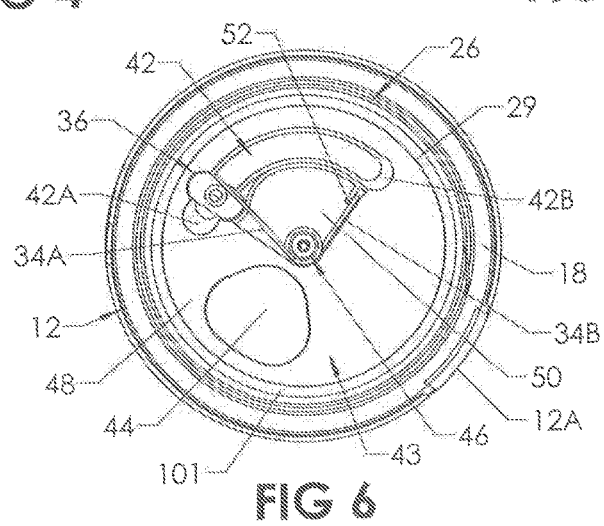

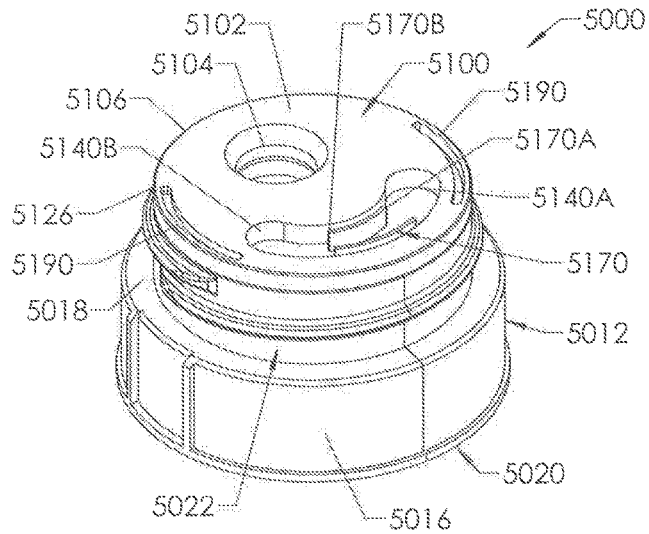
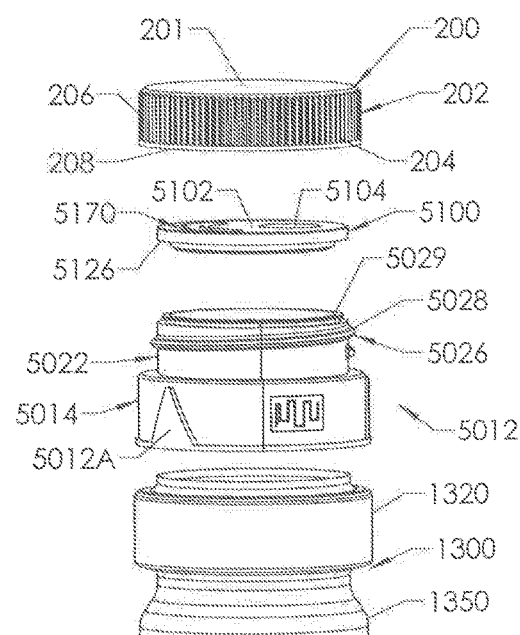
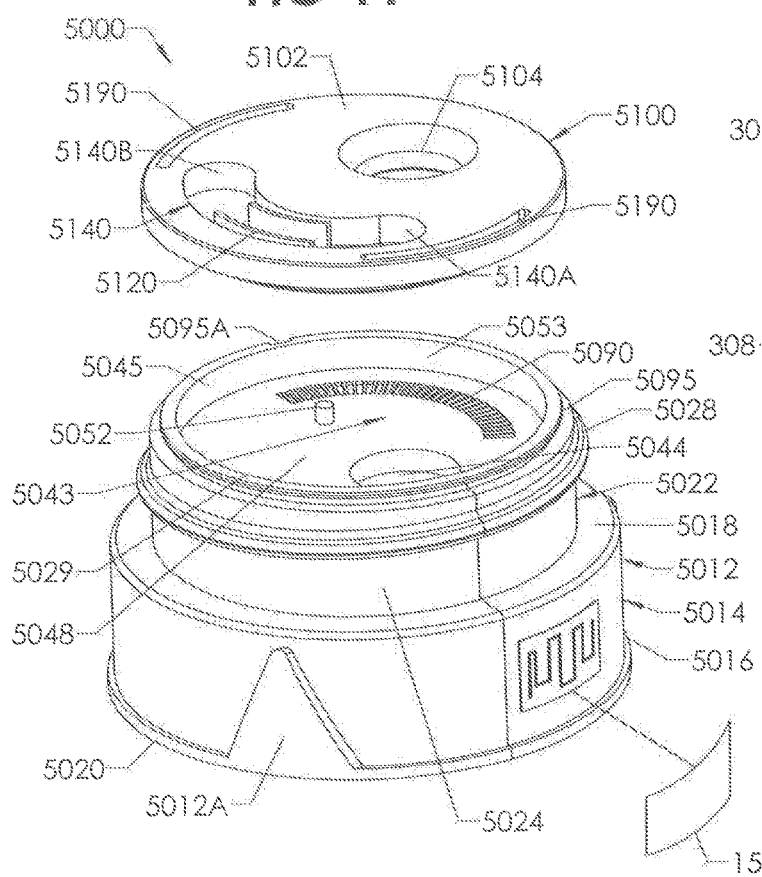
FIG 44
FIG 45
FIG 46

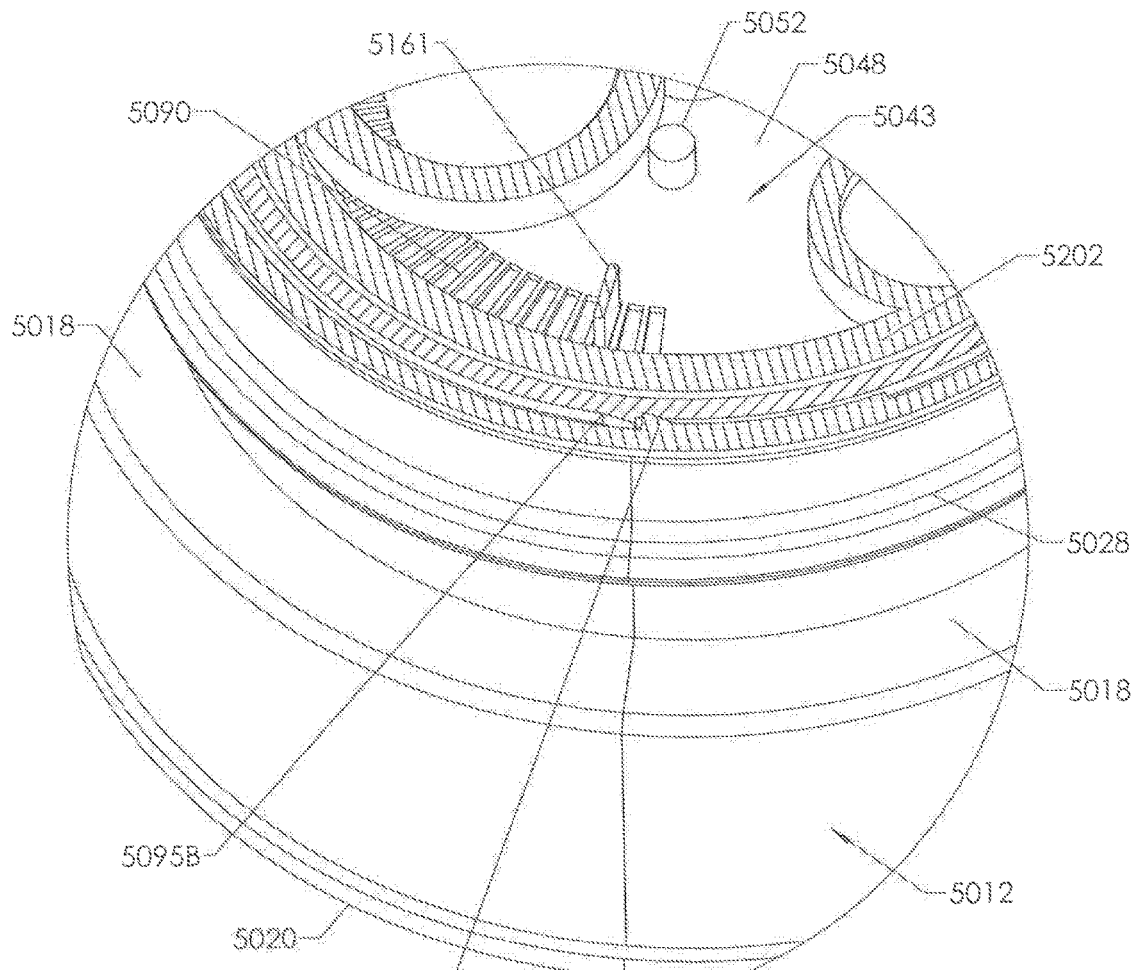
FIG 61
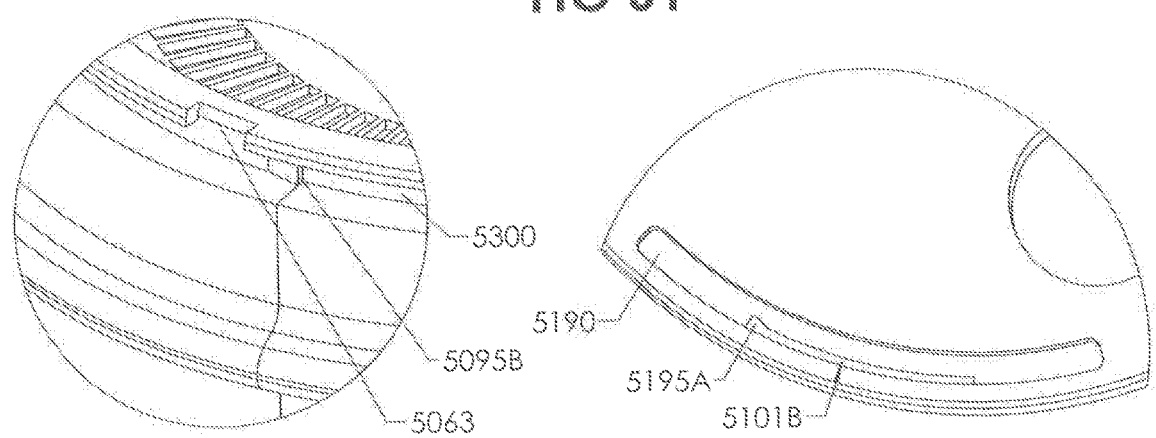
FIG 61A
FIG 61B

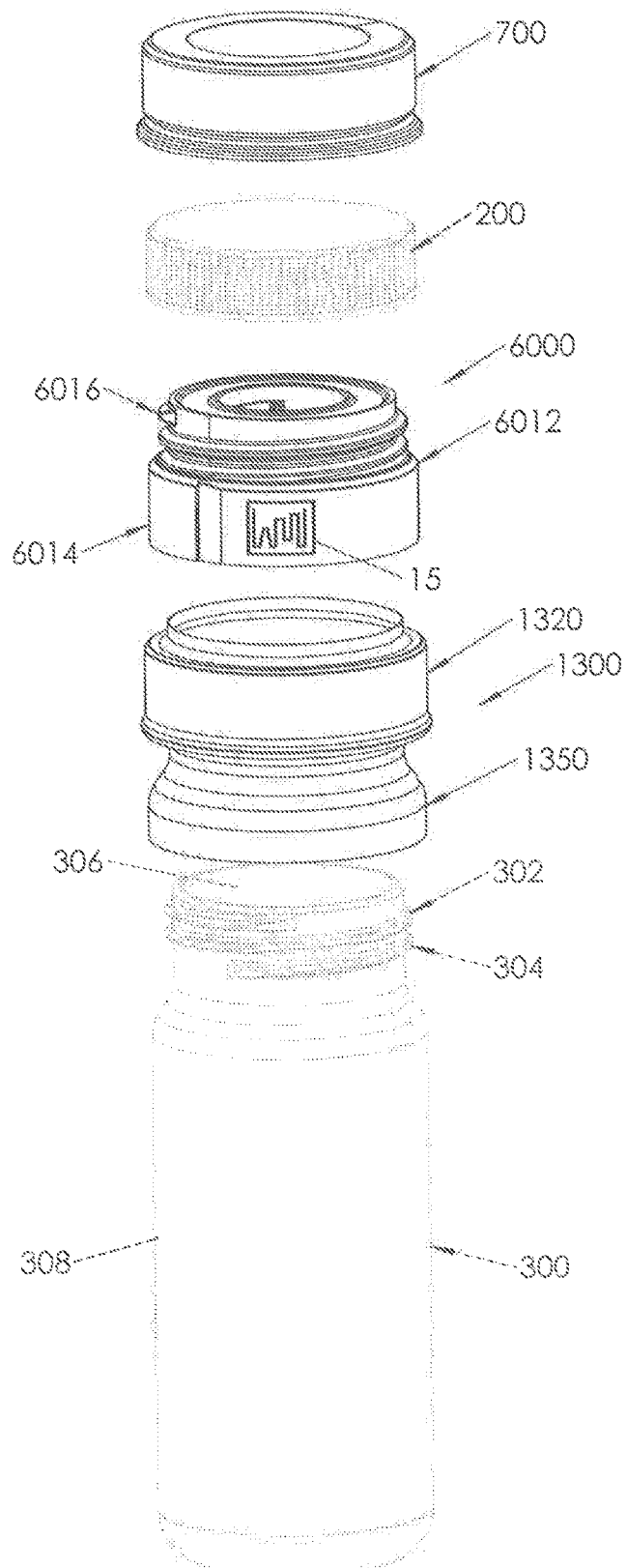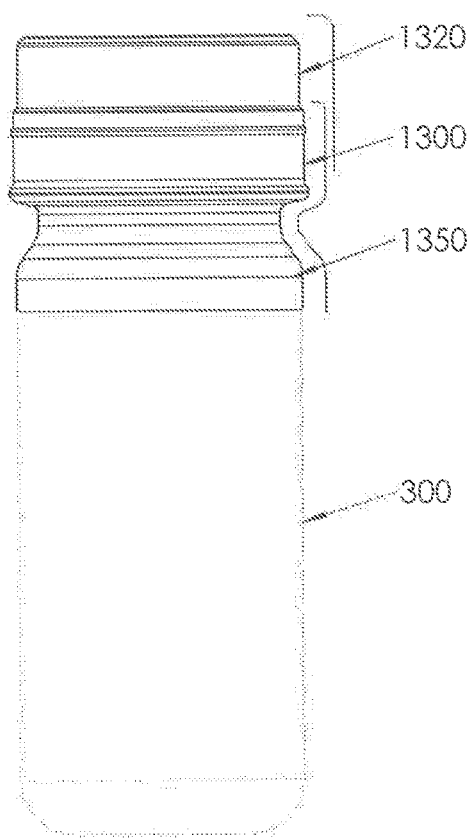
FIG. 82
FIG. 83

MULTI-COMPONENT SAMPLE CONTAINER CAP

CROSS REFERENCE TO RELATED APPLICATIONS

This application is a continuation-in-part of, and claims priority to U.S. patent application Ser. No. 17/160,366, filed on Jan. 27, 2021, now U.S. Pat. No. 11,761,946, and entitled "METHODS AND DEVICES FOR MONITORING MACHINE FLUIDS," the disclosure of which is incorporated herein by reference in its entirety.

BACKGROUND

As used herein, the term "fluid" refers to any fluid used in stationary and/or mobile machinery or electrical transformers such as, but not limited to, water, oil, grease, brake fluid, steering fluid, hydraulic fluid, coolant, air conditioning fluid, diesel fuel, gasoline, or cleaning fluid. Machinery (e.g., engines, compressors, gearboxes, grinding mills, pumps, transformers) use fluids for various reasons, such as to reduce the friction between moving mechanical components or heat transfer fluid. Ongoing maintenance and preventative care of machinery often requires gathering and analyzing fluid samples to determine their amount of physical and/or chemical degradation. Physical degradation can be as a result of, but not limited to, water contamination (e.g., free water, dissolved water, condensing moisture), dirt (e.g., dust, sand), wear metals (e.g., copper, tin, iron, lead, chrome), which may result from metal-to-metal surface frictional wear, soot (carbon), engine coolant (e.g., glycol, water) leakage or contamination, contamination by chemical constituents stemming from internal combustion process, or the heat and pressure inside of the machine. Chemical degradation can be result of, but not limited to, change in fluid viscosity, formation of varnish deposits, reduction in fluid additives (e.g., defoaming agents or antioxidants). As used herein, "fluid" also includes any other type of fluid that may be stored in a sample container to prevent or lessen the likelihood of contamination. Such fluids can be bodily fluids, such as blood, urine, or saliva, water, liquid food products such as milk or orange juice, cleaning fluids, fluids used in manufacturing facilities, fluids for intravenous use, pharmaceuticals, or others.

A problem with containers (also referred to herein as "sample container" or "fluid sample container") used to collect fluid samples is that the sample can be contaminated by outside dust or vapors present in the ambient environment during sample collection or after sample collection and prior to the sample being tested. Additionally, carelessness during the sample collection process may inadvertently introduce contamination into the container.

SUMMARY

A fluid sample container cap (or "cap") is configured to be used with a sample container for collecting a fluid sample to be tested. The cap includes (1) a bottom portion having (a) a bottom cavity configured to retain a sample container, such as a sample bottle, (b) an opening (sometimes referred to herein as a "bottom opening") configured to permit fluid to pass therethrough and into the sample container, and (2) a top portion connected to the bottom portion, wherein the top portion includes (a) an opening (sometimes referred to herein as a "top opening") configured to permit fluid to pass therethrough, through the bottom opening, and into the sample container. The bottom portion also preferably includes outer threads (or other connective structure) configured to mate with threads (or other connective structure) in a housing or other structure (such as a hand-operated extraction device or adapter) that is also configured to be attached to a machine that contains the fluid.

When the sample container cap is connected to the sample container a first tamper-proof structure or device may be added. The tamper-proof structure could be shrink-wrap plastic film covering at least part of the bottom portion of the sample container cap and at least part of the sample container. If the tamper-proof structure is removed or damaged that indicates that someone may have tampered with the fluid sample in the sample container prior to the sample being tested or analyzed. A second tamper-proof structure, such as shrink-wrap plastic, can also be added between the (1) top portion or bottom portion of the sample container cap, and (2) a top closure, which seals the cap before the cap is attached to a housing or other structure. If the second tamper-proof structure is used, it is removed and the top closure is removed, before attaching the sample container cap to the housing or other structure.

The sample container cap has at least: (1) a first position (or closed position) in which the bottom opening and the top opening are not aligned, and (2) a second (or open) position in which the top opening and bottom opening are aligned. When in the second, aligned position, the cap is configured so that fluid can pass from the housing or other structure through the aligned top opening and bottom opening and into the sample container. Being "aligned" means that the bottom opening and top opening are sufficiently aligned to permit fluid to pass through the two and into a sample container. The bottom opening and top opening need not be perfectly aligned. After the fluid sample is collected, the sample container cap can then be moved to a position (either the first (closed) position or a third (closed) position) at which the top opening and bottom opening do not align and the fluid is sealed in the sample container. When the cap is moved from the open to the closed (either the first or the third) position, the sample container cap is preferably locked, which prevents the cap to be moved back to the open position, wherein fluid could leak out of the container or the fluid could be contaminated by outside dust or vapors present in the ambient environment. When in the sealed position fluid likely cannot leak from, and contaminants are unlikely to pass from the outside and into, the sample container.

In another embodiment, the cap comprises a body and a shutter. The body has one or more body openings and the shutter has one or more shutter openings. When the body and the shutter are first connected the cap is in a first, closed position in which the one or more body openings do not align with the one or more shutter openings and fluid cannot readily pass through the cap. The cap is connected to a container in the manner previously described, preferably with a tamper-proof (or security) structure(s) and a top closure added.

To attach the cap to a mounting structure of a fluid-dispensing device (such as a housing or hand pump), the top portion of the security structure is removed and the top closure is removed from the cap. Then the cap is threaded onto the mounting structure of the fluid-dispensing device. As it is threaded the cap moves upwards until a first stem extending from the mounting structure engages a first flange of the shutter that extends through a body opening of the cap body and a second first stem extending from the mounting structure engages a second flange of the shutter that extends through a body opening of the cap body. Only one flange and stem, or more than two flanges and stems, however, may be utilized.

The engagement of the one or more stems with the one or more flanges prevents the shutter from rotating and the body continues to rotate and move upwards until the cap is fully tightened on the mounting structure. As the body rotates until it is fully tightened while the shutter remains stationary, the cap moves from its first, closed position to a second, open position in which the one or more shutter openings align with the one or more body openings and permit the passage of fluid through the cap and into the container.

Once a fluid sample is collected inside of the container, the cap is unscrewed from the mounting structure, which causes the cap to move from the second, open position to a third, closed and locked position. As the cap is unscrewed the first flange moves away from the first stem and contacts a third stem that is in the mounting structure and adjacent the first stem, and the second flange moves away from the second stem and contacts a fourth stem that is in the mounting structure and adjacent the second stem. The engagement of the one or more flanges with the third stem and the fourth stem prevents the shutter from rotating farther in the opening (or loosening) direction.

In the third, closed and locked position (1) a side of a first body opening through which the first flange extends contacts the first flange, and (2) a side of a second body opening through which the second flange extends contacts the second flange. This causes the body and shutter to rotate together in the loosening direction. Also, the respective flanges moved from the first stem to the third stem and the second stem to the fourth stem, the one or more openings in the shutter moved and are no longer aligned with the one or more openings in the body, but are instead aligned with solid walls in the body, so fluid cannot readily pass through the cap, and the cap is in a closed position.

Additionally, as the respective shutter flanges moved from the first stem to the third stem and the second stem to the fourth stem, one or more projections on an outer edge of the shutter move past one or more abutment protrusions inside of the body, and the respective shapes of the one or more protrusions and the one or more projections prevent movement of the body relative the shutter in the tightening direction. Hence, the cap is in the third, closed and locked position, because fluid cannot readily pass through the cap, and the shutter and body cannot move (in any significant amount) relative each other in either the tightening direction or the loosening direction.

The cap, with the sample container attached, can then be unscrewed from the mounting structure and removed from the housing, hand pump or other fluid-dispensing device, and the top closure is preferably re-attached to the top of the cap. The container, cap, and top closure are sent to a laboratory or other facility for testing the fluid sample in the container. There, the second security structure is removed and the cap is unscrewed from the container to access the fluid inside.

BRIEF DESCRIPTION OF THE DRAWINGS

FIG. 2 is a top view of the sample container cap of FIG. 1.

FIG. 3 is an alternate top view of the sample container cap of FIG. 2.

FIG. 4 is a top view of the bottom portion of the sample container cap of FIG. 1 showing a cam in alternate positions in a channel.

FIG. 5 is an alternate top view of the bottom portion of the sample container cap of FIG. 4.

FIG. 6 is an alternate top view of the bottom portion of the sample container cap of FIG. 4.

FIG. 44 is a side, perspective view of an alternate sample container cap.

FIG. 45 is a partially-exploded perspective, side view of the sample container cap of FIG. 44.

FIG. 46 is a side, perspective view of the sample container cap of FIG. 44 showing a sample container, an embodiment of a security structure, and a top closure.

FIG. 61 is an enlarged view of the structure designated as M in FIG. 60.

FIG. 61A is an enlarged, partial, side, perspective view of a top edge of the bottom portion of the cap of FIG. 44.

FIG. 61B is an enlarged, partial, top view of the top surface of the top portion of the cap of FIG. 44.

FIG. 82 is an exploded view of a device having an alternate sample container cap according to this disclosure in combination with a sample container shown in phantom, a top closure shown in phantom, a security structure, and a mounting structure.

FIG. 83 is an assembled, side view of the device of FIG. 82.

FIG. 116 is a side view of the adapter closure of FIG. 114.

FIG. 117 is a bottom view of the adapter closure of FIG. 114.

DETAILED DESCRIPTION

Figure 80:
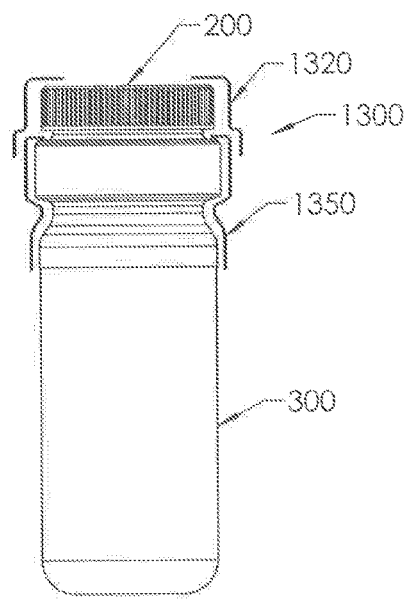
FIG. 80 is a side view of the sample container cap of any one of FIGS. 1, 17, and 44 attached to a sample container and a top closure, and including security structures.
Figure 81:
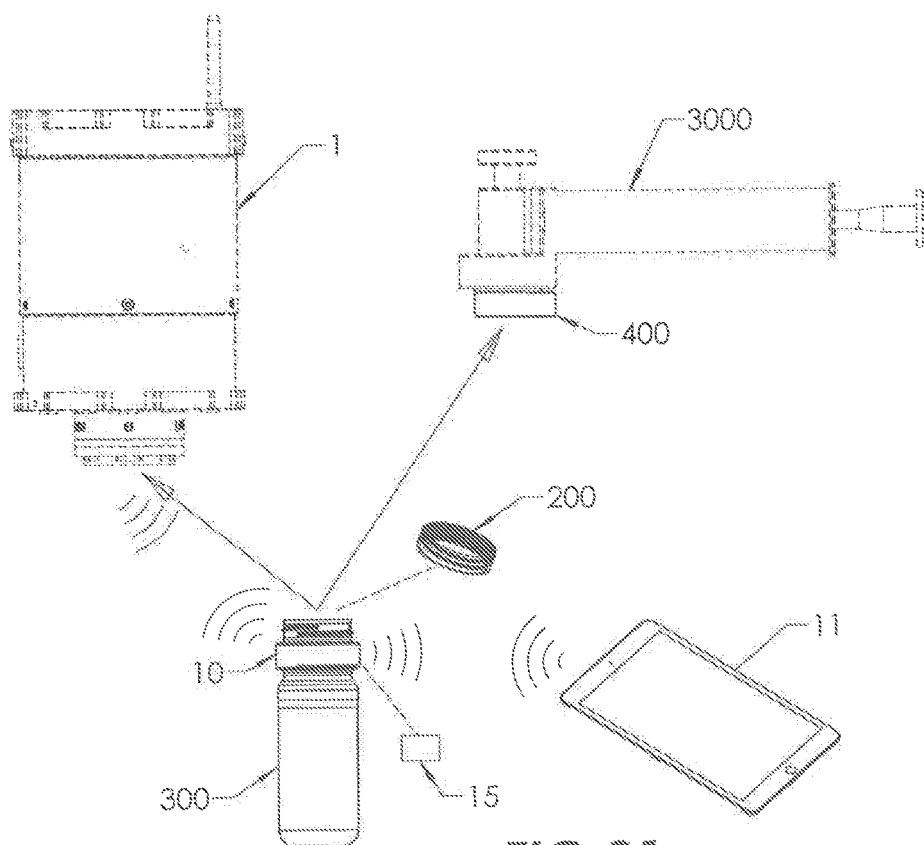
FIG. 81 is an exploded view of a system embodiment including a sample container cap and illustrating possible communications between components.
Figure 84:
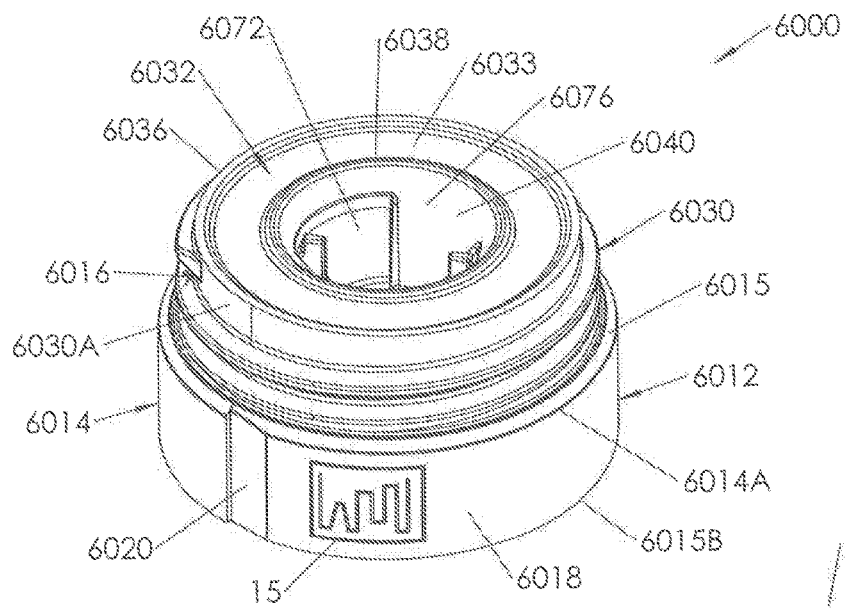
FIG. 84 is a top, perspective view of the sample container cap shown in FIG. 82.
Figure 85:
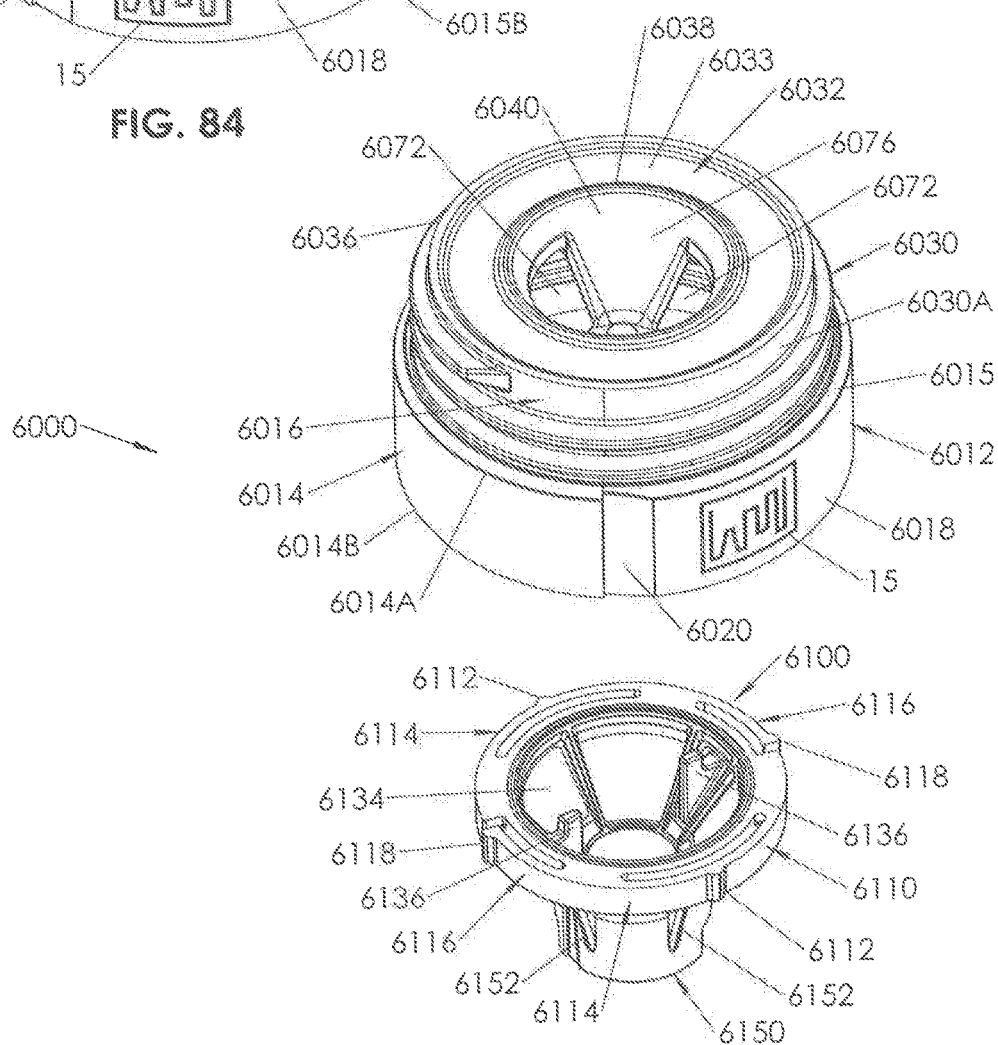
FIG. 85 is a top, perspective, exploded view of the sample container cap of FIG. 84.
Figure 86:
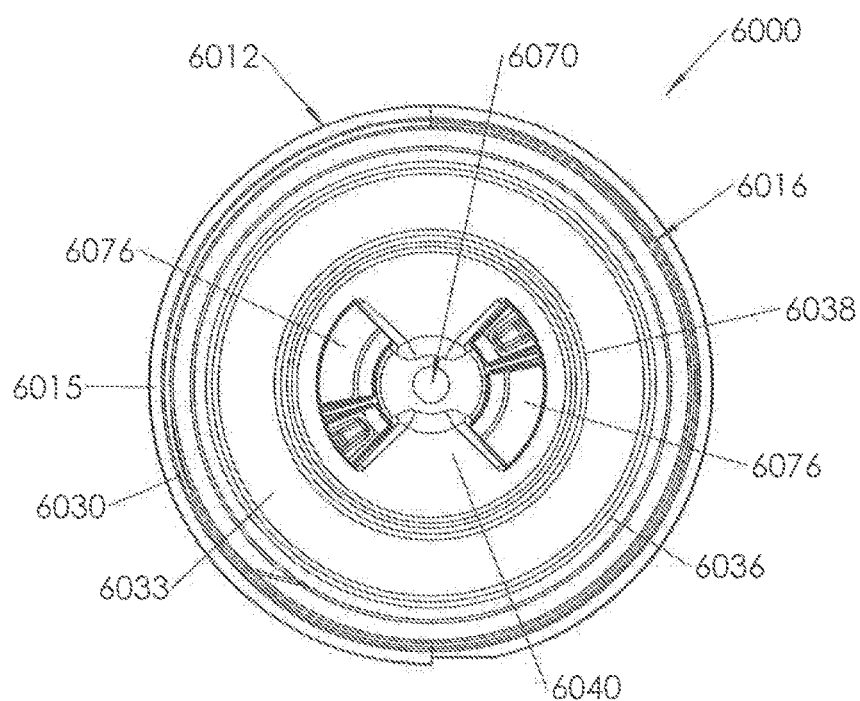
FIG. 86 is a top view of the sample container cap of FIG. 84 in a first, closed position.
Figure 87:
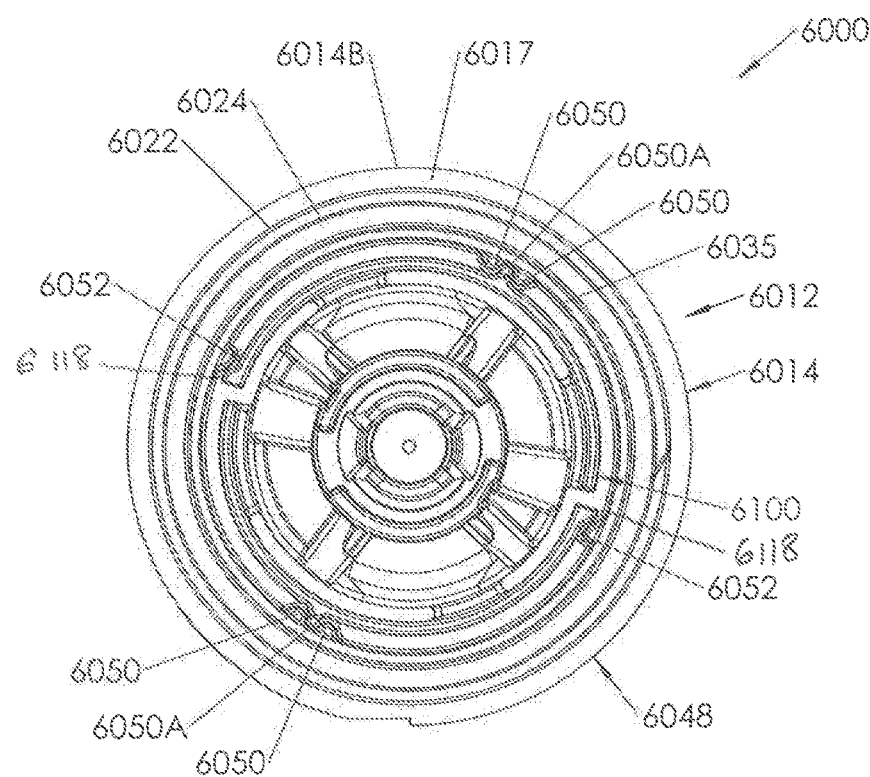
FIG. 87 is a bottom view of the sample container cap of FIG. 86.
Figure 88:
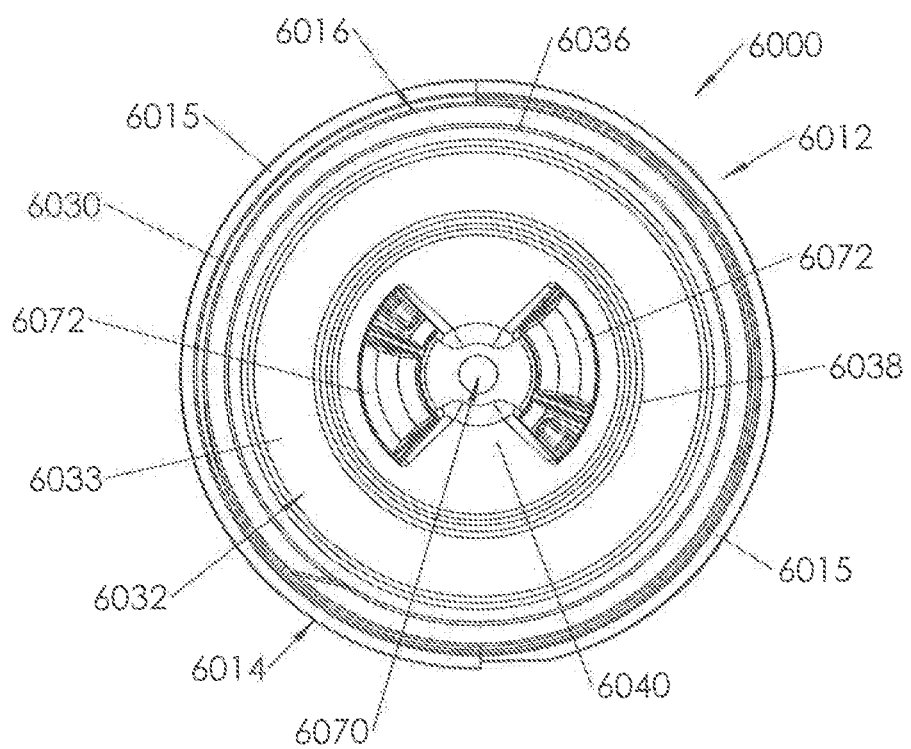
FIG. 88 is a top view of the sample container cap of FIG. 84 in a second, open position.
Figure 89:
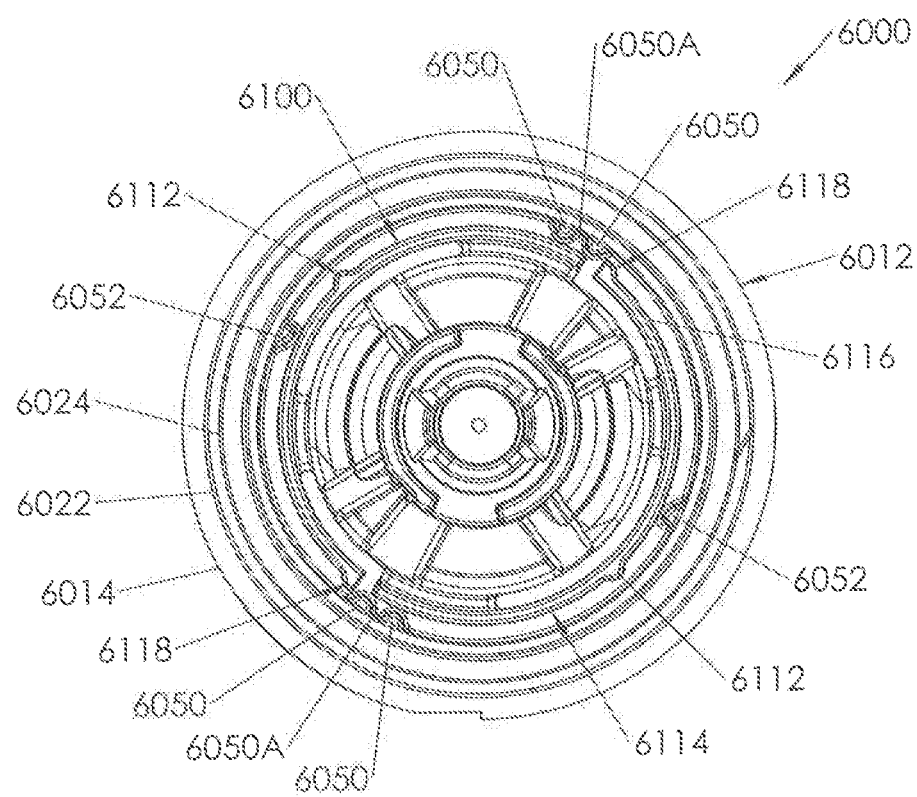
FIG. 89 is a bottom view of the sample container cap of FIG. 88.
Figure 90:
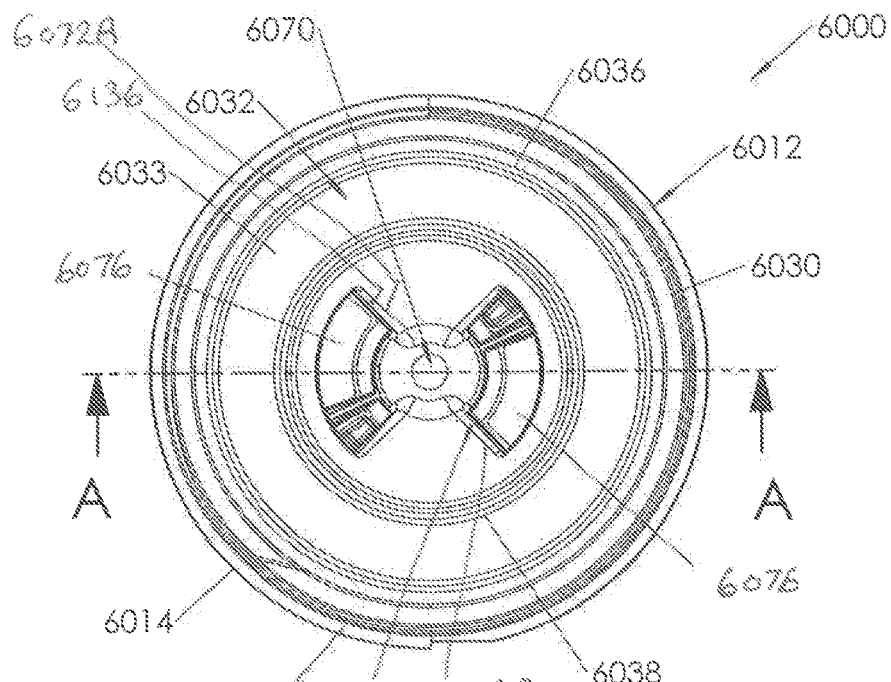
FIG. 90 is a top view of the sample container cap of FIG. 84 in a third, closed and locked position.
Figure 91:
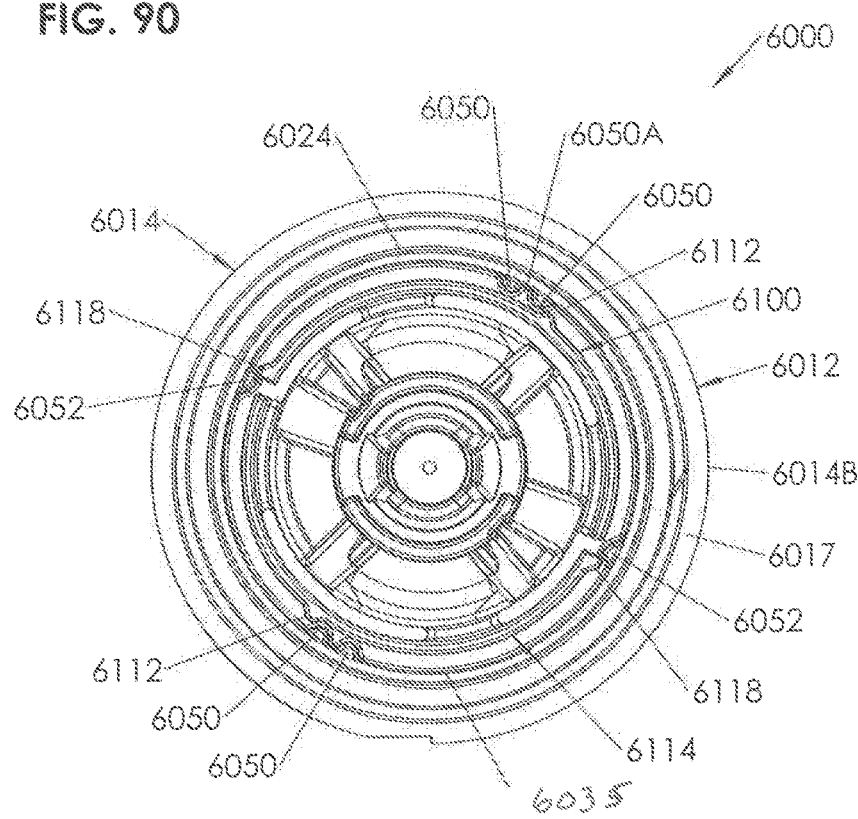
FIG. 91 is a bottom view of the sample container cap of FIG. 90.
Figure 92:
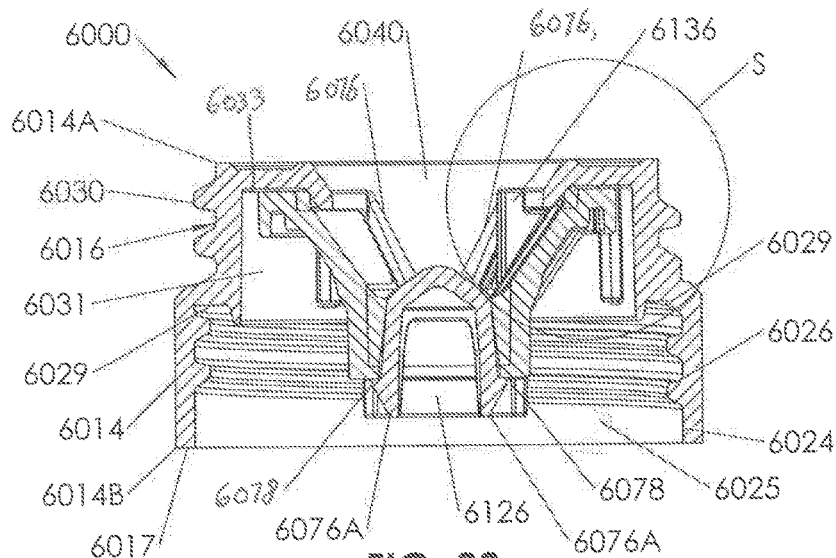
FIG. 92 is a side, cross-sectional view of the sample container cap of FIG. 90 taken through line A-A.
Figure 93:
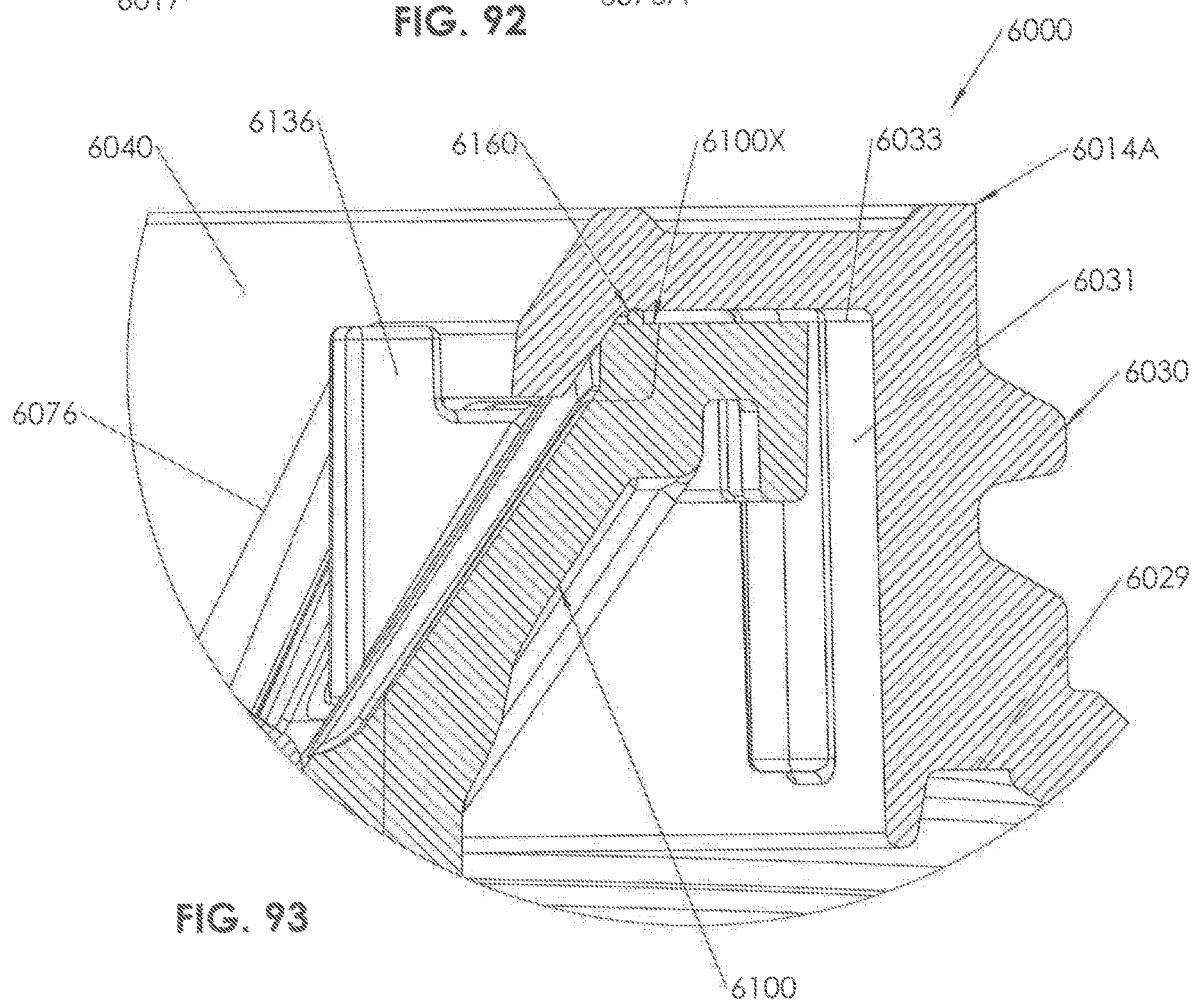
FIG. 93 is a closeup, side, cross-sectional view of Section S of FIG. 92.
Figure 94:
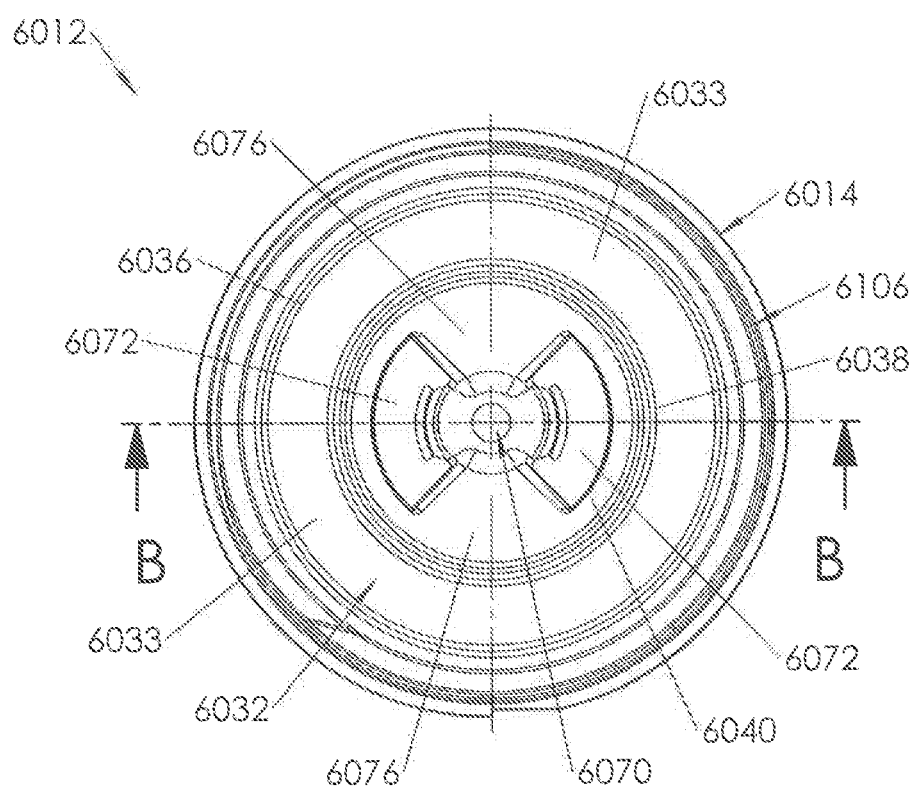
FIG. 94 is a top view of a cap body according to this disclosure.
Figure 95:
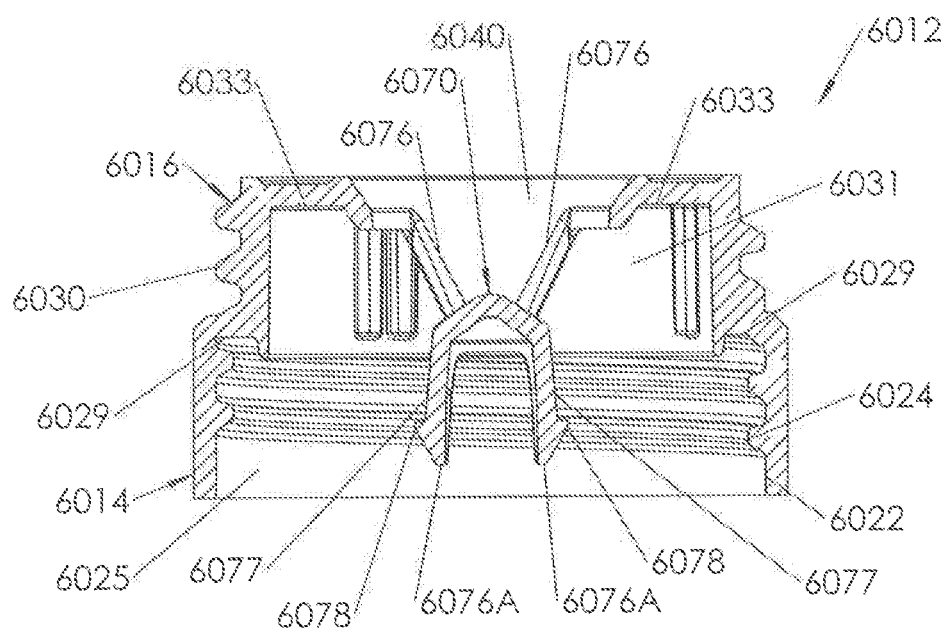
FIG. 95 is a side, cross-sectional view of the cap body of FIG. 94 taken through line B-B.
Figure 96:
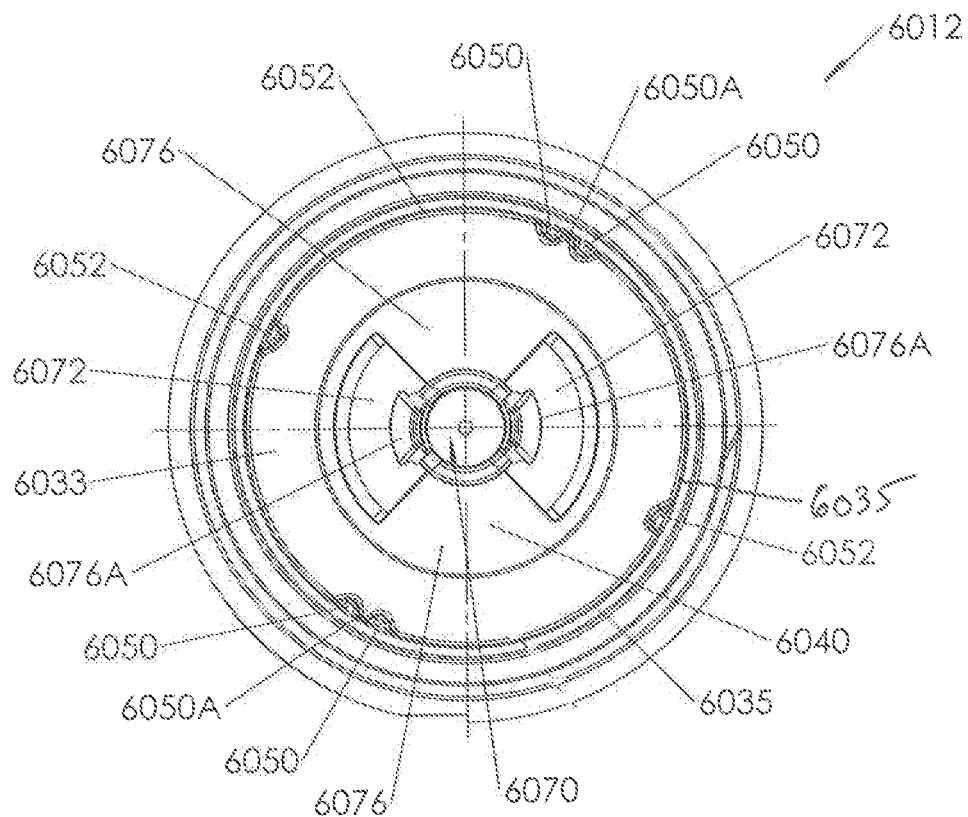
FIG. 96 is a bottom view of the cap body of FIG. 94.
Figure 97:
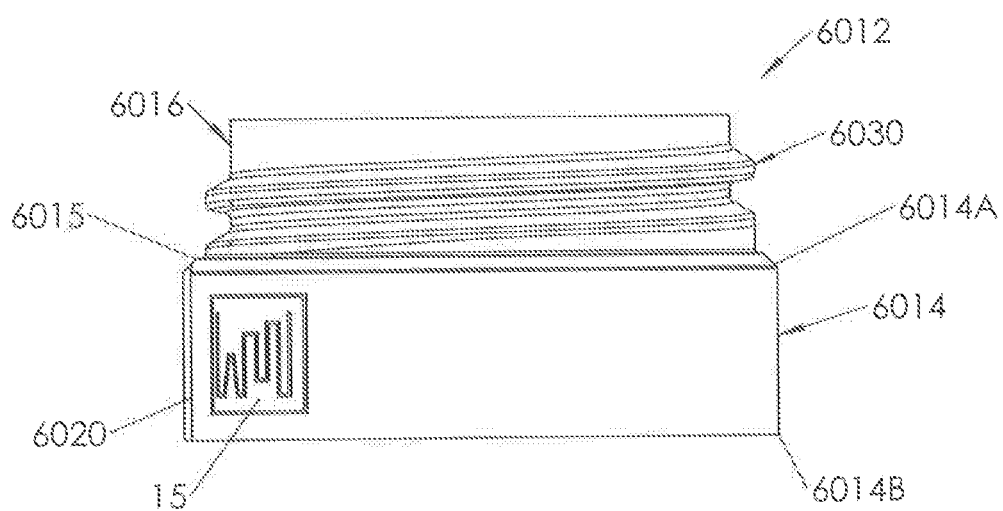
FIG. 97 is a side view of the cap body of FIG. 94.
Figure 98:
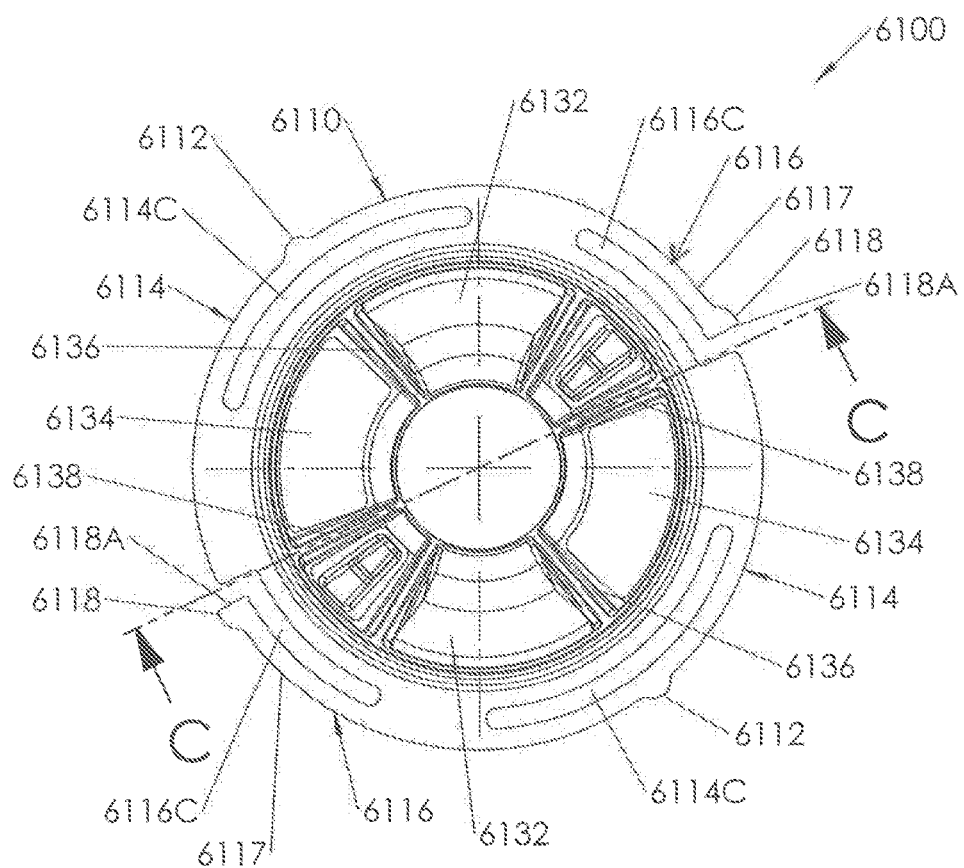
FIG. 98 is a top view of the shutter of the cap of FIG. 84.
Figure 99:
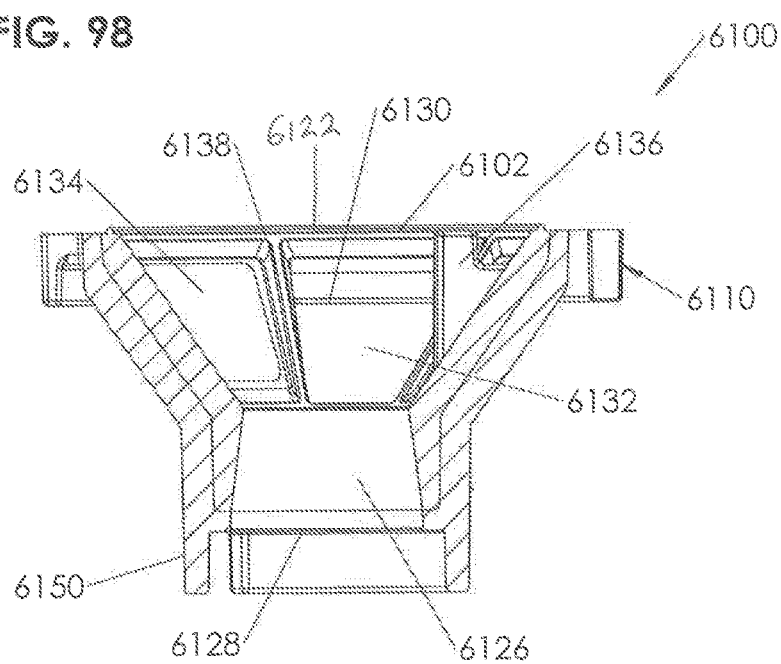
FIG. 99 is a side, cross-sectional view of the shutter of FIG. 98 taken through line C-C.

Turning now to the Figures, wherein the purpose is to describe embodiments of this disclosure and not to limit the scope of the claims, (1) FIGS. 1-16 show an Embodiment 1 of a sample container cap 10, (2) FIGS. 17-43 show an Embodiment 2 of a sample container cap 1000, (3) FIGS. 44-73 show an Embodiment 3 of a sample container cap 5000, (4) FIGS. 74-79 show an adapter 400 that can be used with a sample container cap 10, 1000, or 5000, (4) FIG. 80 shows one or more security structures that may be used with sample container cap 10, 1000, or 5000, and (5) FIG. 81 shows possible communications between components of a system embodiment.

In the embodiments described, the respective caps can move from either a first, closed position (also referred to herein as the "first position") to a second, open position (also referred to herein as the "second position"), and back to a closed position, which is referred to herein as the third, closed position (also referred to herein as the "third position"). The third, closed position may be the same as the first, closed position or a different closed position. Further, each of the respective caps may first be in an open position when first assembled and then be moved to a closed position.

The structure on a top portion of either cap 10, cap 1000, or cap 5000 configured to connect to a bottom portion of either cap 10, cap 1000, or cap 5000, is sometimes referred to herein as a top connective structure. The structure on a bottom portion of either cap 10, cap 1000, or cap 5000 configured to connect to a top portion of either cap 10, cap 1000, or cap 5000, is sometimes referred to herein as a bottom connective structure.

Embodiment 1

Turning to FIGS. 1-16, fluid sample container cap 10 has a bottom portion 12 and top portion 100. Cap 10 is preferably configured to be attached to a sample container 300, and to a top closure 200. One or more security structures 1300, such as structure 1320 and structure 1350 (shown, for example, in FIGS. 1 and 80), may be utilized to secure top closure 200 to cap 10 and/or secure container 300 to cap 10. Security structure 1320 and security structure 1350 may be shrink-wrap plastic.

Bottom portion 12 has a lower section 14 with an outer annular wall 16, an upper ledge 18, and a lower edge 20. Bottom portion 12 further includes an upper section 22 that has an outer diameter that is less than the outer diameter of lower section 14. Upper section 22 further comprises an annular outer wall 24, with a threaded top 26 that includes one or more outer threads 28 that are configured to be received in a housing (such as housing 1 shown in FIGS. 38, 40, 42, 68, 70, and 72) or an adapter (such as adapter 400 shown in FIGS. 74-79), or other structure. One or more threads 28 are also configured to receive top closure 200: (1) before cap 10 is attached to a housing, adapter, or other structure, and (2) after a fluid sample is received in a container 300 and the cap 10 is moved from its open to a closed position, as explained further herein, and removed from the housing, adapter, or other structure. Upper section 22 further includes an upper lip 29.

Figure 1:
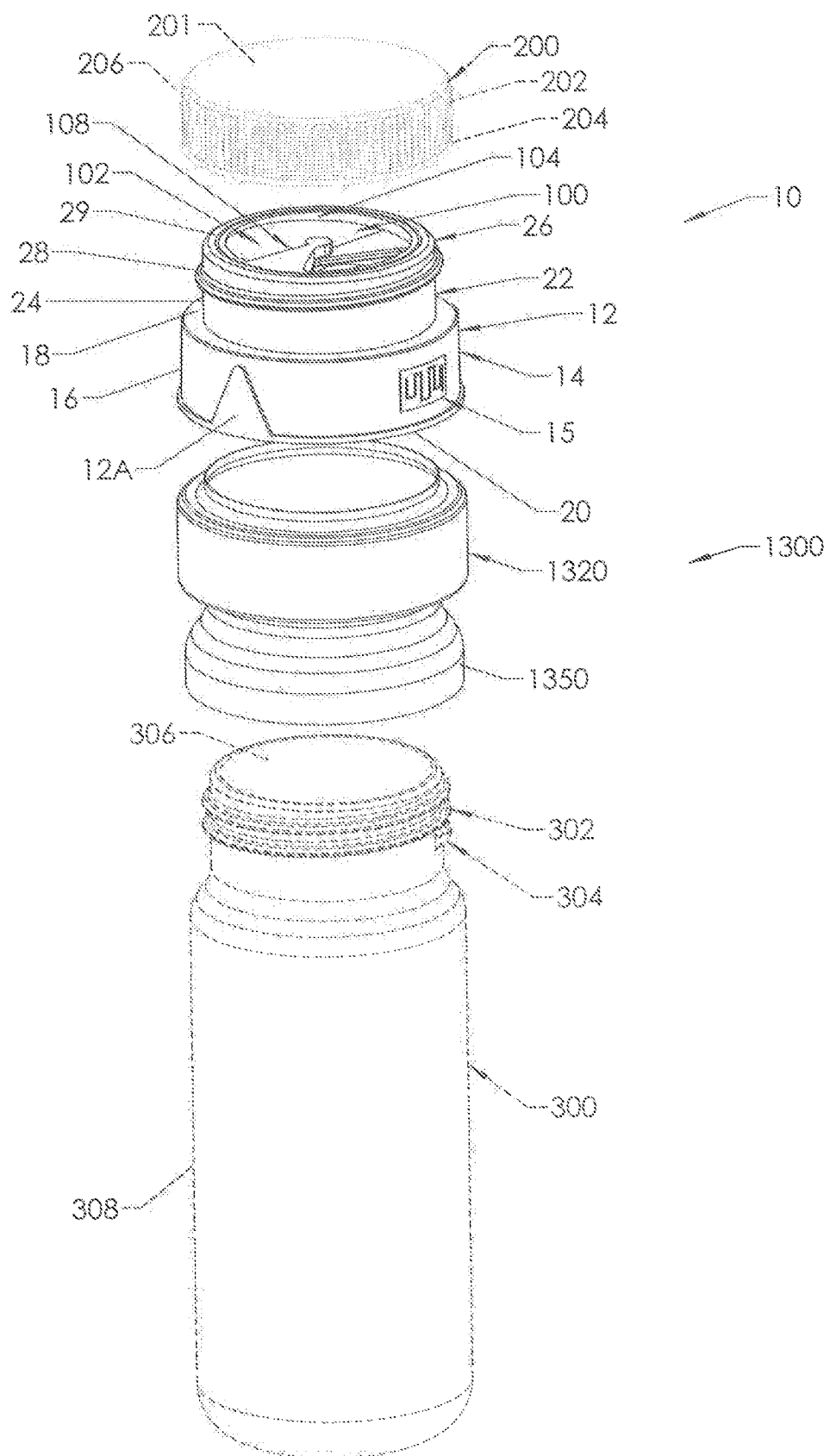
FIG. 1 is a side perspective, exploded view of a sample container cap according to an embodiment of this disclosure with a sample container and top closure shown in phantom and showing an embodiment of a security structure.
Figure 10:
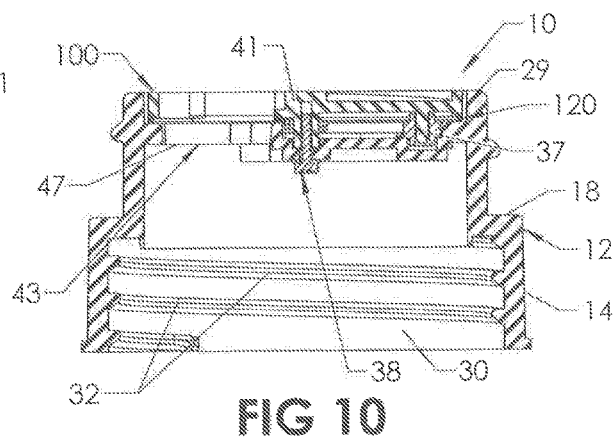
FIG. 10 is a cross-sectional, side view of the sample container cap of FIG. 9 taken through line A-A.
Figure 8:
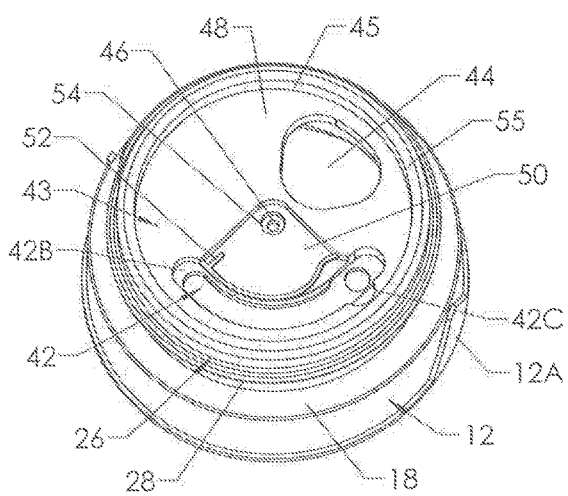
FIG. 8 is a bottom, perspective view of the bottom portion of the sample container cap of FIG. 1.
Figure 14:
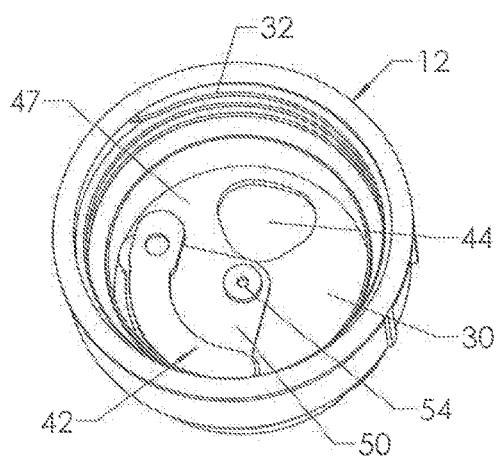
FIG. 14 is a bottom perspective view of the bottom portion of the sample container cap of FIG. 1.

As shown in FIGS. 10 and 14, bottom portion 12 has a lower cavity 30 that includes one or more threads 32, which are configured to receive one or more threads 302, shown, for example, on FIG. 1, of sample container 300 in order to connect sample container 300 to cap 10. One or more threads 32 are of any suitable configuration to mate with the one or more threads 302 on container 300, which may vary in structure based on the type of container. Bottom portion 12 also includes a plate 43 having a top surface 48, and an inside bottom surface 47 that helps define lower cavity 30 and that includes the bottom of depression 50 and of channel 42.

Bottom portion 12 further includes a bottom opening (or "opening") 44 in plate 43, wherein bottom opening 44 is configured to permit the passage of fluid through bottom portion 12 and into a container, such as sample container 300.

As shown, for example, in FIGS. 4-6, bottom portion 12 includes a channel 42 in top surface 48 (with the channel bottom is in lower cavity 30), wherein the channel has a first end 42A, a second end 42B, and a locking section 42C. Channel 42 has a first side 42A, a second side 42B, and a locking section 42C.

Referring to FIGS. 2-3, 7, 10, 11, and 15, top portion 100 is positioned in an upper cavity 45 of bottom portion 12, wherein upper cavity 45 has an annular side wall 53. Top portion 100 has an upper, annular lip 101 and a top surface 102. Turning to FIGS. 2, 3, 10, and 15, top portion 100 further includes an inner annular wall 103, an opening 104 that is configured for the passage of fluid therethrough, and a leg 108 that is raised from top surface 102, wherein leg 108 is configured to engage a fluid sample tube as explained herein.

Figure 7:
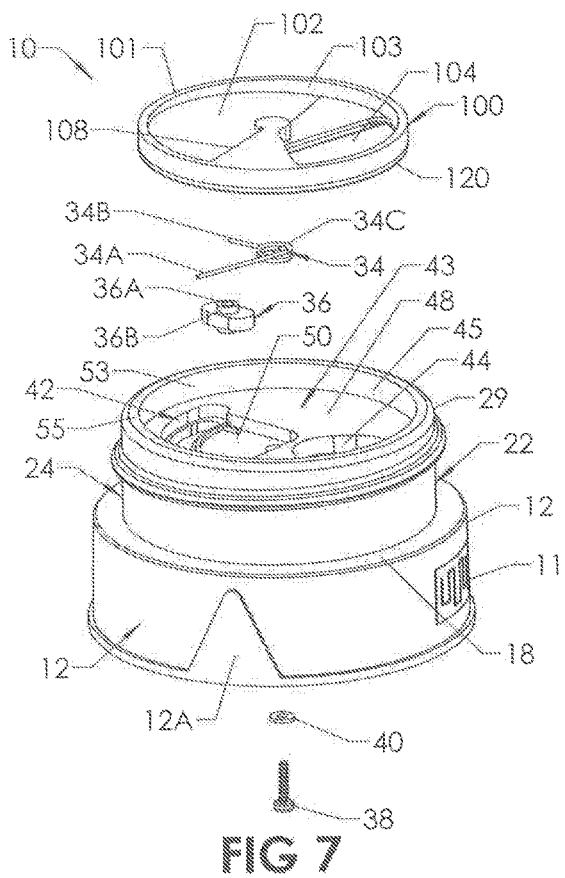
FIG. 7 is a partially-exploded, side perspective view of the sample container cap of FIG. 1.
Figure 9:
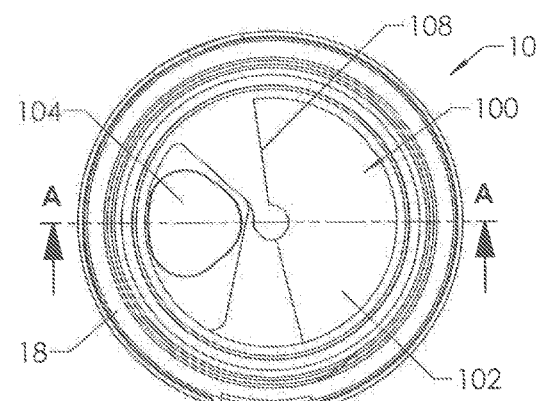
FIG. 9 is an alternate top view of the sample container cap of FIG. 1.

FIG. 7 shows an exploded view of cap 10 and FIG. 10 shows a cross-sectional side view of cap 10. FIG. 7 illustrates a spring 34, cam (sometimes referred to as a protrusion or projection) 36 that is positioned in the channel, screw 38, and washer 40.

Spring 34 has a first leg 34A, a second leg 34B, and an aperture 34C. Stem 41, shown in FIGS. 10 and 15, on the bottom surface 115 of top portion 100 extends through opening 34C to assist in positioning spring 34. As shown in FIG. 7, spring 34 is in its relaxed position, and as shown in FIGS. 4 and 5 spring 34 is in its compressed position. Opening 34C, best shown in FIG. 7, fits over an aperture 54 (which receives screw 38) in the top surface 48 of plate 43 of bottom portion 12, as best shown in FIGS. 4-6. Spring 34 preferably rests in depression 50 in which spring arm 34B is retained by a leg 52.

Cam 36 has a neck 36B and aperture 36C. A stem 37, shown in FIGS. 10 and 15, which extends downward from a bottom surface 115 of top portion 100, is positioned in opening 36A to retain cam 36 on stem 37, and ultimately to position cam 36 in channel 42. Cam 36 is free to rotate around stem 37 and channel 42 can move around cam 36 in response to the movement, such as rotation, of bottom portion 12.

Screw 38 connects bottom portion 12 to top portion 100. Screw 38 passes through aperture 54 in plate 43 and screw 38 threads into an aperture in stem 41, which can be seen in cross-section in FIG. 10. Because screw 38 is not threaded into bottom portion 12 and screw 38 is only tightened into stem 41 of top portion 100 a sufficient amount to create a seal between bottom portion 12 and top portion 100, top portion 100 can rotate independently of bottom portion 12 and vice versa.

FIG. 2 shows cap 10 in a first, closed position. In this position opening 104 of top portion 100 and opening 44 of bottom portion 12 are not aligned and cap 10 is configured so that fluid cannot pass therethrough and into sample container 300. FIG. 3 shows cap 10 in a second, open position. In this position top opening 104 and bottom opening 44 are aligned (although they need not be perfectly aligned) and cap 10 is configured so that fluid can pass therethrough and into sample container 300.

Turning now to FIGS. 4-6, FIG. 4 shows the travel of channel 42 around cam 36. When cap 10 is in its first, closed position, cam 36 is in end 42A. as cap 1 is rotated and top portion 100 is held stationary, channel 42 moves around cam 36 until cam 36 is at an end 42B at which point top opening 104 and bottom opening 44 align and cap 10 is in its second, open position. In this position, cam 36 is biased towards end 42A by spring 34. When cap 10 is removed and top portion 100 is no longer held in a stationary position, channel 42 moves around cam 36 until cam 36 moves back to end 42A, as shown in FIG. 6, moves into locking section 42C. the operation of cap 10 is further defined below.

A security structure 1350 can be attached to cap 10 and sample container 300. Such a security structure 1350 might be shrink-wrap plastic film that is positioned on at least part of the cap 10 and at least part of the container 300. If the security structure is removed, torn, damaged, or broken that would indicate the possibility that someone had tampered with the sample in the sample container 300.

Gasket

Figure 15:
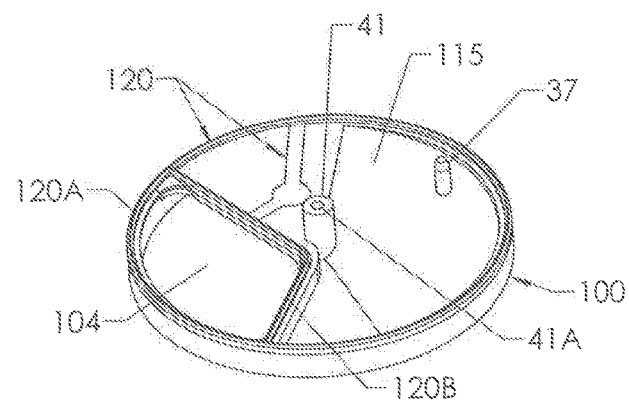
FIG. 15 is a bottom perspective view of the top portion of the sample container cap of FIG. 1.
Figure 13:
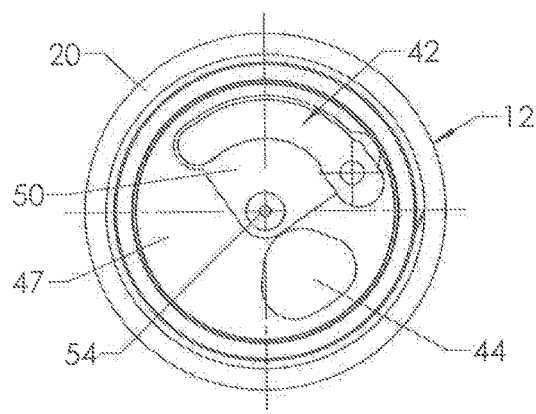
FIG. 13 is an alternate bottom view of the bottom portion of the sample container cap of FIG. 1.
Figure 16:
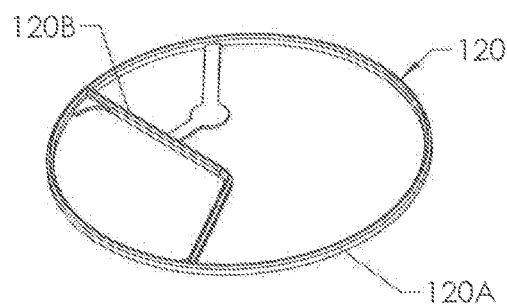
FIG. 16 is a bottom perspective view of a seal used between the top portion and bottom portion of the sample container cap of FIG. 1.
Figure 17:
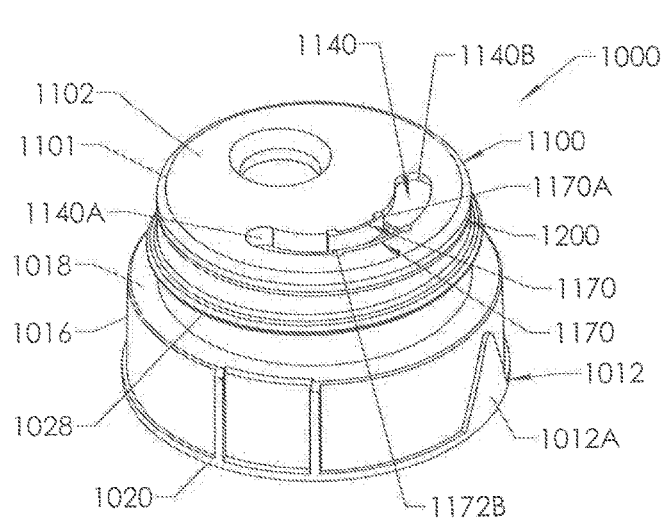
FIG. 17 is a side perspective view of an alternate sample container cap.
Figure 19:
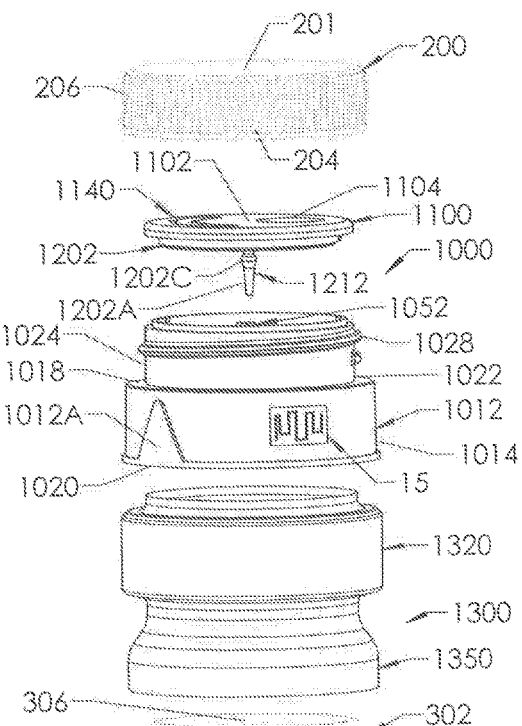
FIG. 19 is a side, perspective, partially-exploded view of the sample container cap of FIG. 17, showing a top closure, and sample container in phantom, and showing an embodiment of a security feature.
Figure 18:
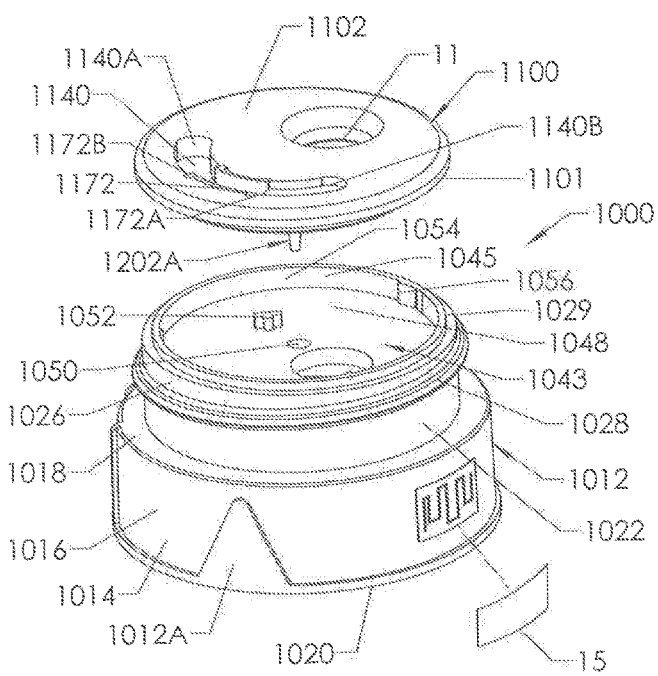
FIG. 18 is a partially-exploded, side perspective view of the sample container cap of FIG. 17.
Figure 20:
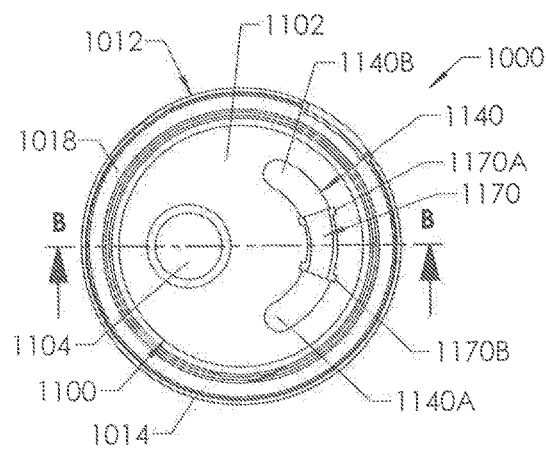
FIG. 20 is a top view of the sample container cap of FIG. 17.

As shown, for example, in FIGS. 15-16, cap 10 includes a gasket 120 preferably comprised of a flexible polymer. Gasket 120 has an annular outer gasket portion 120A and a top opening seal 120B. Gasket 120 is preferably over-molded to top portion 100, although it could be one or more separate pieces and need not be over molded to top portion 100. Portion 120A rests on and presses against top surface 58 of plate 53 to create a seal between top portion 100 and bottom portion 12. Top opening seal 120B surrounds top opening 104 and is configured to slide across upper surface 48 of plate 43 of bottom portion 12, but is compressed sufficiently to still create a fluid-tight seal between top opening 104 and top surface 48 when cap 10 is in its closed position.

Alternatively, the sealing function could be performed in part by an O-ring fitted to the outer diameter of the top portion 100. Another type of seal style that could be used is a "lip-seal" that could be over-molded to either the top portion 100 or the bottom portion 12.

Operation

As can be seen, for example, in FIGS. 7 and 10, top portion 100 is attached to bottom portion 12 by aligning the top portion using an arrow or other indicator 12A on bottom portion 12 with an arrow or other indicator (not shown) on top portion 100 so that: (1) cam 36 is positioned in channel 42 at first end 42A, and (2) spring 36 is positioned into depression 50 with leg 34B retained by leg 52 and leg 34B positioned against a projection 36C of cam 34.

Fastener 38 is then pressed through washer 40 and through aperture 54 and threaded into opening 41A of stem 41 of top portion 100. Fastener 38 is only tightened sufficiently, such as by utilizing a torque tightening device, to compress section 120B of seal 120 against the upper surface 48 of plate 43 of bottom portion 12 to create a seal while still allowing top portion 100 to rotate independently of bottom portion 12 and vice versa.

Cap 10 is then attached to a structure, such as a housing 1, adapter 400, or other structure, which is directly or indirectly attached to a machine from which a fluid sample is to be taken, or cap 10 could be directly attached to the machine. Container 300 can be attached to bottom portion 12 of cap 10 before or after cap 10 is attached to the housing 1, adapter 400, or other structure. Preferably, sample container 300 is attached to bottom portion 12 before cap 10 is connected to housing 1, adapter 400, or other structure, and cap 10 with container 300 connected are shipped together. Security structure 1350 can be attached (if desired) to cap 10 and container 300.

Figure 11:
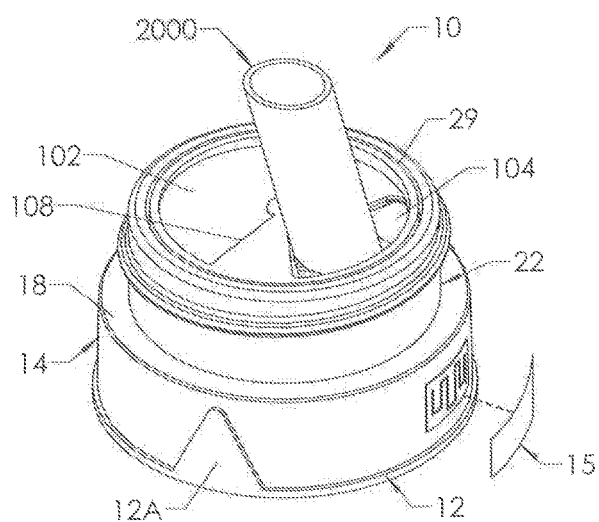
FIG. 11 is a side perspective view of the sample container cap of FIG. 1 that further shows a fluid sample tube.
Figure 12:
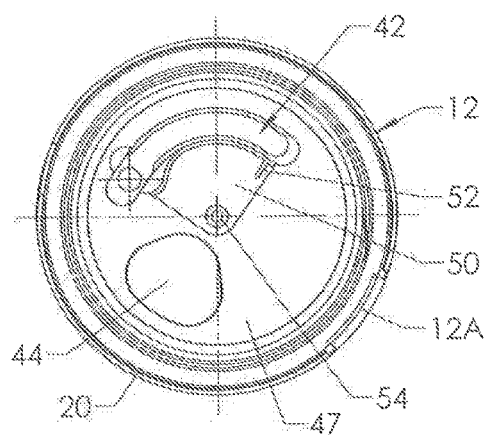
FIG. 12 is a bottom view of the bottom portion of the sample container cap of FIG. 1.

As shown in FIG. 11, a housing (not shown in this Figure) includes a fluid sample tube 2000. As cap 10 is threaded into the housing, adapter 400, or other structure, one or more threads 28 mate with and are received by one or more threads in the housing, adapter 400, or other structure. As cap 10 is threaded, it moves upwards until tube 2000 interfaces with and is received in opening 104 and butts against leg 108, as shown in FIG. 11. As cap 10 continues to be rotated and threaded farther upwards, tube 2000, which is stationary and engaged with opening 104 and leg 108 causes top portion 100 to remain stationary relative bottom portion 12, which continues to rotate.

As bottom portion 12 continues to rotate, pin 41, which extends from the bottom surface 115 of top portion 100 and into opening 36C of cam 36, causes cam 36 to remain stationary. Channel 42 rotates about cam 36, as shown in FIGS. 4-6. The channel 42 moves so that the cam position at the first end 42A of channel 42 to a second position at second end 42B, as shown in FIGS. 4-5. This compresses spring 34 to bias cam 36 back towards end 42A when tube 2000 no longer holds top portion 100 stationary.

When cap 10 is in its first position (also called a first, closed position) when cam 36 is at second end 42B, top opening 104 and bottom opening 44 do not align and cap 10 is configured to not permit the passage of fluid therethrough. When cap 10 is in its second position (also called an open position) when cam 36 is at end 42B of channel top opening 104 and bottom opening 44 align and cap 10 is configured so that fluid, which first passes through tube 2000, will pass through top opening 104 and bottom opening 44, through cavity 30 in bottom portion 12, and enter container 300.

Turning now to FIGS. 4-6, FIG. 4 illustrates the travel of channel 42 around cam 36 as bottom portion 12 rotates independently of top portion 100. Initially, cam 36 is preferably positioned at first end 42A of channel 42 when the bottom portion 12 and top portion 100 are first connected, and the cap 10 is in its first, closed position.

When cap 10 is removed from the housing, adapter 400, or other structure to which it is attached it is rotated and unscrewed, which causes cap 10 to move downward and tube 2000 to disengage from opening 104 and leg 108. This causes biased, compressed spring 34 to move cam 36 back to its first, closed position at end 42A of channel 42. Alternatively, to assist in preventing tampering with the fluid sample in container 300, cam 36 can move into a locking section 42C (i.e., move into a third, closed position), which is a slot in channel 42. Slot 42C can be at an angle (such as perpendicular to slot 42 or at a 30°-90° angle relative the other portion of channel 42 to which it connects) and/or have a bottom surface that is lower than the bottom surface of channel 42 so once cam 36 is positioned in slot 42C it cannot be moved out except by exerting enough force to break the pin 41. In that case, the pin 41 would fall into container 300 and into the fluid sample. Upon seeing the pin in a fluid sample, a technician testing the sample fluid would know that someone could have possibly tampered with the sample. When cap 10 is in the third, closed position it may be referred to as being locked.

Once the cap 10 has moved back to its first, closed position (with cam 36 at end 42A of channel 42) or to its third, closed position (in slot 42C) the openings 104 and 44 do not align and cap 10 is in a closed position and is configured so that fluid cannot pass through it. That helps prevent leakage of fluid from a sample container 300 and helps prevent contaminants from the outside entering sample container 300.

Embodiment 2

Turning now to FIGS. 17-43 an alternative fluid sample container cap (or "cap") 1000 is shown. Cap 1000 has a bottom portion 1012 and a top portion 1100. One or more security structures 1300, such as structure 1320 and structure 1350 (shown, for example, in FIGS. 19 and 80), may be utilized to secure a top closure 200 to cap 1000 and/or secure container 300 to cap 1000. Security structure 1320 and security structure 1350 may be shrink-wrap plastic.

Bottom portion 1012 has the same structure as previously-described bottom portion 12 except as described and shown herein. Bottom portion 1012 has a lower section 1014 with an outer annular wall 1016, an upper ledge 1018, and a lower edge 1020. Bottom portion 1012 further includes an upper section 1022 that has an outer diameter that is less than the outer diameter of lower section 1014. Upper section 1022 further comprises an annular outer wall 1024, with a threaded top 1026 that includes one or more outer threads 1028 that are configured to be received in a housing (for example, housing 1 shown in FIGS. 38, 40, 42, 68, 70, and 72), or an adapter 400 (shown in FIGS. 74-79), or other structure. One or more threads 1028 are also configured to receive top closure 200: (1) before cap 1000 is attached to a housing, adapter, or other structure, and (2) after a fluid sample is received in a container 300 and the cap 1000 is moved to a closed position, as explained further herein, and removed from the housing, adapter or other structure. Upper section 1022 further includes an upper lip 1029.

Bottom portion 1012 has a plate 1043 with a top surface 1048 and bottom surface 1047 that helps define lower cavity 1030. Plate 1043 includes a bottom opening (or "opening") 1044 configured for the passage of fluid therethrough and into sample container 300. Plate 1043 further includes an aperture 1050, which is preferably positioned in its center, and a stop 1052. Bottom portion 1012 also includes a top cavity 1045 having an inner wall 1053 having a projection 1056.

Bottom portion 1012 further includes a lower cavity 1030 that includes one or more threads 1032, which are configured to receive one or more threads 302, shown on FIG. 1, of sample container 300 in order to connect sample container 300 to cap 1000. One or more threads 1032 are of any suitable configuration to mate with the one or more threads 302 on container 300, which may vary in structure based on the type of container.

Top portion 1100 has the same structure as previously-described top portion 100 except as described and shown differently herein. Top portion 1100 is positioned in upper cavity 1045 of bottom portion 1012. Top portion 1100 has an upper, annular lip 1101, a top surface 1102, and a channel 1140 having an insert 1170 positioned therein. Top portion 1100 further includes a top opening 1104 that is configured for the passage of fluid therethrough. Top portion 1100 has a bottom surface 1106 and may have one or more gaskets, such as one-piece gasket 1200, over-molded or otherwise attached thereto, although the one or more gaskets need not be attached.

Channel 1140 has a first end 1140A, a second end 1140B, and a restricted area between first end 1140A and 1140B, wherein the restricted area is created by insert 1170. Insert 1170 as shown is part of seal 1200 and is formed during the molding of seal 1200. Insert 1170 may, however, be a separate structure, or the restricted area may be formed in another manner. Insert 1170 has a first end 1170A that has a first width and a second end 1170B that has a second width, wherein the second width is less than the first width.

Stop 1052 is positioned on surface 1048 and is configured to abut structure 1206 to help prevent over rotation of bottom portion 1012 relative top portion 1100 when cap 1000 is moved from its first, closed to its second, open position. Stop 1052 is configured to abut structure 1208 to help prevent over rotation of bottom portion 5012 relative top portion 1100 when cap 1000 is moved from its second, open position to its first, closed position or to a third, closed position.

Gasket

Figure 23:
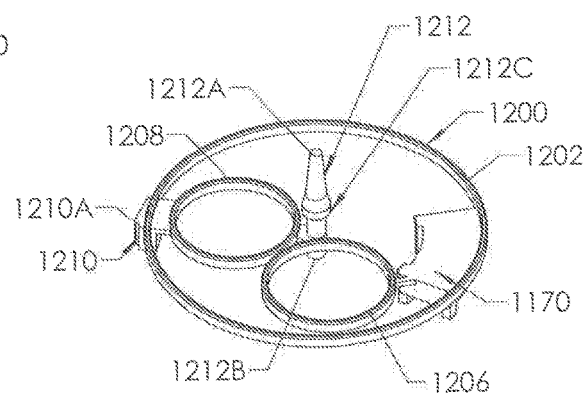
FIG. 23 is a bottom, perspective view of the sealing structure of the sample container cap of FIG. 17.
Figure 21:
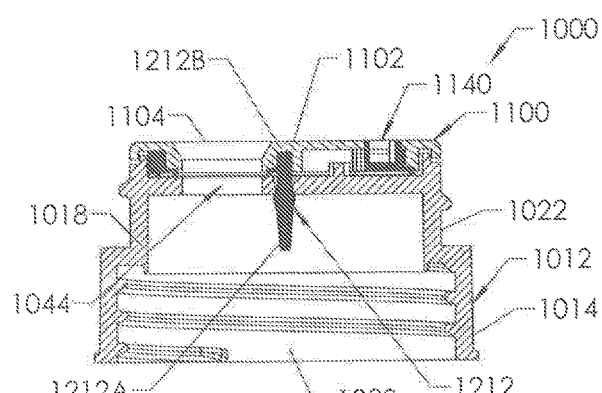
FIG. 21 is a side, cross-sectional view of the sample container cap of FIG. 20 taken through line B-B.
Figure 24:
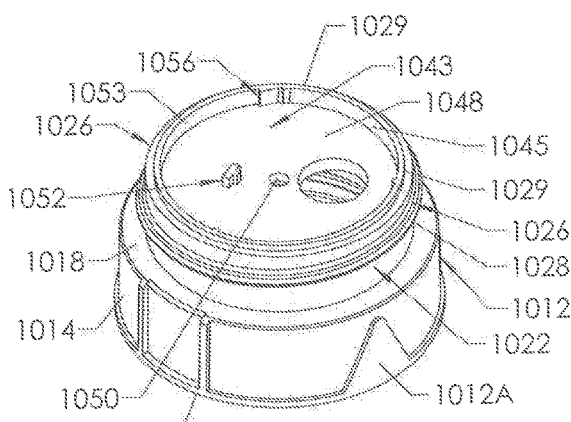
FIG. 24 is a side, perspective view of the bottom portion of the sample container cap of FIG. 17.
Figure 22:
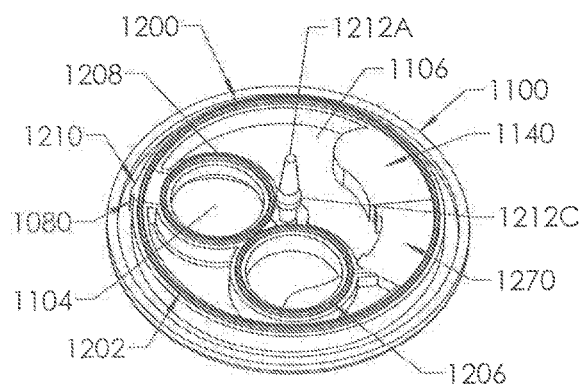
FIG. 22 is a bottom, perspective view of the top portion of the sample container cap of FIG. 17.
Figure 25:
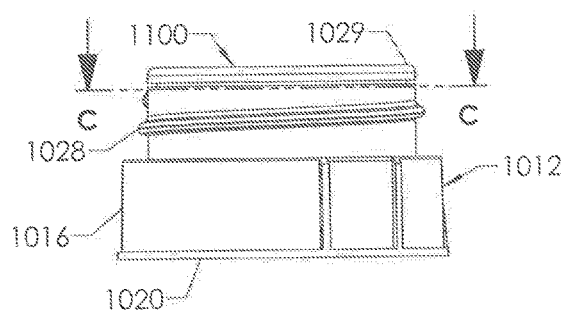
FIG. 25 is a side view of the bottom portion of the sample container cap of FIG. 17.
Figure 26:
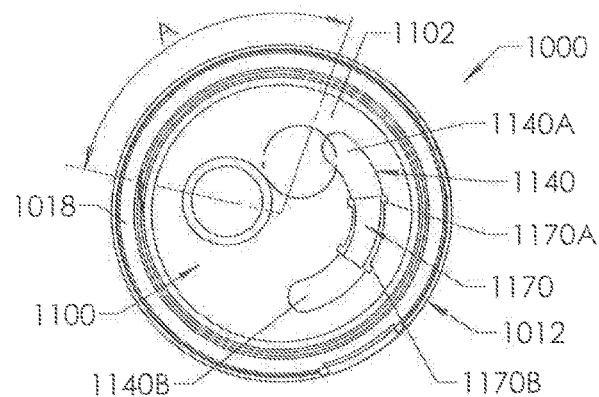
FIG. 26 is a top view of the sample container cap of FIG. 17.
Figure 27:
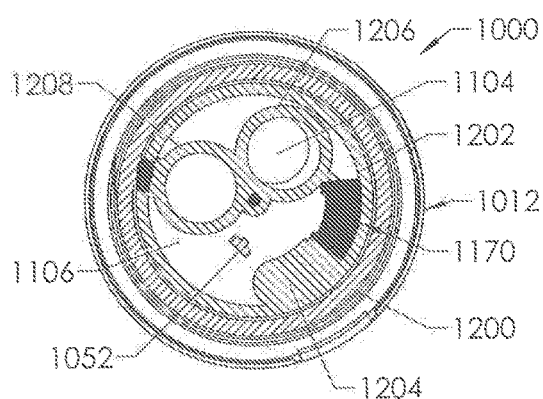
FIG. 27 is a cross-sectional view of the sample container cap of FIG. 26 taken through line C-C of FIG. 25.
Figure 28:
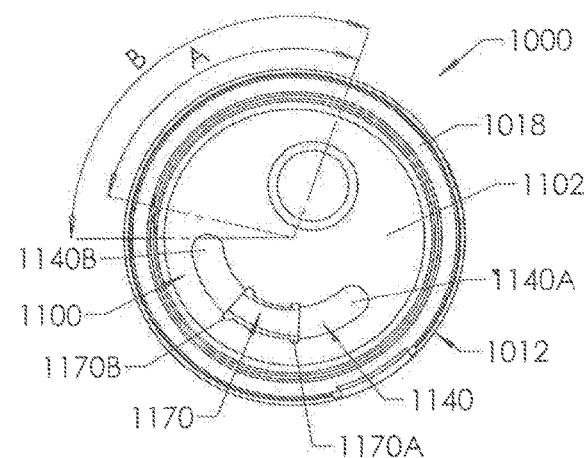
FIG. 28 is an alternate top view of the sample container cap of FIG. 17.
Figure 29:
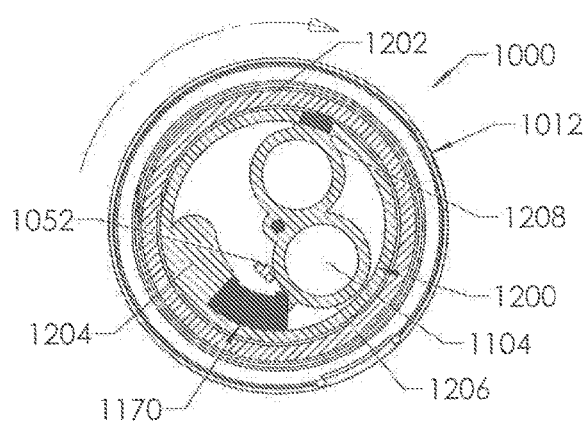
FIG. 29 is a cross-sectional view of the sample container cap of FIG. 28 taken through line C-C of FIG. 25.
Figure 30:
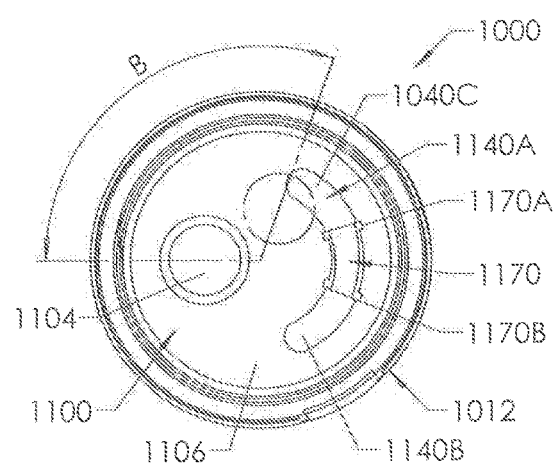
FIG. 30 is an alternate top view of the sample container cap of FIG. 17.
Figure 31:
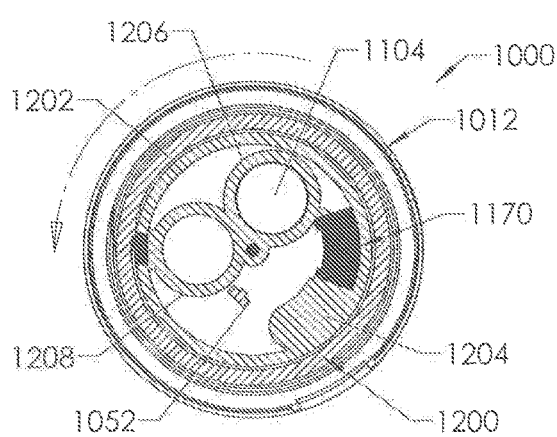
FIG. 31 is a cross-sectional view of the sample container cap of FIG. 30 taken through line C-C of FIG. 25.
Figure 32:
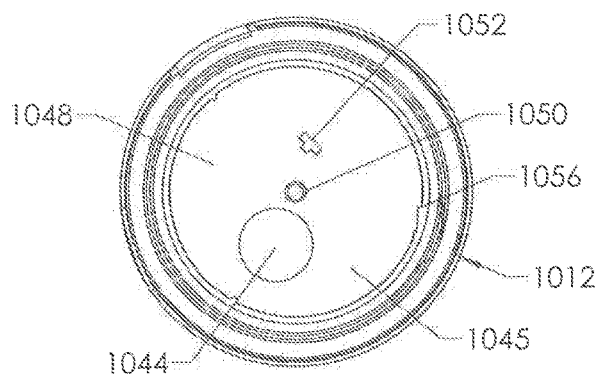
FIG. 32 is a top view of the bottom portion of the sample container cap of FIG. 17.
Figure 33:
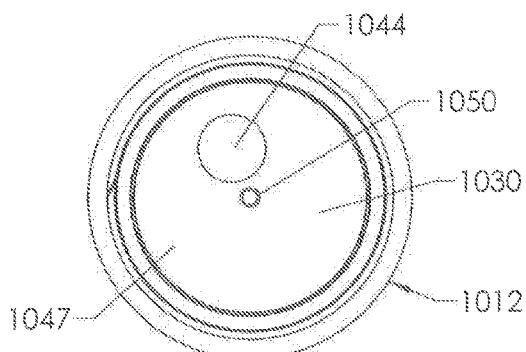
FIG. 33 is a bottom view of the bottom portion of the sample container cap of FIG. 17.
Figure 34:
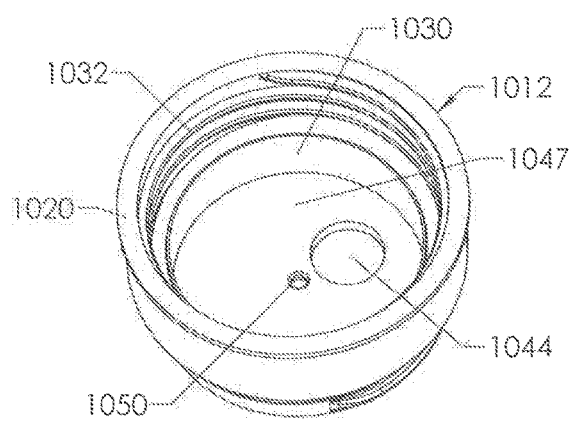
FIG. 34 is a bottom, perspective view of the bottom portion of the sample container cap of FIG. 17.
Figure 35:
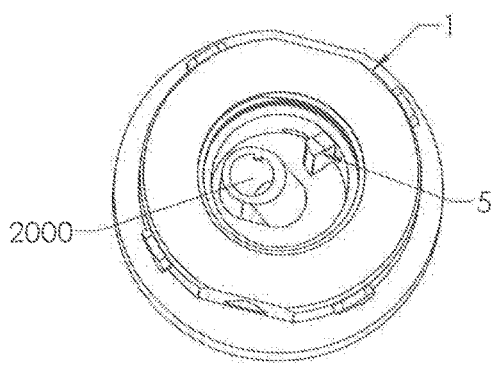
FIG. 35 is a bottom view of the bottom portion of a housing to which a sample container cap according to this disclosure may be attached.
Figure 36:
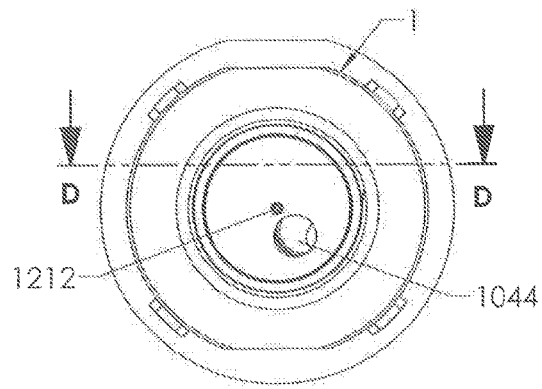
FIG. 36 is a bottom view of the sample container cap of FIG. 17 connected to a housing.
Figure 37:
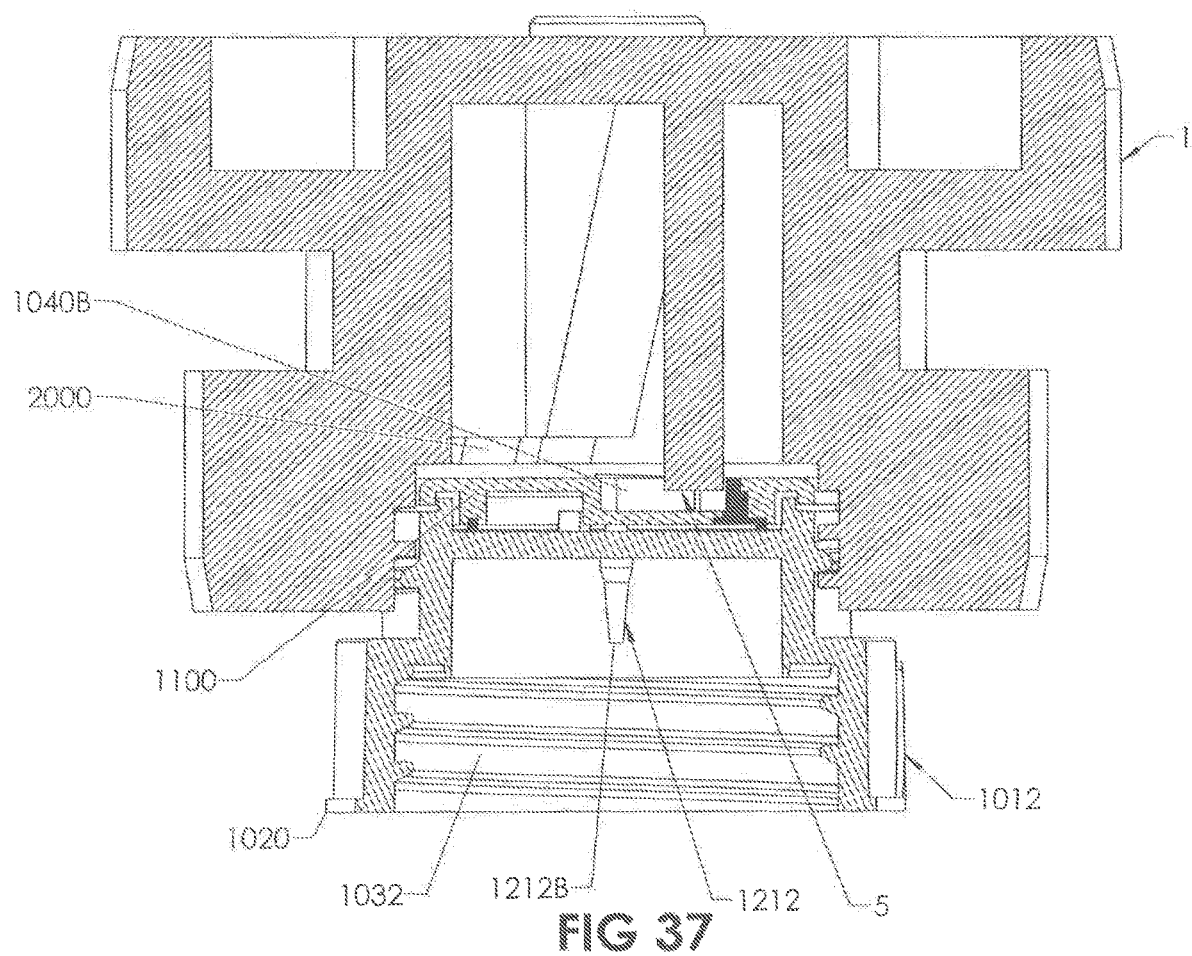
FIG. 37 is a side, cross-sectional view of the sample container cap and housing of FIG. 36 taken through line D-D of FIG. 36.
Figure 38:
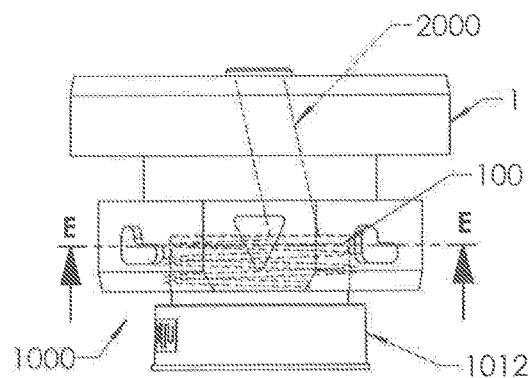
FIG. 38 is side view of the sample container cap and housing of FIGS. 35-37 showing threads and fluid sample tube in phantom.
Figure 39:
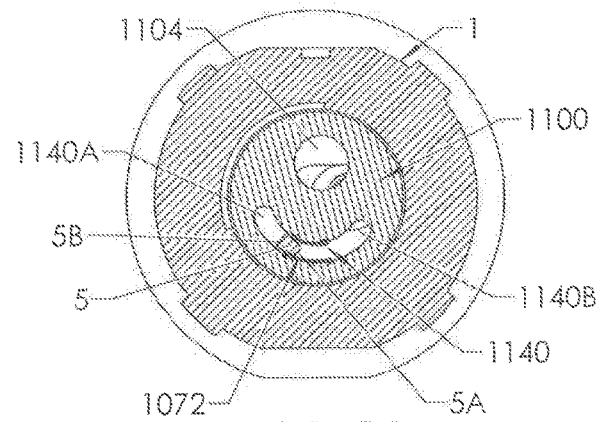
FIG. 39 is a bottom, cross-sectional view of the sample container cap of FIG. 38 taken though line E-E.
Figure 40:
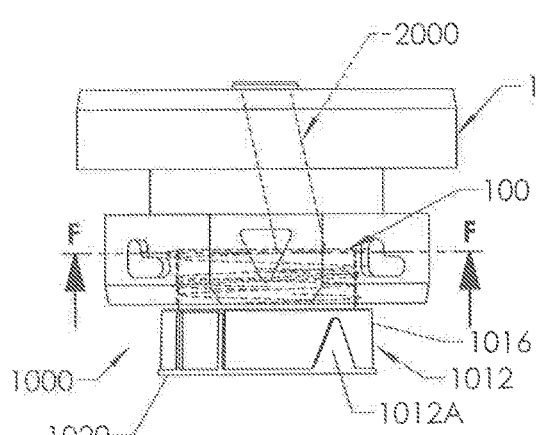
FIG. 40 is an alternate side view of the sample container cap and housing of FIG. 38.
Figure 41:
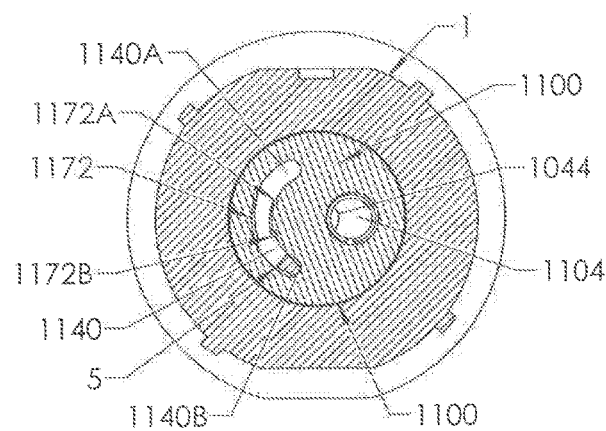
FIG. 41 is a bottom, cross-sectional view of the sample container cap of FIG. 40 taken through line F-F.
Figure 42:
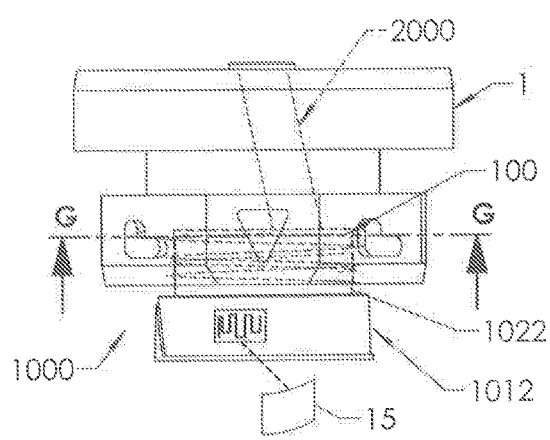
FIG. 42 is an alternate, side view of the sample container cap and housing of FIG. 38.
Figure 43:
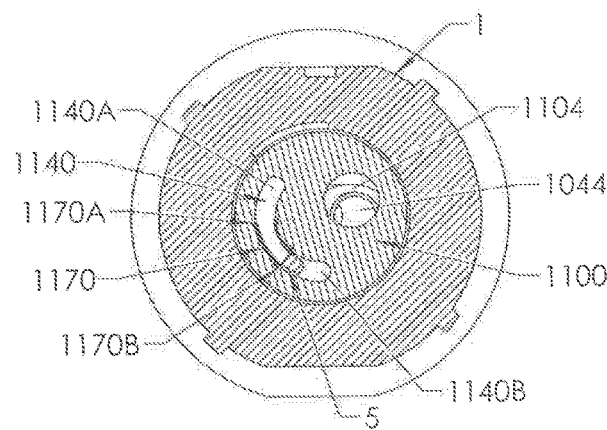
FIG. 43 is a bottom, cross-sectional view of the sample container cap and housing of FIG. 42 taken through line G-G.

Gasket 1200, as shown for example, in FIGS. 22-23, is a one-piece structure preferably comprised of a compressible polymer material that is preferably over-molded onto top portion 1100 although gasket 1200 may be an independent structure and/or be more than one piece. Gasket 1200 includes (1) an annular outer portion 1202 that rests on and presses against top surface 1058 of plate 1043 to seal between the top portion 1100 and bottom portion 1012, (2) portion 1210 that includes a projection or detent 1210A that is configured to press against a projection 1056 in bottom portion 1012, (3) an insert 1170 that is configured to fit in channel 1140, (4) a first circular seal 1206 configured to press against and slide across surface 1048 of plate 1043 and to seal between opening 1044 and top portion 1100 when cap 1000 is in a closed position, (5) a second circular seal 1208 that surrounds top opening 1104 and is configured to press against and slide across surface 1048 and to seal between top opening 1104 and top surface 1048 when cap 1000 is in a closed position.

A stem 1212 as shown is part of gasket 1200, although it may be a separate component. Stem 1212 is configured to press into and partially through, and be retained in, aperture 1050 in order to connect top portion 1100 to bottom portion 1012. Stem 1212 has a lower tip 1212A, a center hub 1212C, and a top tip 1212B. Lower tip 1212A and hub 1212C are positioned in cavity 1030 when cap 1000 is assembled as described further below.

Alternatively, the sealing function could be performed in part by an O-ring fitted to the outer diameter of top portion 1100. Another type of seal style that could be used is a "lip-seal" over-molded to either the top portion 1100 or the bottom portion 1012.

Operation

Bottom portion 1012 is connected to top portion 1100 by first aligning the top portion 1100 and the bottom portion 1012 in any suitable manner, such as the one described with respect to cap 10. Once aligned, stem 1212 is pressed into aperture 1050 until hub 1212C compresses and passes through aperture 1050 and expands on the bottom side 1057 of plate 1043 (the hub 1212C is basically snap-fit into position) and is positioned in cavity 1030 against bottom surface 1057.

Portion 1202 of seal 1200 is pressed against upper surface 1058 on plate 1053 of the bottom portion 1012. When first assembled, cap 1000 is in a first, closed position wherein top opening 1104 and bottom opening 1044 are not aligned and cap 1000 is configured to not allow the passage of fluid therethrough. Projection 1056 on inner wall 1053 of top cavity 1045 of bottom portion 1012 butts against projections 1210A of seal 1200 to help maintain cap 1000 in its first, closed position. Alternatively, cap 1000 could initially be in an open position with top opening 1104 and bottom opening 1044 aligned.

A container, such as container 300, may then be screwed into cavity 1030 of bottom portion 1012 with one or more threads 302 engaging one or more threads 1032.

Preferably, container 300 is attached to bottom portion 1012 before cap 1000 is connected to housing 1, adapter 400, or other structure so security structure 1350 can be attached to the container 300 and bottom portion 1012 of cap 1000. Security structure 1350 might be shrink-wrap plastic film. If the security structure is removed, torn, damaged, or broken that would indicate the possibility that someone had tampered with the sample in the sample container 300.

A top closure 200 may be attached to cap 1000 to cover top portion 1100 until cap 1000 is used. Top closure 200 preferable has one or more threads that attach to one or more threads 1028. A security structure 1320 may be attached to top closure 200 and cap 1000 to prevent removal of top closure prior to cap 1000 being used. Security structure 1320 may be shrink-wrap plastic and security structure 1320 may overlap security structure 1350.

The cap 1000 with attached container 300 and security structure 1350, and attached top closure 200 and security structure 1320 can be shipped and ultimately be attached to a housing 1, adapter 400, or other structure.

Cap 1000 is attached to a housing, adapter, or other structure that includes a stationary projection (also referred to as a projection or protrusion) 5 that is received in the channel 1140, or other structure is configured to be received in channel 1140. Turning to FIGS. 38-43, projection 5 has a first end 5A that is preferably curved or rounded in top (or plan) view and first end 5A has a first width. Projection 5 has a second end 5B that is preferably square or rectangular in top (or plan) view and that has a second width that is preferably greater than the first width.

Cap 1000 is attached to a housing 1, adapter 400, or other structure preferably by threading the one or more threads 1028 onto mating threads inside of a cavity (or opening) of housing 1, adapter 400, or other structure. As cap 1000 is threaded into the housing 1, adapter 400, or other structure, the one or more threads 1028 mate with and are received by one or more mating threads. As cap 1000 is threaded, it moves upwards until stationary projection 5, which is part of the housing 1, adapter 400, or other structure, moves into channel 1140 at first end 1140A. As cap 1000 is further rotated, channel 1140 moves along stationary projection 5 so that projection 5 goes from first end 1140A, through end 1170A of insert 1170, past end 1170B of insert 1170, and butts against end 1140B of channel 1140. This engagement of stationary projection 5 against end 1140B of channel 1140 prevents further rotation of top portion 1100 relative bottom portion 1012, and top portion 1100 is held stationary.

As bottom portion 1012 is further rotated and threaded onto the mating one or more threads, with top portion 1100 stationary, cap 1000 moves into a second, open position with top opening 1104 and bottom opening 1044 aligned (completely or partially) and cap 1000 is configured to allow the passage of fluid therethrough and into container 300. At this position a fluid sample tube 2000 may be aligned with opening 1104, although any suitable structure or method for transferring fluid may be utilized.

Over rotation of cap 1000 past the second, open position is unlikely because stop 1052 butts against (or touches) the relatively hard structure to which top opening seal 1206 is attached when cap 1000 is in the second, open position.

When cap 1000 is removed from the structure to which it was attached it is unscrewed, which causes cap 1000 to rotate in the opposite direction and move downward. As cap 1000 is rotated and unscrewed, channel 1140 moves around projection 5 until projection 5 is at second end 1170B of insert 1170. Because the second end 5B of projection 5 is wider than first end 5A, and end 5B is preferably square or rectangular, and also because end 1170B of insert 1170 is narrower than first end 1170A (i.e., has a width that is less than the width of first end 1170A), the second end 5B of projection 5 butts against and stops at second end 1170B, which prevents further rotation of top portion 1100. As cap 1000 continues to be unscrewed, bottom portion 1012 rotates while portion 1100 remains stationary. Cap 1000 then moves to a closed position, which could be the first, closed position or (in this embodiment), a third, closed position.

When in the third, closed position (or the first, closed position) the top opening 1104 and the bottom opening 1044 do not align and cap 1000 is configured to not allow the passage of fluid or outside contaminants therethrough.

Over-rotation of bottom portion 1012 to cause cap 1000 to move past the third, closed position is unlikely because stop 1052 butts against (or touches) the relatively hard structure to which bottom opening seal 1208 is attached to prevent over rotation when cap 1000 is moved to the third, closed position.

As cap 1000 is further screwed out of the structure, the channel 1140 moves lower until it is lower that projection 5, which is then no longer in channel 1140. The container 300 with cap 1000 attached can then have top closure 200 attached and be sent to a laboratory or other facility. At the laboratory the security structure 1350 is removed and the sample container 300 is unscrewed from bottom portion 1012 in order to access the sample fluid.

Embodiment 3

Turning now to FIGS. 44-73 an alternative fluid sample container cap (or "cap") 5000 is shown. Cap 5000 has a bottom portion 5012 and a top portion 5100. One or more security structures 1300, such as structure 1320 and structure 1350 (shown, for example, in FIGS. 1, 17, and 80), may be utilized to secure a top closure 200 to cap 5000 and/or secure container 300 to cap 5000. Security structure 1320 and security structure 1350 may be shrink-wrap plastic.

Bottom portion 5012 has the same structure as previously-described bottom portion 1012 except as described and shown herein. Bottom portion 5012 has a plate 5043 having a top surface 5048 and a bottom surface 5047 that helps to define lower cavity 5030. Plate 5043 includes bottom opening (or opening) 5044 configured for the passage of fluid therethrough and into a sample container, such as container 300. Plate 1043 further includes a stop 5052 on top surface 5048 and a top cavity 1045 having an annular wall 5053.

Figure 48:
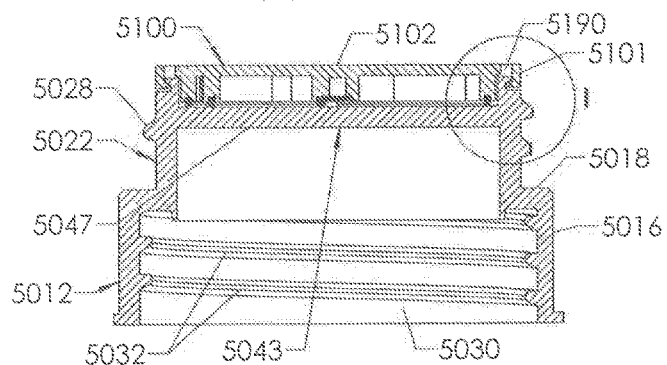
FIG. 48 is a side, cross-sectional view of the sample container cap of FIG. 47 taken through line H-H.
Figure 65:
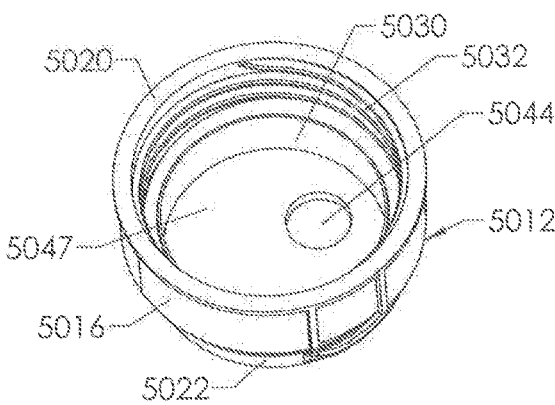
FIG. 65 is a bottom, perspective view of the sample container cap of FIG. 44.
Figure 66:
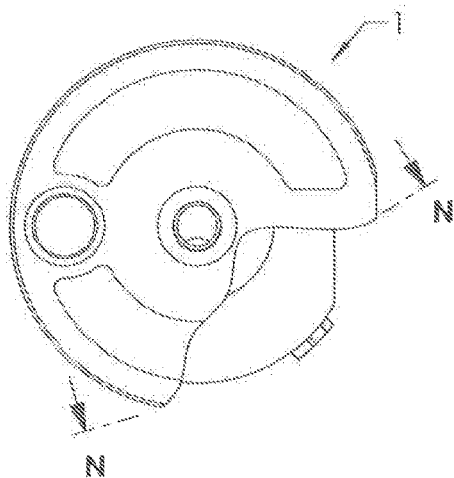
FIG. 66 is a top, cut-away view of a housing connected to the sample container cap of FIG. 44.
Figure 67:
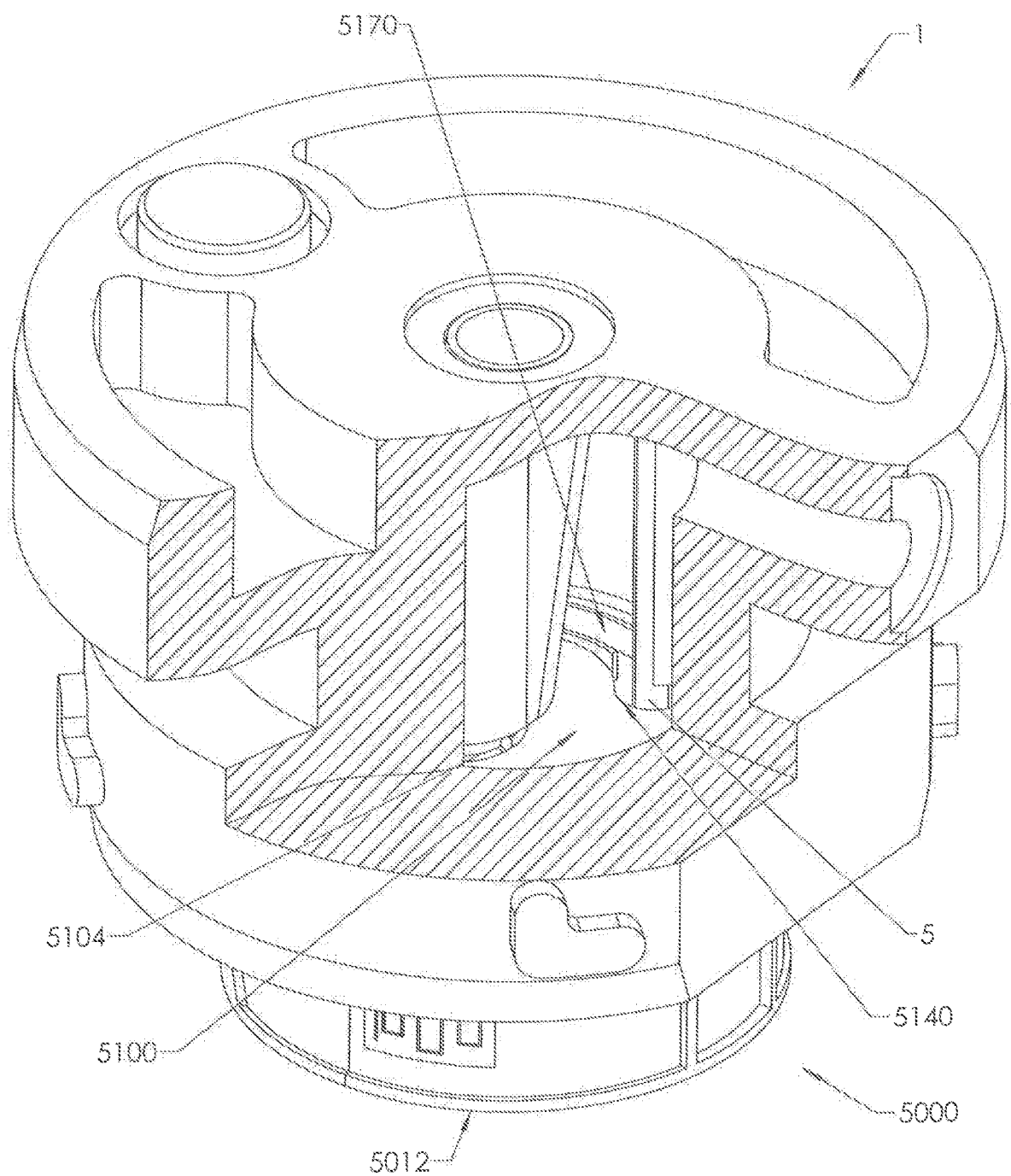
FIG. 67 is a side, perspective, partial cross-sectional view of the structure of FIG. 66 showing the housing cut-out through line N-N.
Figure 68:
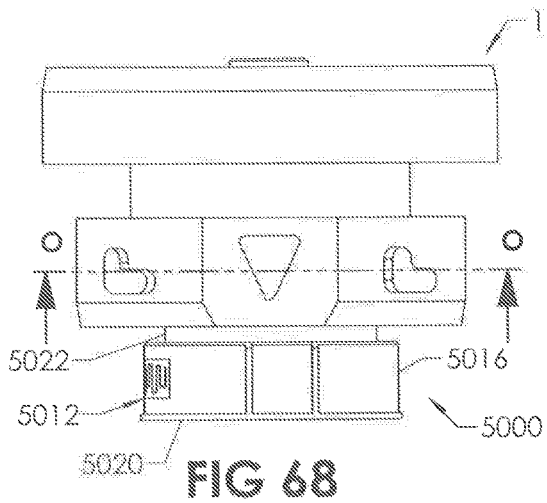
FIG. 68 is a side view of the structure of FIG. 66.
Figure 69:
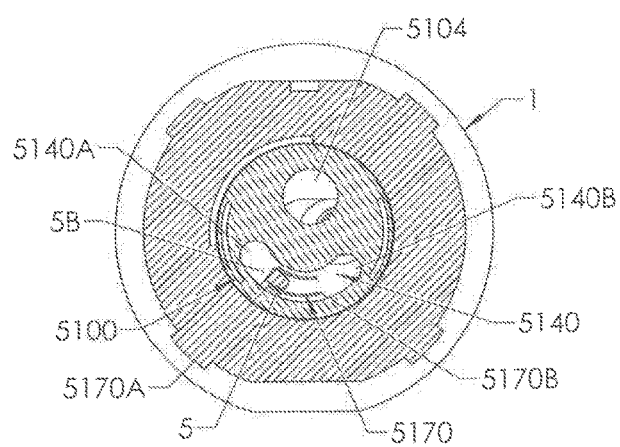
FIG. 69 is a cross-sectional view of the structure of FIG. 68 taken through line O-O.
Figure 70:
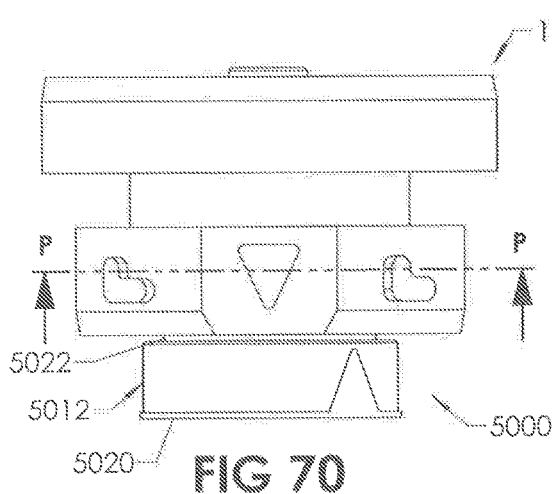
FIG. 70 is an alternate side view of the structure of FIG. 66.

Bottom portion 5012 includes a lower cavity 5030, shown in FIGS. 48 and 65, that includes one or more threads 5032, which are configured to receive one or more threads 302, shown, for example, on FIG. 1, of sample container 300 in order to connect sample container 300 to cap 5000. One or more threads 5032 are of any suitable configuration to mate with the one or more threads 302 on container 300, which may vary in structure based on the type of container.

Bottom portion 5012 has a lower section 5014 with an outer annular wall 5016, an upper ledge 5018, and a lower edge 5020. Bottom portion 5012 further includes an upper section 5022 that has an outer diameter that is less than the outer diameter of lower section 5014. Upper section 5022 further comprises an annular outer wall 5024, with a threaded top 5026 that includes one or more outer threads 5028 that are configured to be received in a housing 1 (shown in FIGS. 38, 40, 42, 68, 70, and 72), or an adapter 400 (shown in FIGS. 74-79), or other structure. One or more threads 5028 are also configured to receive top closure 200: (1) before cap 5000 is attached to a housing, adapter, or other structure, and (2) after a fluid sample is received in a container 300 and the cap 5000 is moved to a closed position, as explained further herein, and removed from the housing 1, adapter 400, or other structure.

A friction track 5090 is also formed in top surface 5048 of plate 5043. Friction track 5090 is a series of indentations or slots in top surface 5048 that are configured to receive a projection 5161 from top portion 5100 when cap 5000 is assembled. Then, when bottom portion 5012 is rotated relative top portion 5100, or vice versa, the user feels a slight resistance and (preferably) hears a clicking sound as projection 5161 moves from indentation to indentation in friction track 5090.

Upper section 5022 further includes an upper lip 5029 having an outer edge 5029A that as shown is chamfered, and a groove 5300 configured to receive an inward-facing extension 5101B of outer wall 5101 of top portion 5100. Groove 5300 includes two protrusions 5095A and 5095B configured to interface with a protrusion 5195A of top portion 5100.

Figure 53:
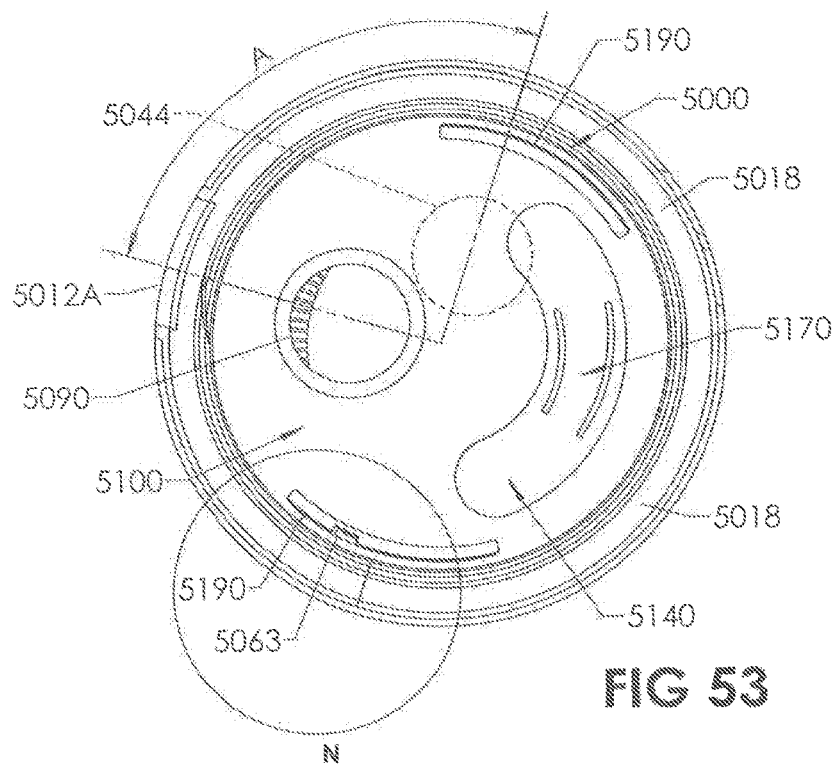
FIG. 53 is a top view of the sample container cap of FIG. 44.
Figure 53A:
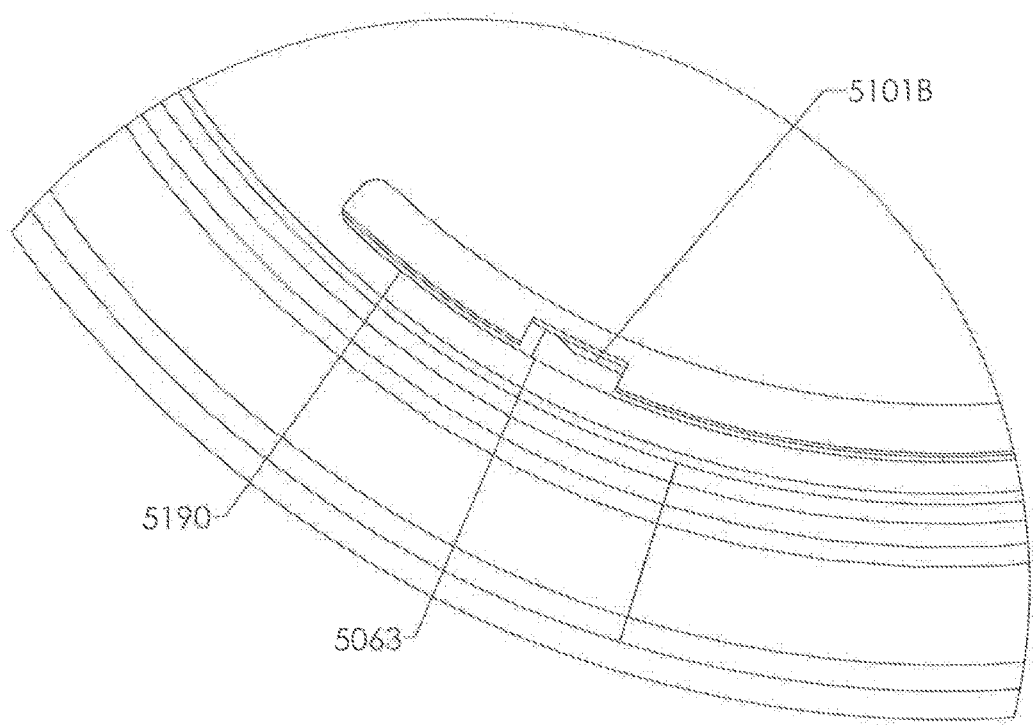
FIG. 53A is an enlarged view of the structure designated as N in FIG. 53.
Figure 54:
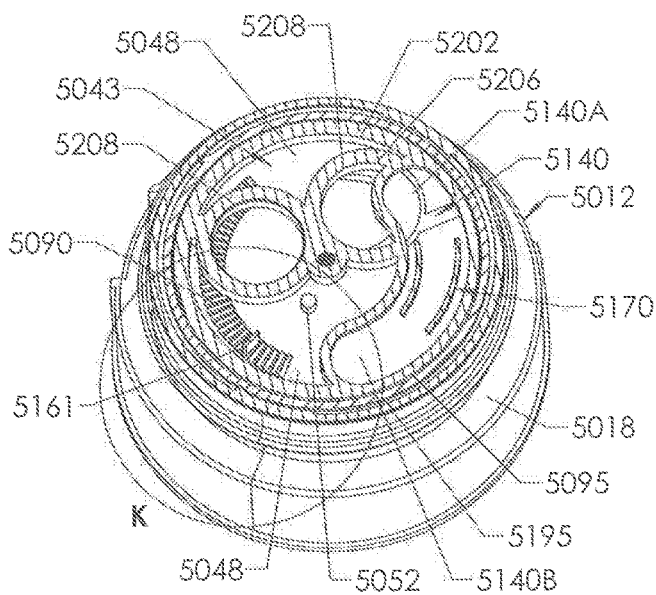
FIG. 54 is a top, cross-sectional view of the sample container of FIG. 53 taken through line J-J of FIG. 52.
Figure 55:
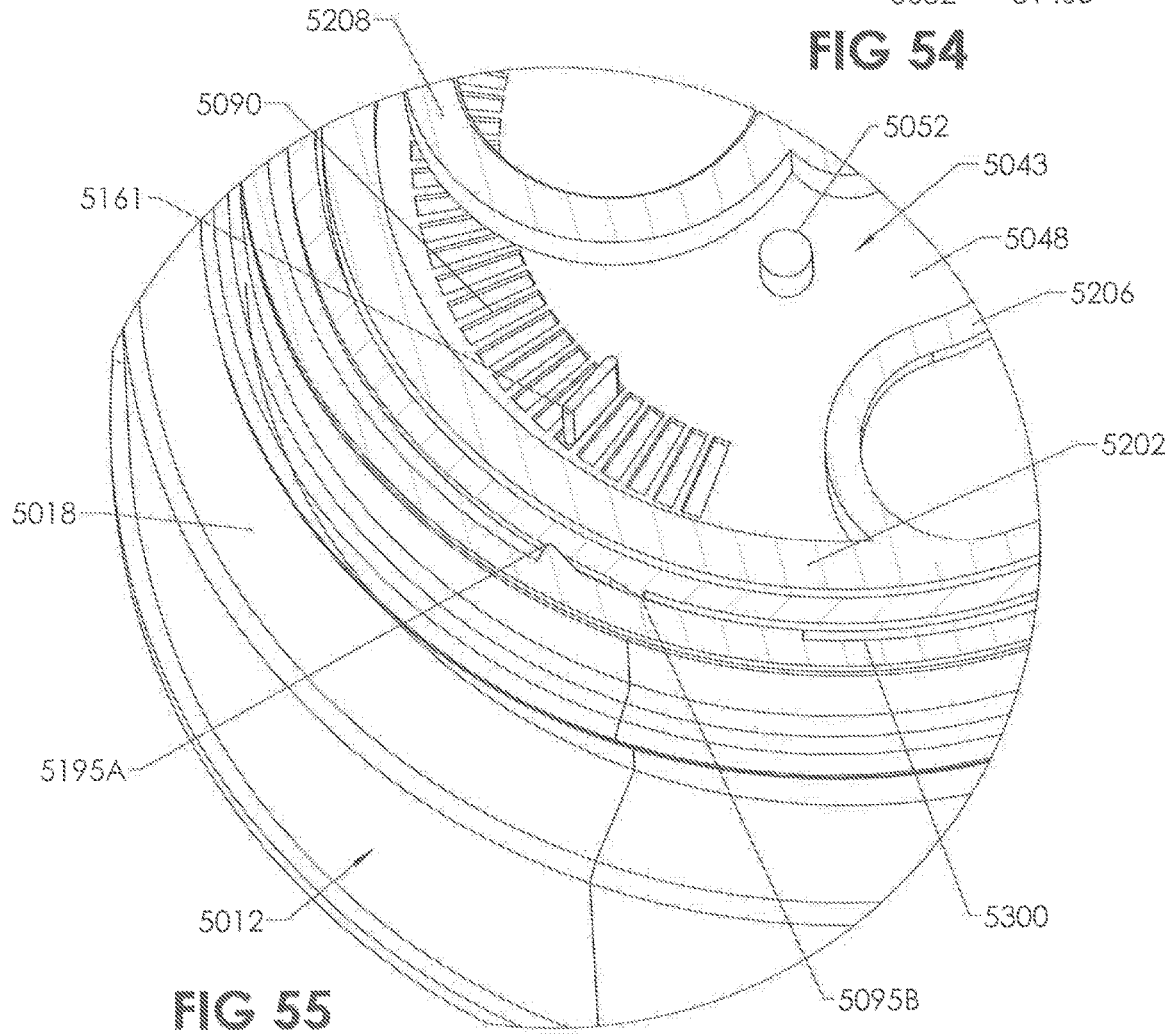
FIG. 55 is an enlarged view of the structure designated as K in FIG. 54.
Figure 56:
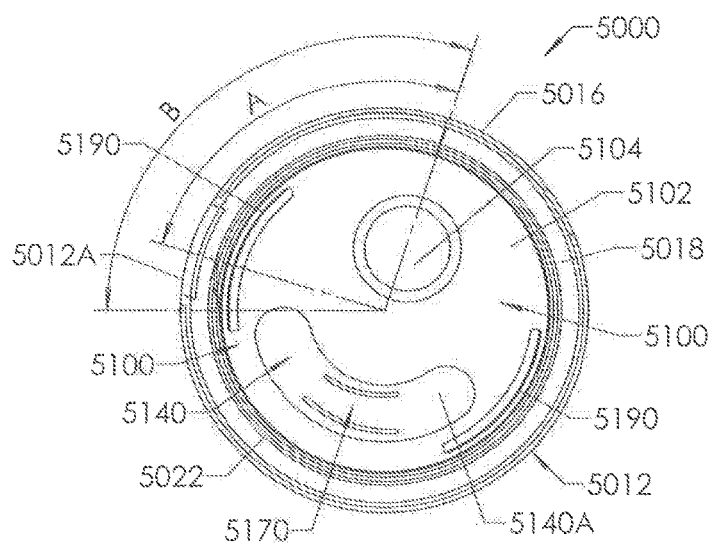
FIG. 56 is an alternate top view of the sample container cap of FIG. 44.
Figure 59:
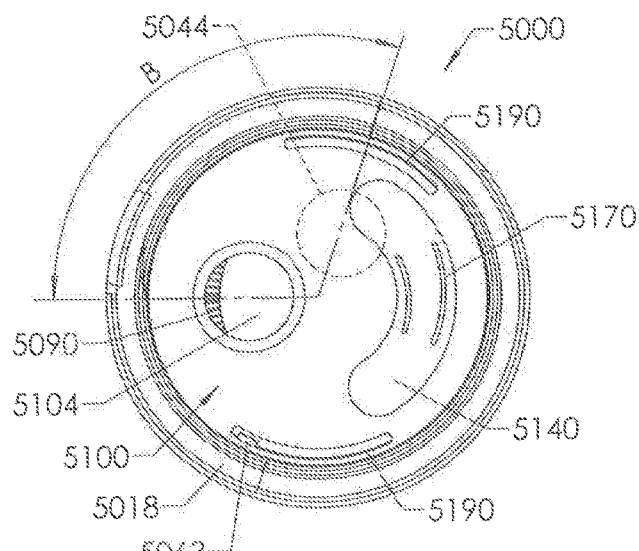
FIG. 59 is an alternate top view of the sample container cap of FIG. 44.
Figure 60:
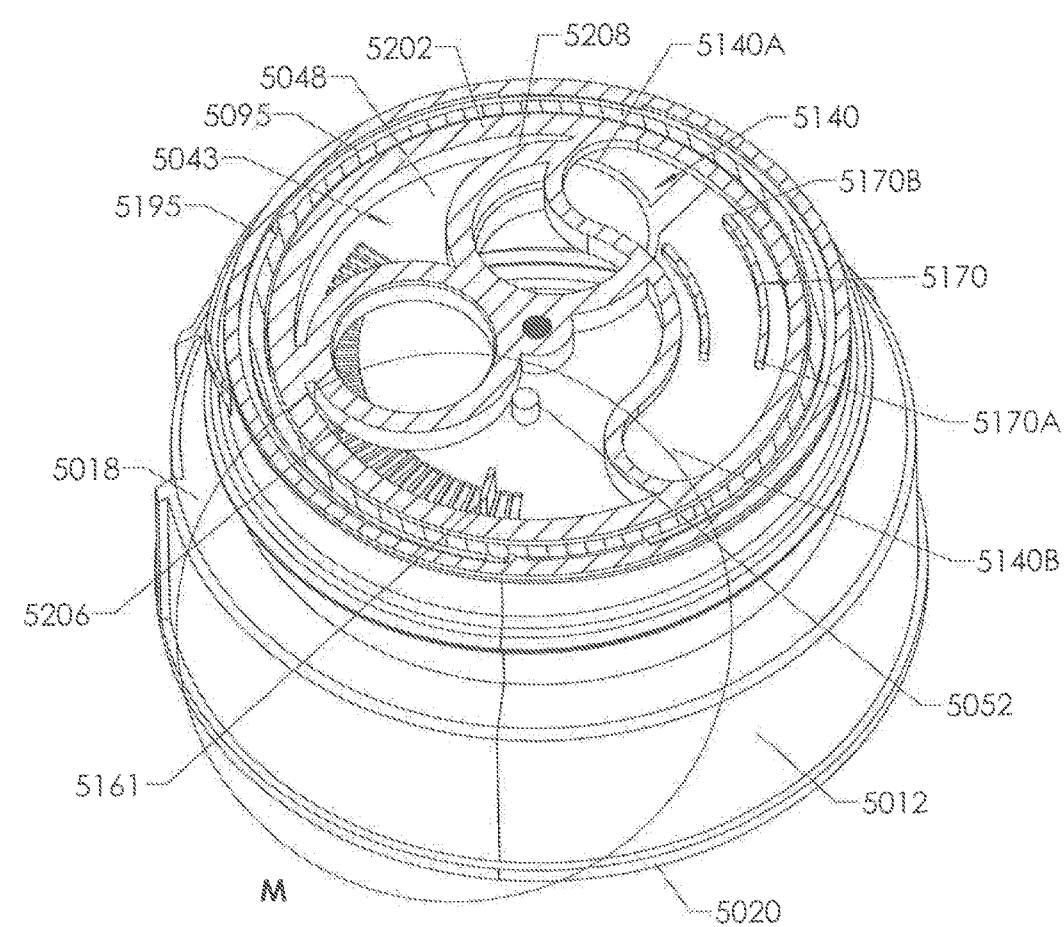
FIG. 60 is a top, cross-sectional view of the sample container of FIG. 59 taken through line J-J of FIG. 52.
Figure 62:
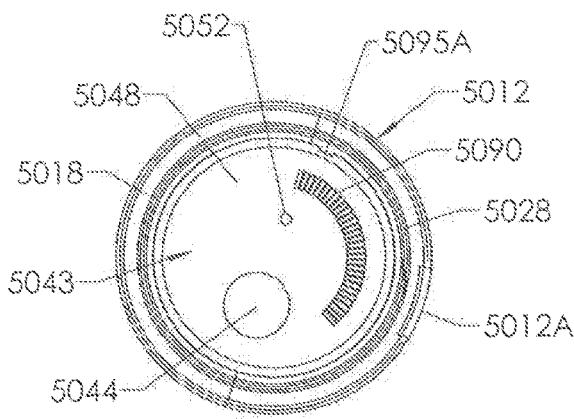
FIG. 62 is a top view of the bottom portion of the sample container cap of FIG. 44.
Figure 63:
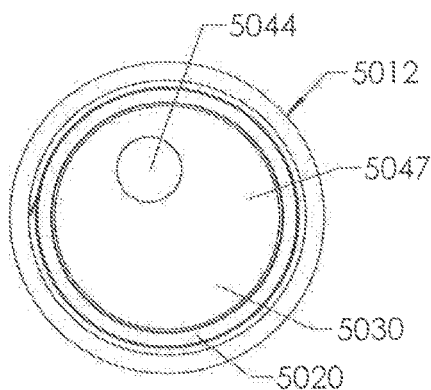
FIG. 63 is a bottom view of the sample container cap of FIG. 44.
Figure 64:
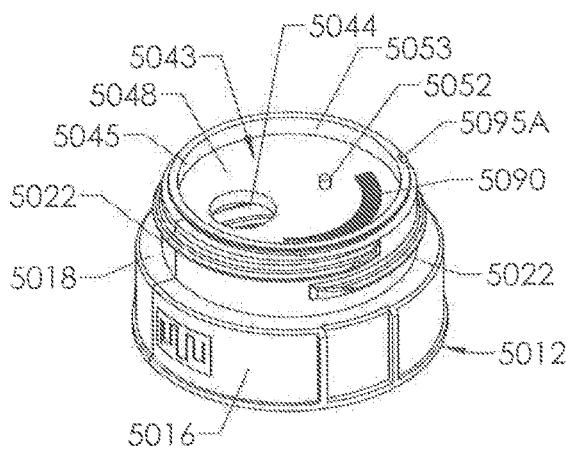
FIG. 64 is a side, perspective view of the bottom portion of the sample container cap of FIG. 44.

Upper lip 5029 of lower portion 5012 has a cut-out (or indentation) 5063 formed therein, as can be seen, for example, in FIGS. 53, 53A, and 59, wherein indentation 5063 is configured to receive a protrusion 5195A in order to align and attach top portion 5100 to bottom portion 5012.

Stop 5052 is positioned on top surface 5048 of plate 5043 and is configured to abut a rigid plastic structure to which top opening seal 5206 is attached to help prevent over rotation of bottom portion 5012 relative top portion 5100 when cap 5000 is moved to its second, open position. Stop 5052 is configured to abut a rigid plastic structure to which bottom opening seal 5208 to help prevent over rotation of bottom portion 5012 relative top portion 5100 when cap 5000 is moved from its second, open position to its third, closed position.

Top portion 5100 has the same structure as previously-described top portion 1100 except as described and shown herein. Top portion 5100 has a top surface 5102, an outer rim 5126, an opening (or top opening) 5104 that is configured to allow fluid to pass therethrough, and a channel 5140. Top portion 5100 has a bottom surface 5106 and may have one or more gaskets, such as gasket 5200, over-molded or otherwise attached thereto, although gasket 5200 may be any suitable structure or structures.

Channel 5140 has a first end 5140A, a second end 5140B, and a restricted area between first end 5140A and 5140B. In the embodiment shown the restricted area is formed by an insert 5170 that is positioned in channel 5140, and in this embodiment, is formed as a part of channel 5140. Insert 5170 has a first end 5170A that has a first width and a second end 5170B that has a second width, wherein the first width is less than the second width.

Figure 47:
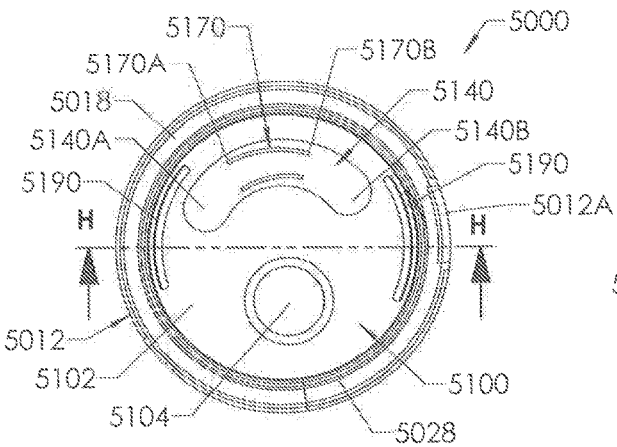
FIG. 47 is a top view of the sample container cap of FIG. 44.
Figure 49:
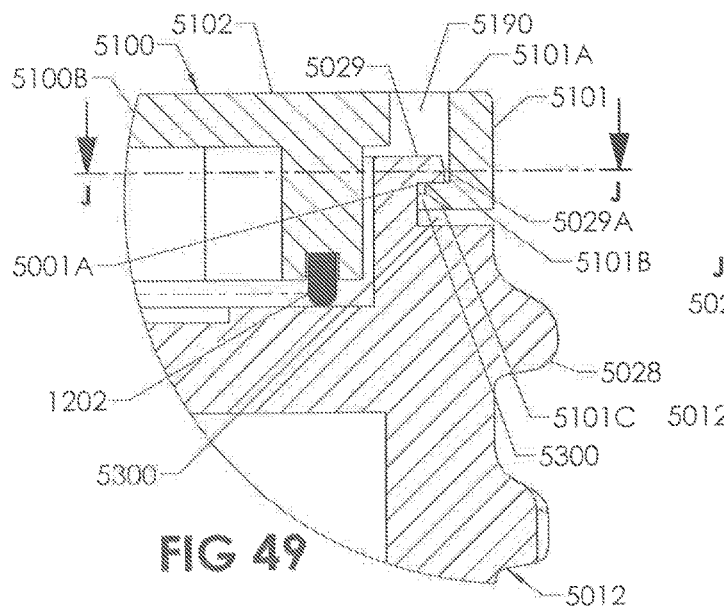
FIG. 49 is an enlarged view of the section designated as I in FIG. 48.
Figure 52:
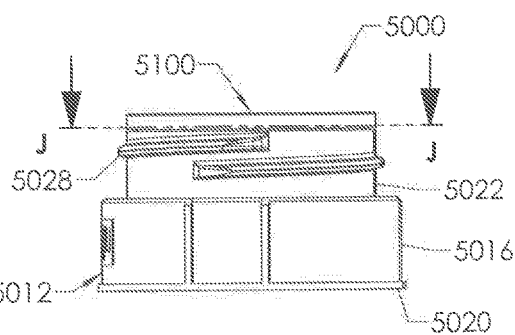
FIG. 52 is a side view of the sample container cap of FIG. 44.

Top portion 5100 also includes two slots 5190 in top surface 5102, each of which defines a space (or opening) that extends to top edge 5029 of bottom portion 5012 (as seen in FIGS. 47-49) when top portion 5100 and bottom portion 5012 are connected. Each slot 5190 forms a space between an outer wall 5101 and the body 5100B of top portion 5100. One or both slots 5190, and in this embodiment, both slots 5190 include an inward-facing extension 5101B (best seen in FIG. 61B). The outer wall 5101 includes a top 5101A and an inward-facing extension 5101B that has a chamfered end 5101C, as shown in FIGS. 47-48. A raised protrusion 5195A is in only one slot 5190 in this embodiment. Protrusion 5195A is configured to (1) align with and fit through indentation 5063, and (2) abut protrusions 5095A and 5095B.

Gasket

Figure 50:
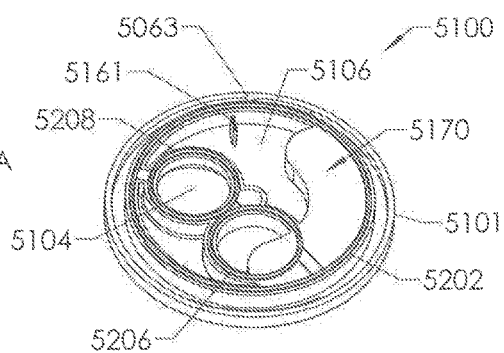
FIG. 50 is a bottom, perspective view of the top portion of the sample container cap of FIG. 44.
Figure 51:
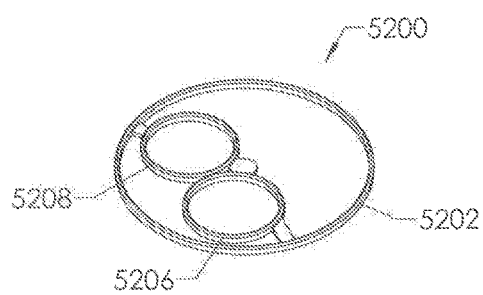
FIG. 51 is a bottom, perspective view of the sealing structure of the sample container cap of FIG. 44.

As best shown in FIGS. 50-51, gasket 5200 as shown is a one-piece structure and is preferably comprised of a compressible polymer material that is over-molded onto top portion 5100 although gasket 5200 may be an independent structure and/or more than one piece.

Gasket 5200 includes (1) an annular outer portion 5202 that rests on and presses against upper surface 5058 of bottom portion 5012, (2) a first annular 1206 configured to press against and slide across surface 5048 of plate 5043 and to seal between opening 5044 and top portion 5100 when cap 5000 is in a closed position, (3) a second annular seal 5208 that surrounds top opening 5104 and is configured to press against and slide across surface 5048 and to seal between top opening 5104 and top surface 5048 when cap 5000 is in a closed position.

Alternatively, the sealing function could be performed in part by an O-ring fitted to the outer diameter of the top portion 100. Another type of seal style that could be used is a "lip-seal" that would be over-molded to either the top portion 5100 or the bottom portion 5012.

Operation

Bottom portion 5012 is connected to top portion 5100 by first aligning the top portion and the bottom portion in any suitable manner, such as the one described with respect to cap 10 or cap 1000. In that case, indicia 5012A is aligned with an indicia (not shown) on top portion 5100 and then the two portions are pressed together until they engage to form assembled cap 5000.

Top portion 5100 may be properly aligned with bottom portion 5012 by alignment of indentation 5063 with projection 5195A in slot 5190, as shown, for example, in FIGS. 53, 53A and 59. In this embodiment, projection 5195A is only in one slot 5190 and indentation 5063 is only at one location on upper lip 5029 of bottom portion 5012, so top portion 5100 and bottom portion 5012 can only be pressed together at a single location.

When pressed together, as shown in FIGS. 48 and 49, outer wall 5101 is configured to flex outwards away from body 5100B, and inward-facing extension 5101B, which is shown as having chamfered end 5101C, of outer wall 5101 presses past chamfered end 5029A of upper lip 5029 and is received in groove 5300 of bottom portion 5012. In this manner top portion 5100 is attached to bottom portion 5012 and can rotate relative bottom portion 5012 and vice versa.

Because wall 5101 with inward-facing extension 5101B is only located at each of slots 5190, there is little friction between top portion 5100 and bottom portion 5012 allowing for relatively easy of rotation of bottom portion 5012 while top portion 5100 remains stationary, or vice versa. Alternatively, outer wall 5100 with an inward-facing extension 5101B may extend along a larger or lesser portion of top portion 5100. For example, there may be more than two slots 5190 of any suitable length with an outer wall 5101 and an inward-facing extension 5101B, or there may be only one slot 5190 of any suitable length with an outer wall 5190 and an inward-facing extension 5101B, or there may be more than two slots 5190 with an inward-facing projection 5190B.

When top portion 5100 and bottom portion 5012 are pressed together cap 5000 is in a first, closed position wherein top opening 5104 and bottom opening 5044 are not aligned and cap 5000 is not configured to allow fluid to pass therethrough. In this first, closed position, bottom opening seal 5208 covers bottom opening 5044 to seal between bottom opening 5044 and top portion 5100 (shown, for example, in FIG. 50). Top opening seal 5206 seals between top opening 5104 and top surface 5048 of plate 5043.

Further, when top portion 5100 and bottom portion 5012 are pressed together projection 5161 extends downward from bottom surface 5106 of top portion 5100 and fits into a slot in friction track 5090. When bottom portion 5012 is rotated while top portion 5100 remains stationary, or vice versa, the projection 5161 moves across (or in and out of) the indentations of friction track 5090 and the user feels a resistance and (preferably) hears a clicking sound.

Preferably, sample container 300 is connected to cap 5000 by screwing it into cavity 5030 with one or more threads 302 engaging one or more threads 5032. Then a security structure 1350, shown for example in FIG. 46, may be attached to cap 5000 and sample container 300. The security feature 1350 may be shrink-wrap plastic that covers part of the bottom portion 5012 and part of the sample container 300. The purpose of security structure 1350 is to prevent someone from removing the sample container 300 from cap 5000 prior to being in a laboratory for fluid testing. If security structure 1350 is removed or damaged when the cap 5000 with sample container 300 are received at a laboratory it indicates that the sample may have been contaminated after being taken.

A top closure 200 is preferably connected to cap 5000 and is preferably threaded onto one or more threads 5028. When attached, top closure 200 covers top portion 5100. A second security structure 1320, which may be shrink-wrap plastic, is preferably added and it covers at least part of top closure 200 and at least part of cap 5000. As shown, security structure 1320 may overlap security structure 1350, and the removal of security structure 1320 will not affect security structure 1350.

To attach cap 5000 to a housing 1, adapter 400, or other structure, security structure 1320 is removed, which exposes top closure 200. Then top closure 200 is removed from cap 5000. Cap 5000 is then threaded (or otherwise attached) to a housing 1 (as can be seen in FIGS. 66-73), adapter 400, or other structure by threading cap 5000 into a threaded cavity so that one or more threads 5028 mate with one or more threads in the cavity. Indicia, such as indicia 5012A, may align with indicia (not shown) on housing 1, adapter 400, or other structure, in order to assist in aligning the respective threads.

A stationary projection 5 (also referred to as a projection or protrusion that is received in channel 5140) in housing 1 or other structure is configured to be received in channel 5140 when cap 5000 is attached to housing 1, adapter 400, or other structure. Projection 5 has a first end 5A that is preferably curved or rounded in top (or plan) view and that has a first width. Projection 5 has a second end 5B that is preferably square or rectangular in top (or plan) view and that has a second width that is preferably greater than the first width.

As cap 5000 is threaded into housing 1 or other structure it moves upwards until projection 5 received in channel 5140 at first end 5140A. As cap 5000 continues to be threaded by rotating it (clockwise in this embodiment), channel 5140 moves, as shown for example in FIGS. 69 and 71, relative projection 5 so that projection 5 goes from its position at first end 5140A, through first end 5170A of insert 5170, through insert 5170, through end 5170B of insert 5170, and as the rotation of bottom portion continues, the first end 5A of projection 5 butts against second end 5140B of channel 5140, which prevents the further rotation of top portion 5100.

Then the further rotation of cap 5000 rotates only bottom portion 5012 because top portion 5100 is maintained in a fixed (or stationary) position by fixed-position projection 5.

Figure 71:
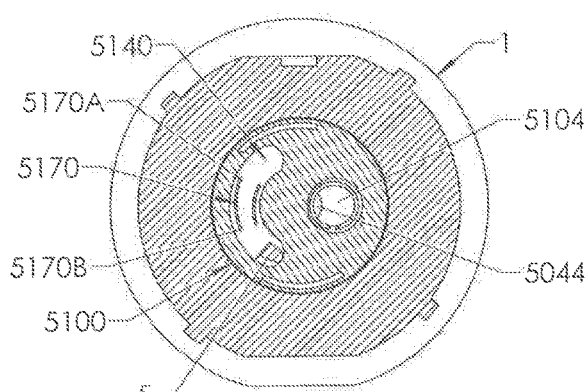
FIG. 71 is a cross-sectional view of the structure of FIG. 70 taken through line P-P.
Figure 72:
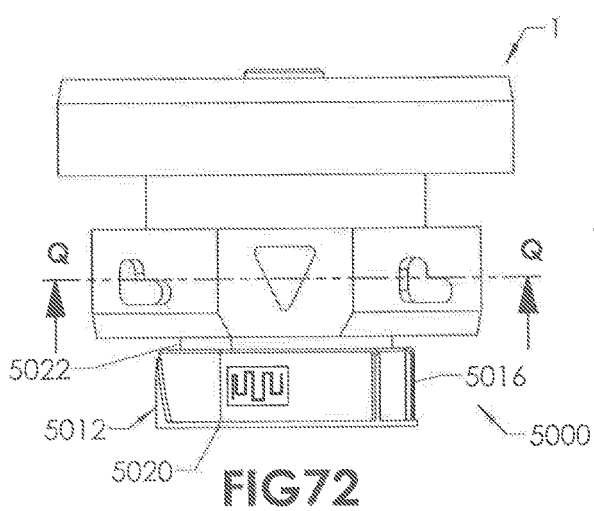
FIG. 72 is a side view of the structure of FIG. 66.
Figure 73:
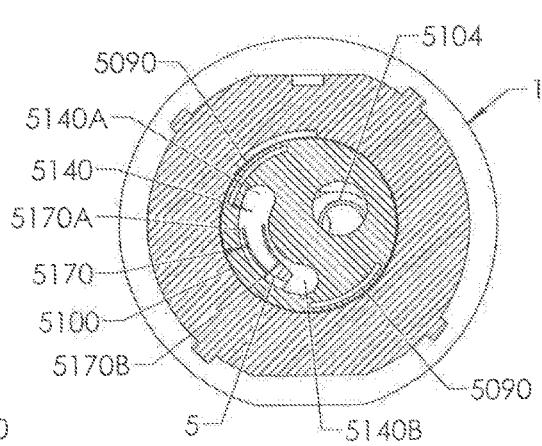
FIG. 73 is a cross-sectional view of the structure of FIG. 72 taken through line Q-Q.
Figure 74:
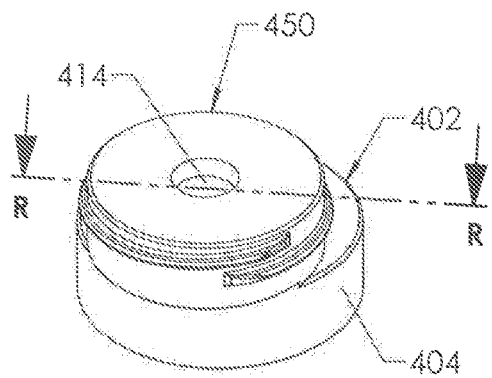
FIG. 74 is a top, perspective view of an adapter that may be used with a sample container cap.
Figure 75:
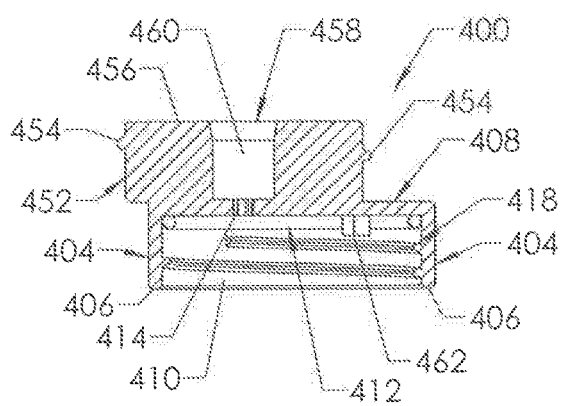
FIG. 75 is a side, cross-sectional view of the adapter of FIG. 74 taken through line R-R.
Figure 76:
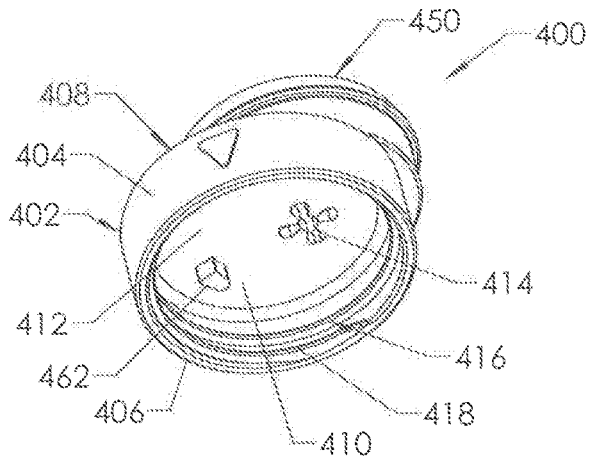
FIG. 76 is a bottom, perspective view of the adapter of FIG. 74.
Figure 77:
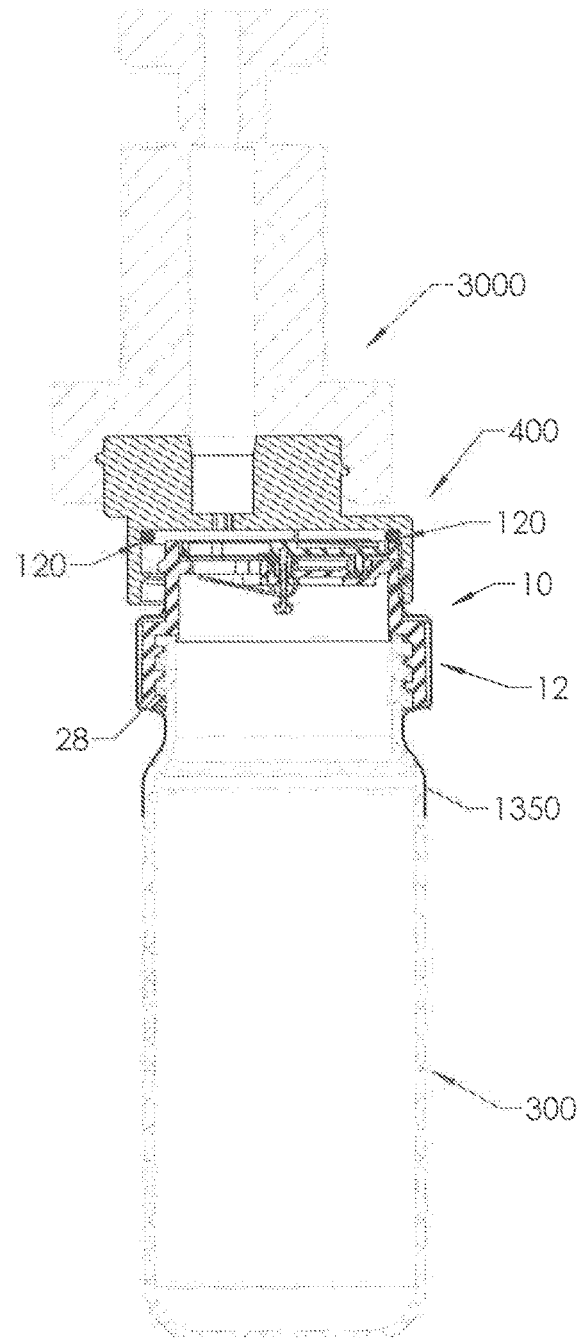
FIG. 77 is a side, cross-sectional view of a sample container cap connected to a sample container (shown in phantom) the adapter of FIG. 74 with the adapter further being connected to a hand pump (shown in phantom).
Figure 78:
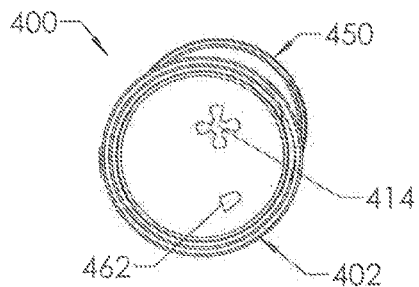
FIG. 78 is a bottom view of the adapter of FIG. 74.
Figure 79:
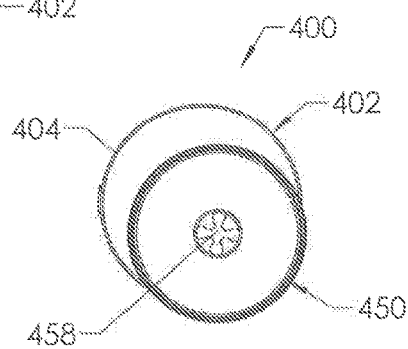
FIG. 79 is a top view of the adapter of FIG. 74.

Bottom portion 5012 rotates until bottom opening 5044 aligns with top opening 5104 (the openings need not be perfectly aligned) such that cap 5000 is in a second, open position, and is configured to have fluid pass through opening 5104 and bottom opening 5044, and into sample container 300. This position of cap 5000 is shown in FIG. 71. Fluid may flow through the openings in any suitable manner, such as being guided by a fluid transfer tube 2000 that is aligned with opening 5104, although any suitable structure or method for transferring fluid may be utilized.

Figure 57:
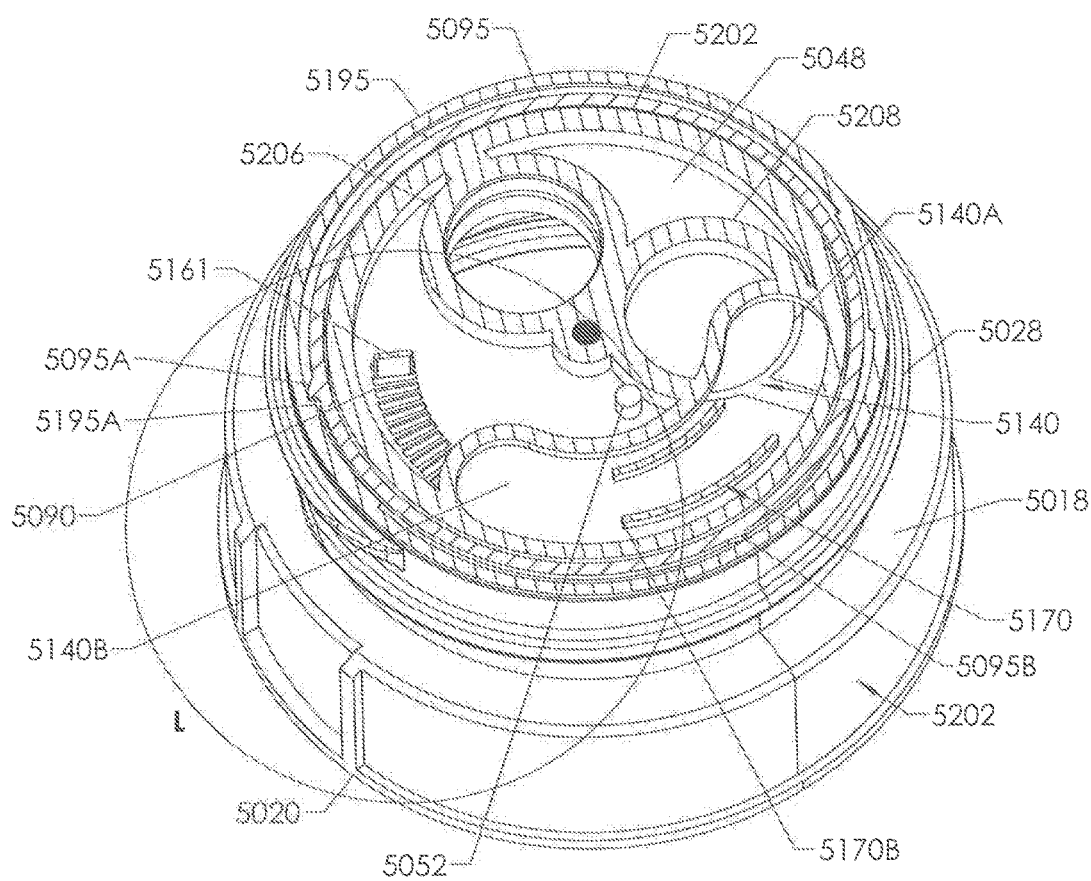
FIG. 57 is a top, cross-sectional view of the sample container of FIG. 56 taken through line J-J of FIG. 52.
Figure 58:
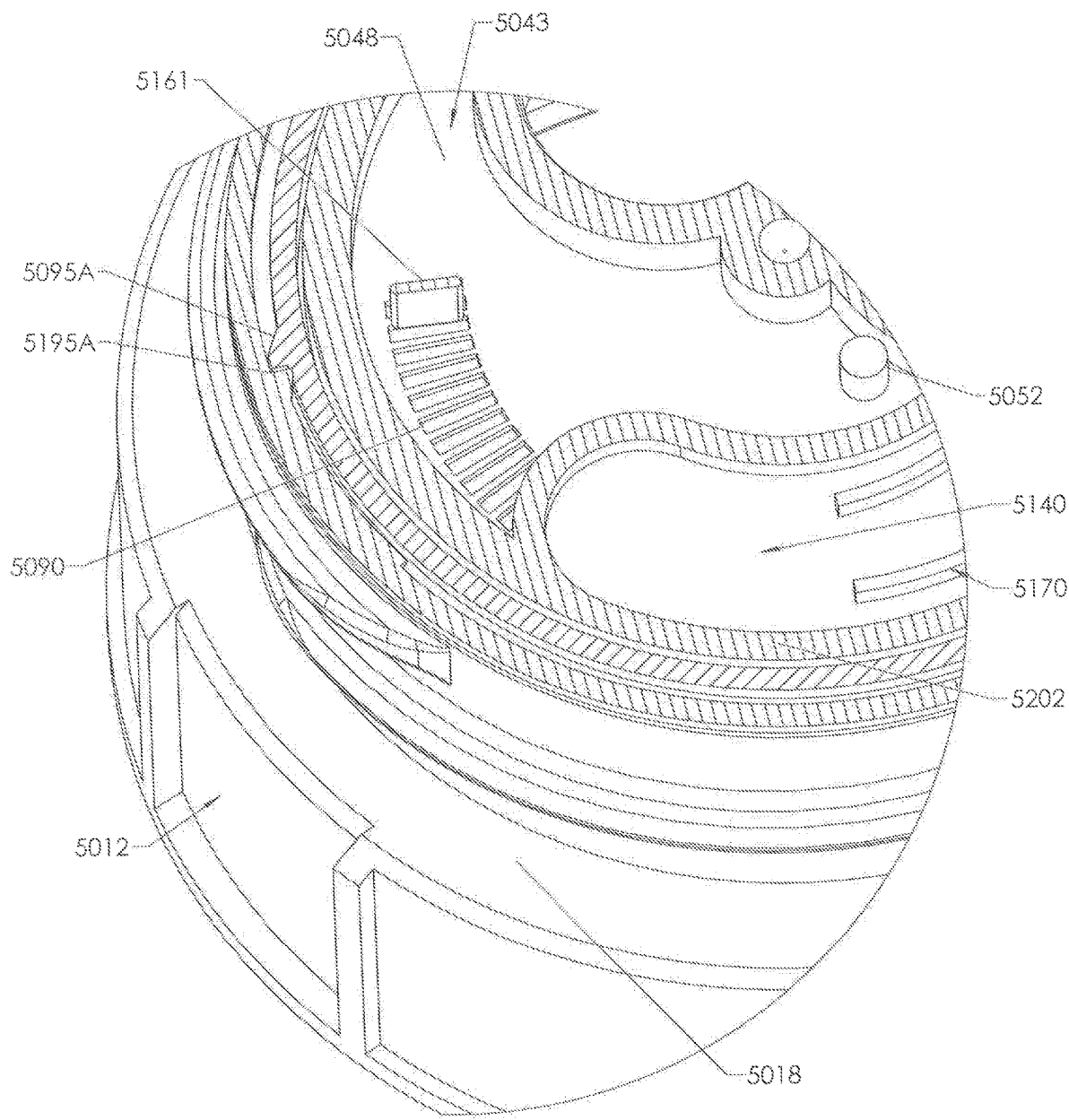
FIG. 58 is an enlarged view of the structure designated as L in FIG. 57.

To prevent further rotation of cap 5000 past the second, open position, two abutting structures, structure 5095A in groove 5300 and structure 5195A on top portion 5100 press against one another and prevent further rotation, as shown, for example, in FIGS. 57-58. Additionally, stop 5052 on top surface 5048 of plate 5043 abuts a rigid structure to which seal 5206 is attached to help prevent over rotation.

After a fluid sample is taken, cap 5000 is removed from the structure to which is attached.

When cap 5000 is removed it is unscrewed (counterclockwise in this embodiment), which causes cap 5000 to rotate and move downward. As cap 5000 is rotated and unscrewed, channel 5140 moves around projection 5 until projection 5 is at second end 5170B of insert 5170. Because the second end 5B of projection 5 is wider than first end 5A, and end 5B is preferably square or rectangular, and also because end 5170B of insert 5170 is narrower than first end 5170A (i.e., has a width that is less than the width of first end 5170A), the second end 5B of projection 5 butts against and stops at second end 5170B, which prevents further rotation of top portion 5100. As cap 5000 continues to be unscrewed, bottom portion 5012 rotates while portion 5100 remains stationary. This causes cap 5000 to move to (in this embodiment) a third, closed position different from the first, closed position. Further, when moved to the third, closed position projection 5195A slides over and past projection 5095B in groove 5300.

When in the third, closed position the top opening 5104 and the bottom opening 5044 do not align and cap 5000 is configured to not allow the passage of fluid or outside contaminants therethrough. In this position bottom opening seal 5208 surrounds bottom opening 5044 and seals between bottom opening 5044 and top portion 5100, and top opening seal 5206 surrounds top opening 5104 and seals between it and surface 5048 of plate 5043.

Over-rotation of bottom portion 5012 to cause cap 5000 to move past the third, closed position is unlikely because stop 5052 butts against (or touches) the rigid structure to which bottom opening seal 5208 is attached to prevent over rotation. Rotation back to the second, open position is prevented because when in the third, closed position protrusion 5195A has moved past protrusion 5095B in groove 5300 and cannot be moved back. A shown, each of these protrusions has an angled surface, wherein the respective angled surfaces and respective protrusions can slide past each other when moved in one direction. Each of protrusion 5195A and protrusion 5095B also has a vertical, planar surface opposite its angled surface. So, once the respective protrusions 5195A and 5095B slide past one another when cap 5000 is moved to its third, closed position, they then abut each other if an attempt is made to move cap 5000 back to the second, open position because the respective vertical surfaces of protrusion 5195A and 5095B cannot easily be moved past that one another. When in this third, closed position, shown, for example in FIGS. 59-61, cap 5000 is referred to as being locked.

As cap 5000 is further screwed out of the structure to which it was attached, the channel 5140 moves lower until it is lower than projection 5, which is then no longer in channel 1140. The cap 5000 with container 300 attached can then be removed, have top closure 200 attached, and be sent to a laboratory or other facility. At the laboratory the security structure 1350 is removed and the sample container 300 is unscrewed from bottom portion 5012 in order to access the sample fluid.

Embodiment 4

Turning now to FIGS. 82-108 an alternative fluid sample container cap (or "cap") 6000 is shown. Cap 6000 has a body 6012 and a shutter 6100 that connects to body 6012 and body 6012 and shutter 6100 can rotate relative each other unless shutter 6100 is held in a stationary position as described herein. One or more security (or tamper-resistant) structures 1300, such as structure 1320 and structure 1350 (shown, for example, in FIGS. 82 and 83), may be utilized to secure a top closure 200 to cap 6000 and/or secure container 300 to cap 6000. Security structure 1320 and security structure 1350 may be comprised of shrink-wrap plastic.

Body 6012 has a base 6014 and an upper portion 6016, which as shown are integrally formed together. Base 6014 has an annular outer surface 6018 with a recess 6020 formed therein. Recess 6020 may be used to engage a structure on a machine (not shown) to mechanically screw cap 6000 onto a container 300. Further, an RFID or other communication tag or label 15 may be on annular, outer surface 6018 or on any suitable position on cap 6000.

Body 6014 has an interior, annular wall 6022 with threads 6024 configured to receive and mate with threads on container 300 in order to secure cap 6000 to container 300. As used throughout this disclosure "threads" means one or more threads. A ledge 6015 is between base 6104 and upper portion 6106. Base 6014 has a top edge 6014A and a bottom edge 6014B. Top 6014A connects to or is integrally formed with ledge 6015. Bottom edge 6014B has is formed with bottom lip 6017.

The top portion 6016 of body 6012 is formed adjacent ledge 6015 and has threads 6030 formed in an outer annular surface 6030A. Threads 6030 are configured to mate with and connect to threads in a mounting structure 700 or 700A in a fluid dispensing device, such as a hand pump or automated fluid-dispensing unit. The top surface 6032 has an annular groove 6033, an outer lip 6036, an inner lip 6038, and an opening 6040.

Annular groove 6033 is positioned between outer lip 6036 and inner lip 6038. The purpose of annular groove 6033 is to provide a space for dust and dirt particles (i.e., debris) to reside when cap 6000 is attached to a mounting structure 700 or 700A of a fluid-dispensing device. Outer lip 6036 and inner lip 6038 are preferably configured to press against a bottom surface of mounting structure 700 or 700A of a fluid dispensing device when cap 6000 is connected to the mounting structure.

Base 6014 has an inner, annular wall 6024 that defines a cavity 6025, which is in communication with opening 6040 via openings 6072. Wall 6024 includes threads 6026 that are configured to mate with and connect to threads of a container 300 in order to secure the cap 6000 to container 300. Adjacent threads 6026 in cavity 6025 is an annular pocket 6029 that is configured to receive an O-ring or other seal on container 300 when cap 6000 is threaded onto container 300.

Alternatively, pocket 6029 may include an O-ring or other seal to seal against an upper lip of container 300.

Adjacent pocket 6029 is a reduced-diameter portion 6031 of cavity 6025. Reduced-diameter portion 6031 terminates at upper annular surface 6033. Reduced-diameter portion 6031 includes an annular interior wall 6035 that includes protrusions extending outward from annular interior wall 6035 and into reduced-portion 6031 of cavity 6025. There are two pairs of mated protrusions 6050, although there may be only one pair or may be more than two pairs. Thus, there are one or more pairs or at least one pair of mated protrusions 6050. Each of the pairs of mated protrusions 6050 as shown is 180° from the other pair. A space 6050A is defined between each respective pair of mated protrusions 6050. The purpose of the one or more pairs of protrusions 6050 and the space 6050A defined between each respective pair, is to receive projections 6112 on shutter 6100 in order to properly align shutter 6100 with body 6012 prior to initially pressing them together to form cap 6000. The proper alignment enables shutter 6100 and body 6012 to be pressed together so cap 6000 is in its first, closed position when initially assembled. In the first closed position, openings 6134 on the shutter 6100 do not align with openings 6072 on the body 6012 and fluid cannot readily pass through cap 6000.

Abutment protrusions 6052 as shown are taller (i.e., extend farther into reduced-portion 6031 of cavity 6025) than protrusions 6050 or tactile protrusions (if used). As shown, there are two abutment protrusions 6052 that are 180° apart. The purpose of abutment protrusions 6052 is to allow projections 6118 on shutter 6100 to move past them in one direction and to prevent projections 6118 from moving back in the opposite direction because stops 6118A prevent projections 6118 from moving back past abutment protrusions 6052. This assists in locking cap 6000 in its third, closed and locked position, as explained further below.

Tactile protrusions (not shown) are lower than abutment protrusions 6052 and as if used are preferably the same height as mating protrusions 6050. Tactile protrusions enable extensions and projections on shutter 6100 to move across them to provide a tactile sensation as the base 6012 is turned relative the shutter 6100. As this happens, the extensions 6112 and projections 6118 on shutter 6100 move across the tactile protrusions and cause a tactile sensation of movement plus an optional clicking sound. Tactile protrusions may or may not be used.

In the center of reduced-diameter portion 6031 is a connecting component 6070 that is configured to connect to shutter 6100 and that defines two body openings 6072 configured to align with shutter openings 6134 when the cap 6000 is in its second, open position and permit the passage of fluid therethrough and into cavity 6025, from where it passes into container 300. Although two openings 6072 are shown there could be only one opening 6072 or more than two openings 6072. Thus, there are one or more openings 6072, or at least one opening, 6072. As shown each opening 6072 is directly across from the other opening 6072. Two walls 6076 help define openings 6072 and extend outwards from upper annular surface 6033 and into cavity 6025. Although two walls 6076 are shown there could be only one wall 6076 or more than two walls 6076. Thus, there are one or more walls 6076, or at least one wall, 6076. As shown each wall 6076 is directly across from the other wall 6076. Walls 6076 can be of any suitable thickness, size, or shape. One or more walls 6076 are configured to mate with shutter openings 6134 when the cap 6000 is in its first, closed position, or in its third, closed and locked position.

A clasp 6078 is formed at the respective ends 6076A of respective legs 6077. Each clasp 6078 may be integrally formed with second ends 6076A or connected to them. Each clasp 6078 is configured to connect to shutter 6100, retain it at least partially inside of cavity 6025, and permit shutter 6100 to rotate relative body 6012 or vice versa. Each leg 6077 extends downward at an outward angle of about 3°-20° although any suitable angle may be utilized.

Shutter

Shutter 6100 has a top rim 6110 that includes two retention structures 6114, and two rotation-resistant structures 6116. Although two retention structures 6114 and two rotation-resistant structures 6116 are shown, there may be only one, or more than two, retention structures 6114 and only one, or more than two, one rotation-resistant structures 6116. Thus, there is at least one, or one or more, retention structures 6114, and at least one, or one or more, rotation-resistant structures 6116. Each of retention structures 6114 is formed into rim 6110 and includes a first end 6114A, a second end 6114B, and an elongated opening 6114C. As shown, each retention structure 6114 has the same size and shape and the centers of the two structures 6114 are spaced 180° from each other. A projection 6112 is formed at approximately the center of the outer wall of each retention structure 6114. Each projection 6112 is configured to fit in and slide into spaces 6050A of body 6012 in order to properly align shutter 6100 with body 6012 when the two are first connected and are in the first, closed position, shown, for example, in FIGS. 86-87.

Rotation-resistant structures 6116 each have a leg 6117 having a first end 6116A and a projection 6118 having a stop 6118A. A space 6116C separates leg 6117 from the inner surface of top edge 6110. Second ends (or projections) 6118 including stops 6018A are configured to move across tactile projections (not shown) when body 6012 is connected to shutter 6100 and rotated relative shutter 6100. After cap 6000 is moved to its third, closed and locked position, stops 6018A engage abutment protrusions 6052, which is shown, for example, in FIGS. 90-91, to prevent the rotation of cap 6000 back to the second, open position if counter-rotation is attempted.

Top opening 6122 leads to a cavity 6130 that leads to a passage 6126 in lower shutter body 6150. Passage 6126 includes a rim 6128 below which passage 6126 has a larger diameter. Clasps 6078 of body 6012 grasp engage rim 6028 when shutter 6100 is attached to base 6012. Opening 6122, shutter openings 6134, and passage 6126 allows for the passage of fluid therethrough when cap 6000 is in the second, open position, which is shown, for example, in FIGS. 88-89.

Cavity 6130 is conically shaped, although it could be of any suitable shape, and has two inner walls 6132, two shutter openings 6134, and two flanges 6136 extending outward from inner walls 6132. As shown, there are two shutter openings 6134, although there could be only one shutter opening 6134 or more than two shutter openings 6134. Thus, there are one or more shutter openings 6134 or at least one shutter opening 6134. Each shutter opening 6134 has ribs 6138 surrounding it, which preferably receive a soft, rubber over mold as shown FIGS. 100 and 100A to seal against walls 6070 of base 6012 when cap 6000 is in the first, closed position (shown, for example, in FIGS. 86-87), or in the third, closed and locked position (shown, for example, in FIGS. 90-91), in order to create a seal. There need not be, however, an over mold or other secondary sealing structure.

The cap as described and claimed herein includes both a cap with an over mold or other secondary sealing structure, and a cap without it. Each shutter opening 6134 may also have outer support ribs 6152, which help to provide support to the shutter windows 6134, although supports 6152 need not be utilized.

As shown, there are two flanges 6136, although there could be only one flange 6136 or more than two flanges 6136. Thus, there are one or more flanges 6136 or at least one flange 6136. Each flange 6136 extends through a body opening 6072 when cap 6000 is assembled. One or more flanges 6136 contact respective stems on the mounting structure 700 to which cap 6000 is connected, which prevents the rotation of shutter 6100 in response.

Over Mold

Figure 100:
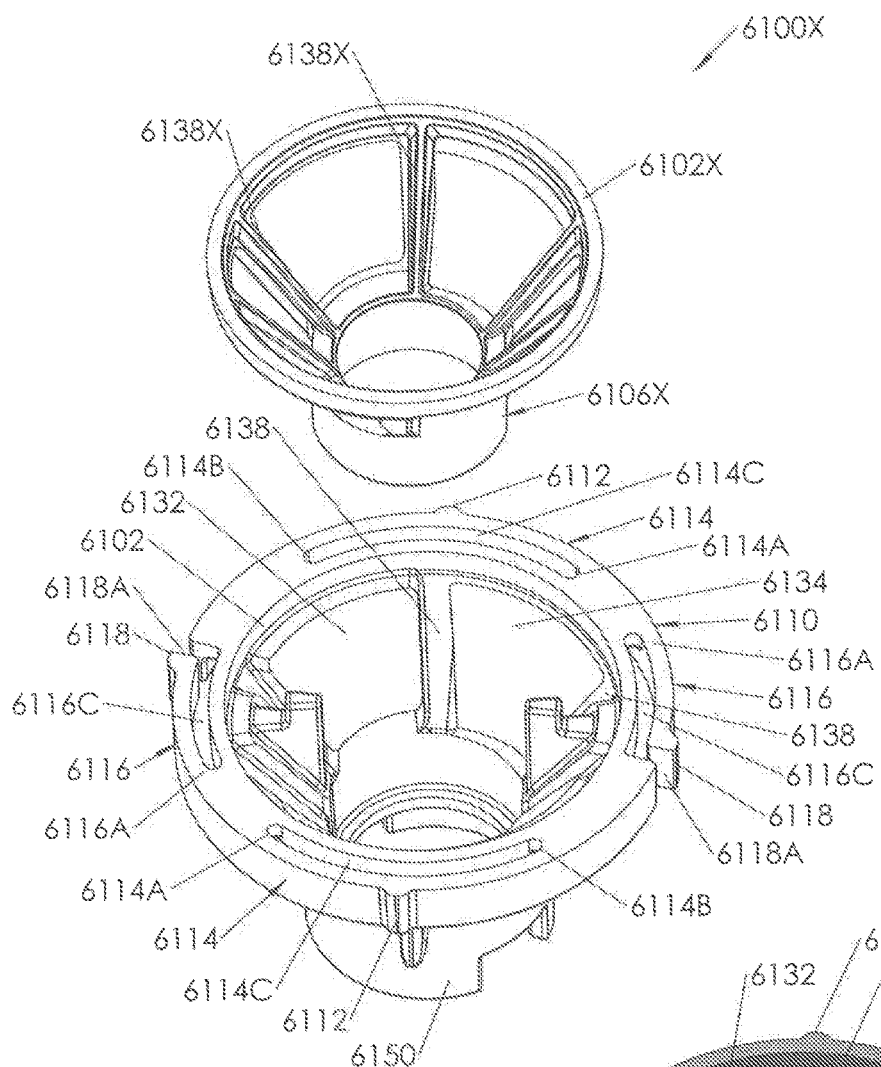
FIG. 100 is an exploded, top perspective view of the shutter of FIG. 84 showing a shutter over mold and a shutter base.
Figure 100A:
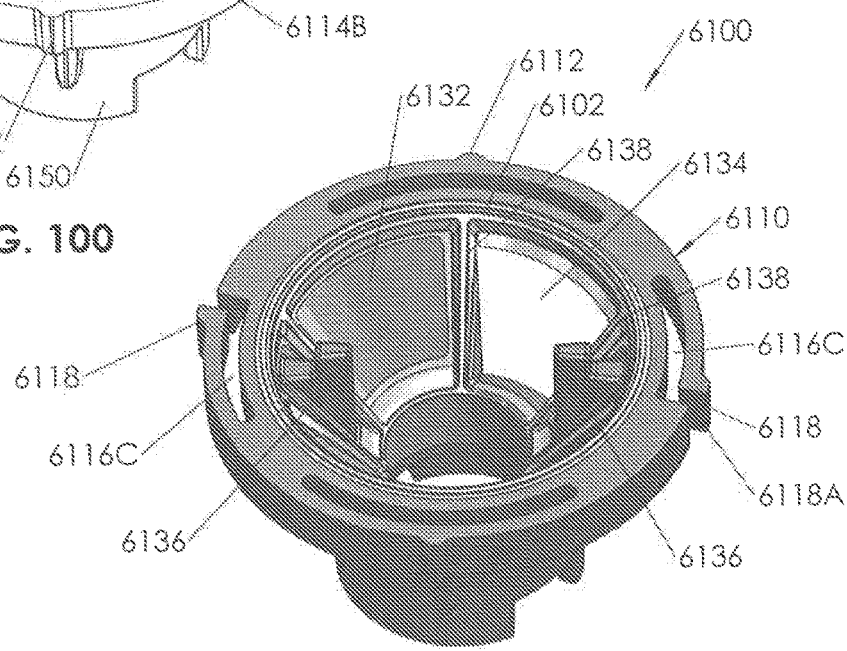
FIG. 100A is a top perspective view of the shutter of FIG. 84 or 100 showing the shutter over mold attached to the shutter base.
Figure 101:
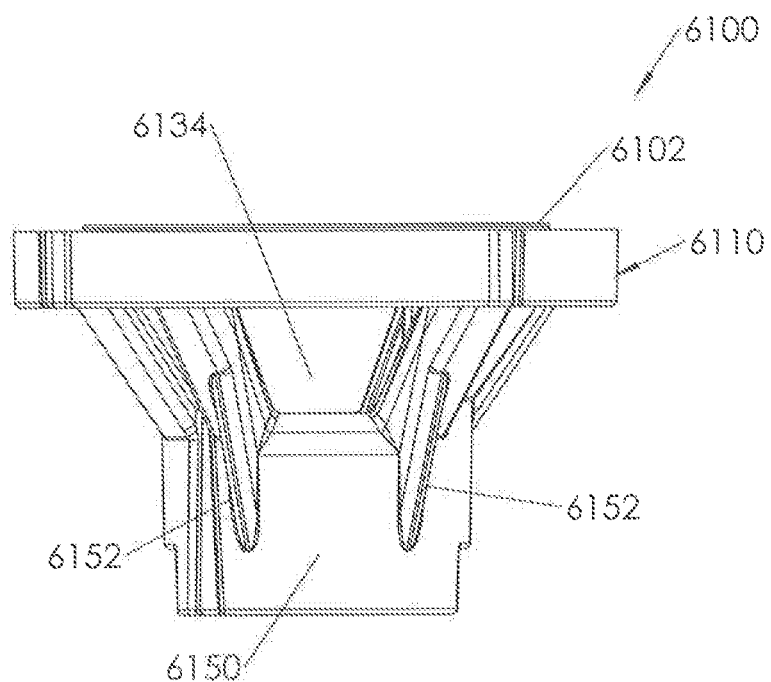
FIG. 101 is a side view of the shutter of FIG. 98.
Figure 102:
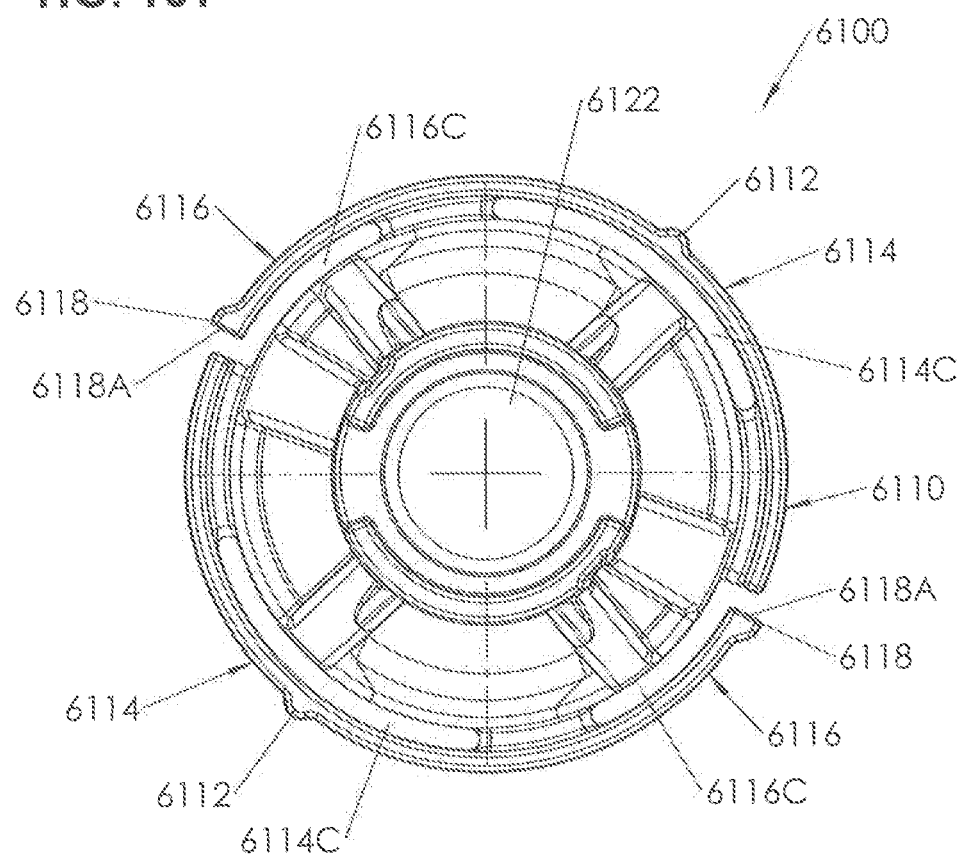
FIG. 102 is a bottom view of the shutter of FIG. 98.
Figure 103:
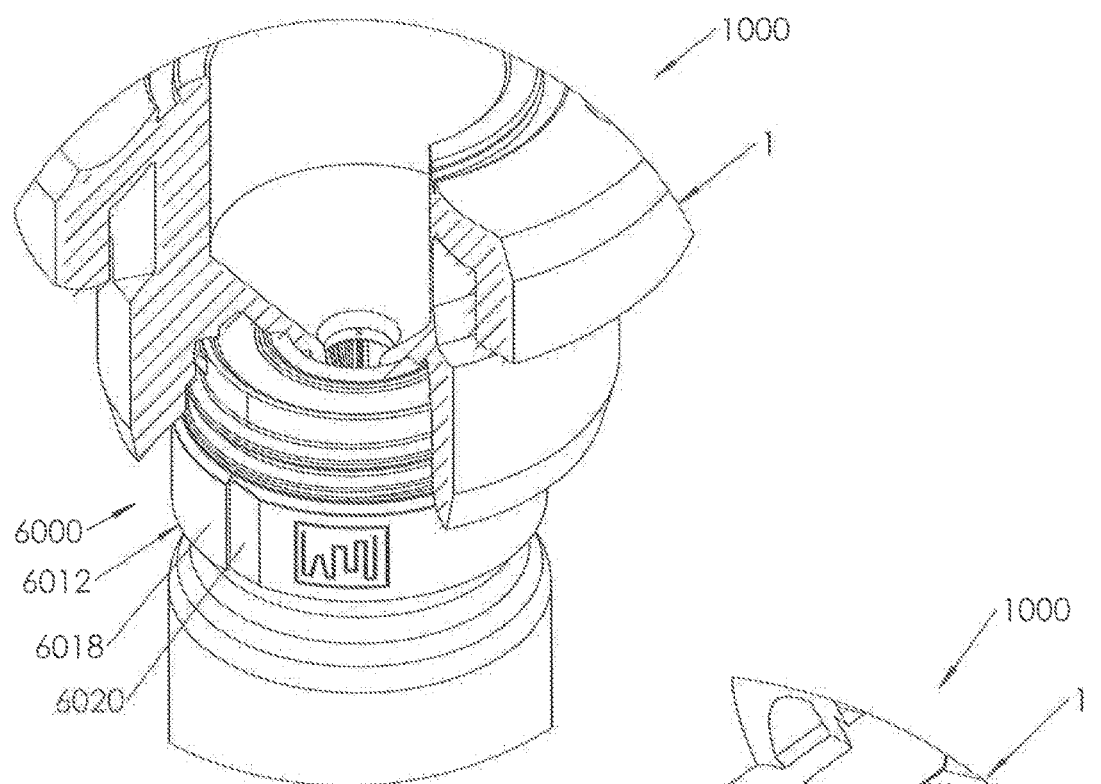
FIG. 103 is a partial cut-away, side perspective, view of a cap mounted to a sample container and to a view of the device of FIG. 83 connected to a mounting structure of a fluid-dispensing device.
Figure 104:
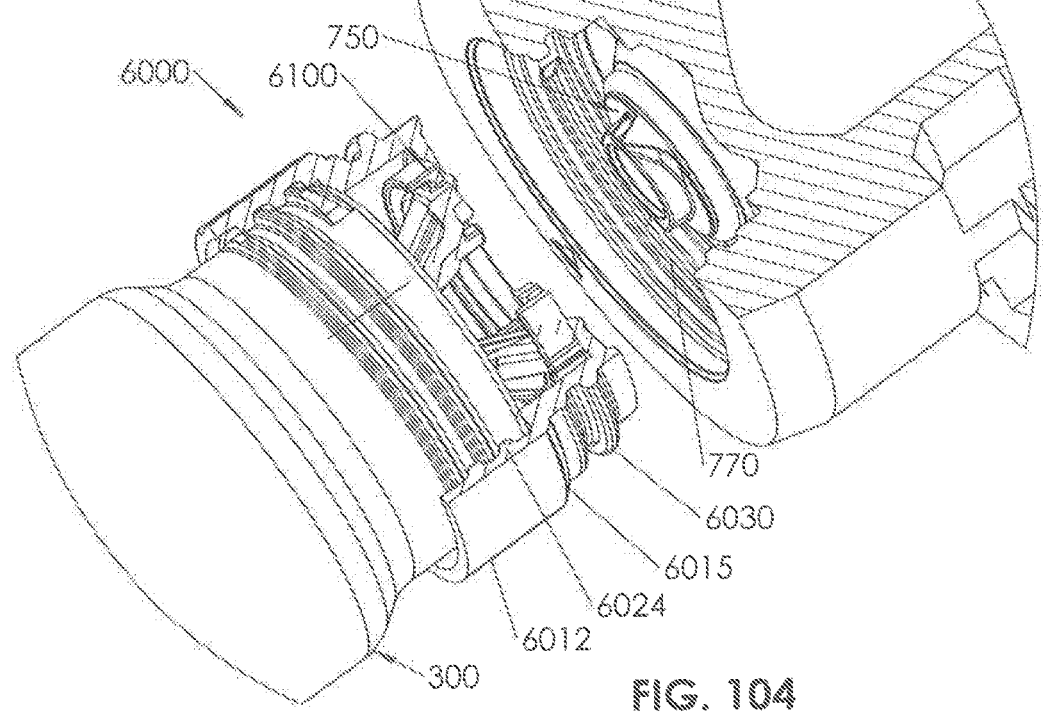
FIG. 104 is a closeup partial cutaway, partial cross-sectional, side view of the device and mounting structure of FIG. 103.
Figure 105:
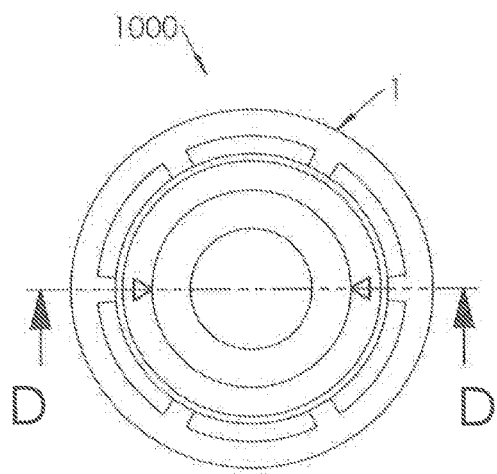
FIG. 105 is a top view of the structure of FIG. 103.
Figure 106:
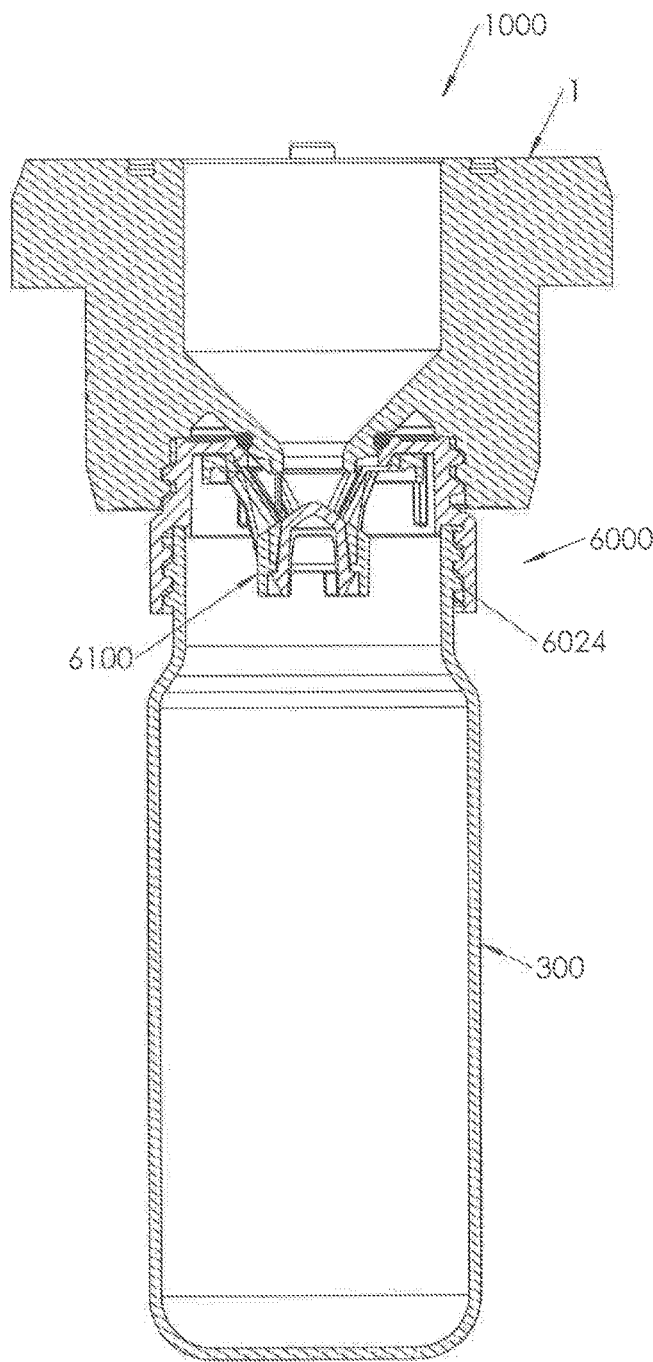
FIG. 106 is a side, cross-sectional view of the structure of FIG. 105 taken through line D-D.

The shutter 6100 may have an a softer durometer over mold 6100X, shown in FIGS. 100 and 100A. If an over mold or other softer, sealing material is applied to shutter 6100, it is applied to or forms ribs 6138 that partially or totally surround shutter openings 6134 in order to form a seal against walls 6076 of body 6012 when cap 6000 is in the first, closed position (shown, for example, in FIGS. 86-87) or the third, closed and locked position (shown, for example, in FIGS. 90-92). The softer material may also be applied or form upper, inner lip 6102 to seal against upper, annular surface 6033 of reduced-diameter portion 6031. Depending on manufacturing requirements or design choices softer material may be applied to other locations on shutter 6100.

The shutter over mold 6100X shown in FIG. 100 has a top rim 6102X that forms all or part of shutter upper lip 6102, shutter opening rims 6138X that form all or part of shutter opening rims 6138, and a base 6106X that can fit inside of passage 6126.

Mounting Structure

Figure 113:
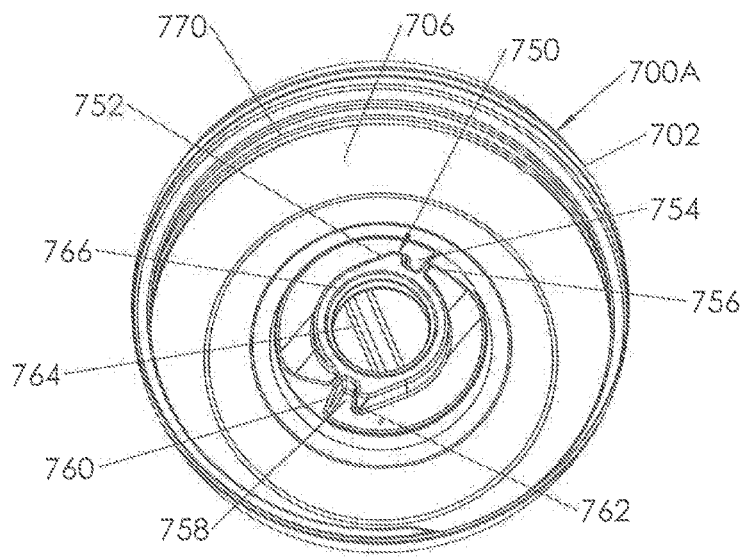
FIG. 113 is a perspective, bottom view of the mounting structure of FIG. 109.
Figure 114:
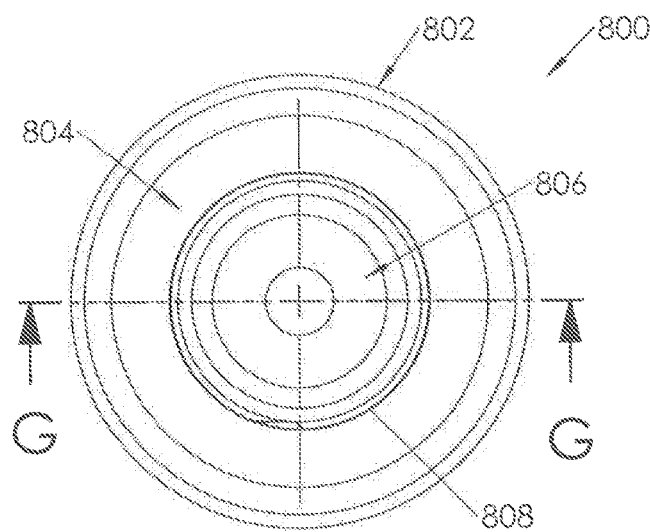
FIG. 114 is a top view of an adapter closure shown in FIG. 107.
Figure 116:
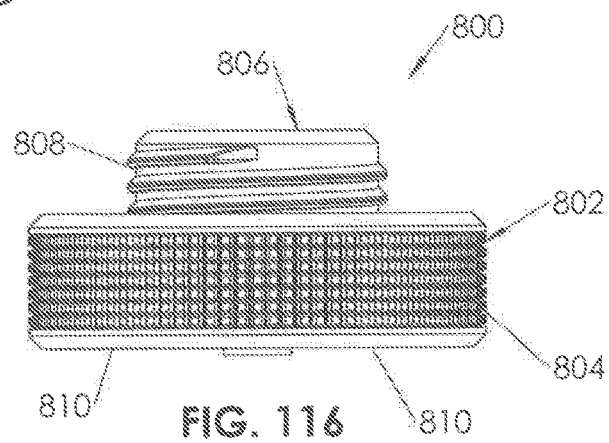
Figure 115:
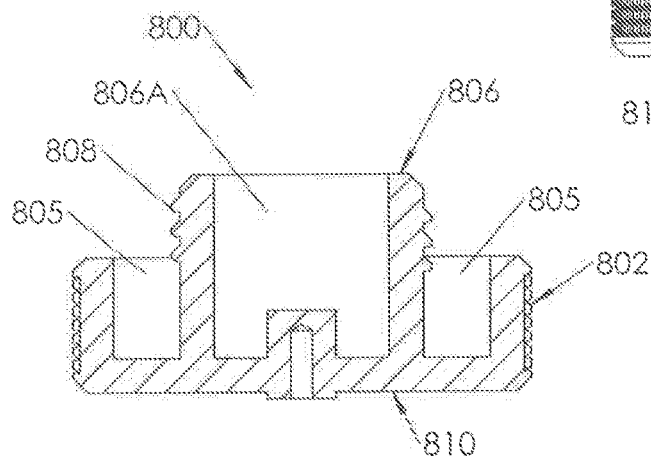
FIG. 115 is a side, cross-sectional view of the adapter closure of FIG. 114 taken through line G-G.
Figure 117:
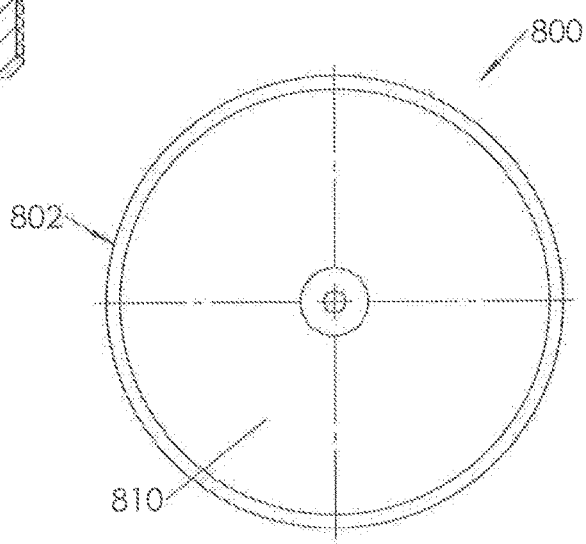

FIGS. 107-113 show mounting structures 700 and 700A, which have the same internal structure for engaging cap 600. Mounting structure 700A is especially configured to be connected to a hand pump, such as hand pump 3000, shown in FIGS. 107-108. Mounting structure 700 is used with a device such as an automatic fluid dispenser 1 in a system 1000, wherein the automatic fluid dispenser 1 can be attached directly to a machine from which a fluid sample is to be taken. Mounting structure 700A is screwed into a threaded collar 3002 of hand pump 3000. The internal, bottom components of mounting structure 700A is best seen in FIG. 113 so mounting structure 700A, which is shown in FIGS. 107-113, will be described herein in detail. Mounting structure 700 has the same internal, bottom components.

Turning now to FIGS. 109-113, mounting structure 700A is shown not connected to hand pump 3000. Mounting structure 700A has a side 702 with an annular side surface 704. Mounting structure 700A has a top surface 708, a threaded stem 710 with outer threads 712, a top opening 710A, a bottom opening 764, and a passage 710B through which fluid from hand pump 3000 can pass through and into a container 300. Outer threads 712 are configured to connect to the threads of a fluid-dispensing device.

Figure 107:
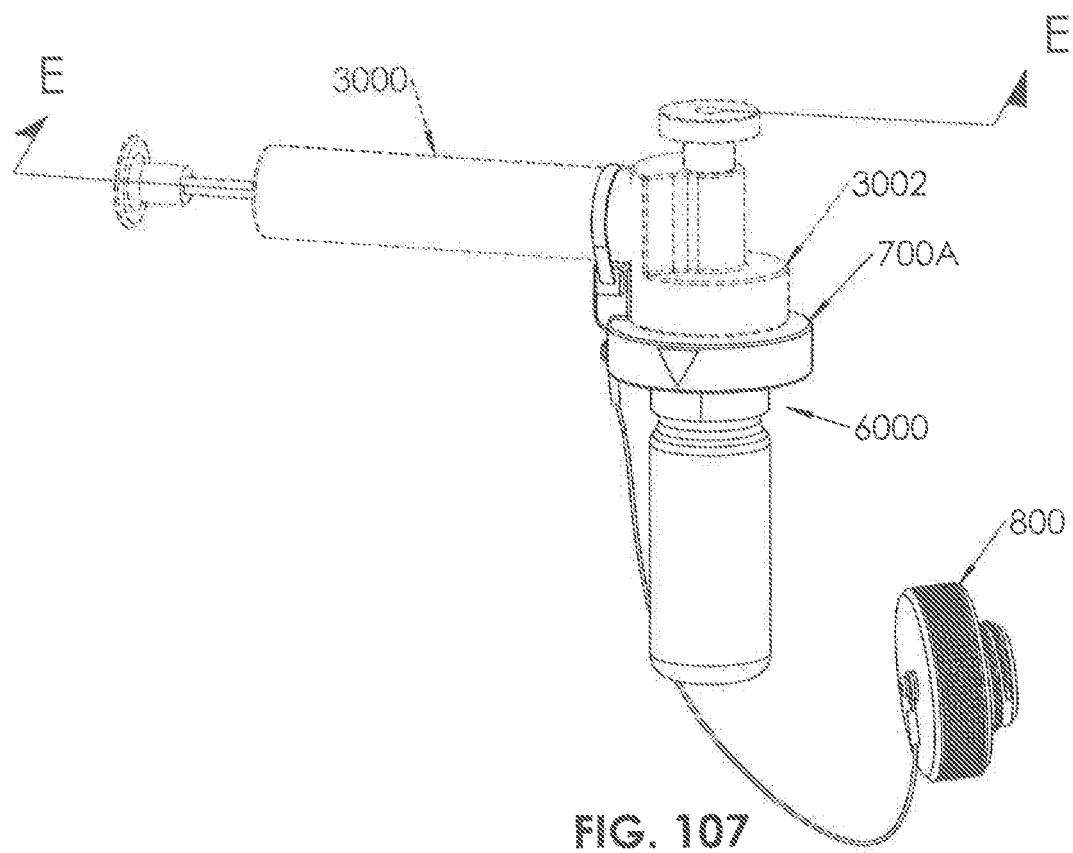
FIG. 107 is a side, perspective view of a cap mounted to a sample container and to a hand-pump mounting structure with the hand pump shown in phantom.
Figure 108:
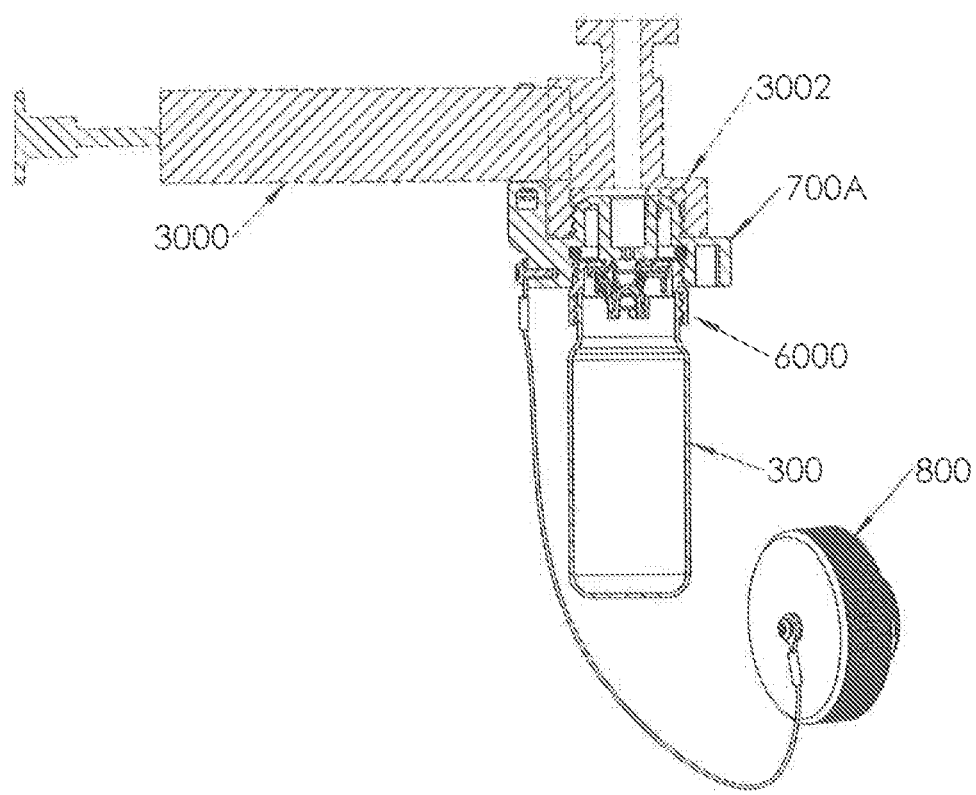
FIG. 108 is a side, cross-sectional view of the structure of FIG. 107 taken through line E-E.
Figure 109:
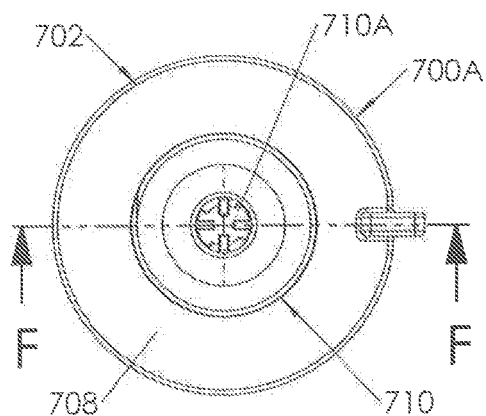
FIG. 109 is a top view of the mounting structure shown in FIG. 107.
Figure 111:
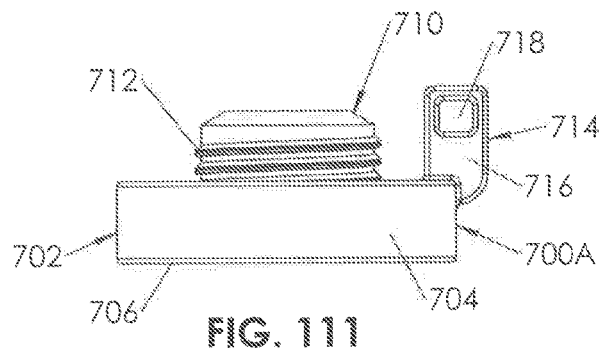
FIG. 111 is a side view of the mounting structure of FIG. 109.
Figure 110:
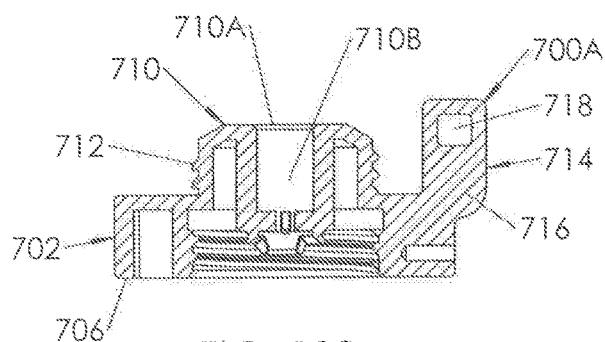
FIG. 110 is a cross-sectional, side view of the mounting structure of FIG. 109 taken through line F-F.
Figure 112:
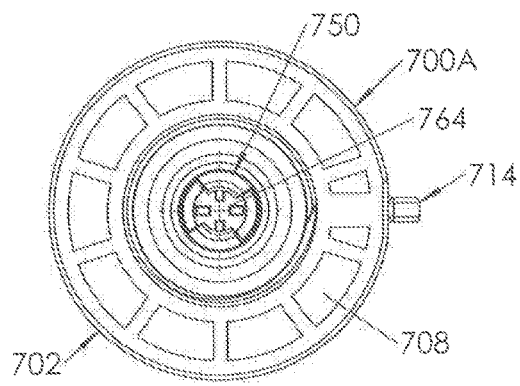
FIG. 112 is a bottom view of the mounting structure of FIG. 109.

Mounting structure 700A has a bottom surface 706 and an anti-rotational flange 714 having a flange body 716 and a flange opening 718. As best seen in FIG. 107, anti-rotational flange 714 is adjacent hand pump 3000 when cap 6000 is attached to mounting structure 700A and a retainer, such as a zip tie, is wrapped around the body of hand pump 3000 and through flange opening 718. This helps prevent mounting structure 700A from unthreading from collar 3002 when cap 6000 is unthreaded from mounting structure 700A.

Turning to FIG. 113, the internal structure of the bottom of mounting structure 700A, which is the same as the internal structure of mounting structure 700, is shown. Inner threads 770 are configured to receive threads 6030 of cap 6000 in order to secure cap 6000 to mounting structure 700A. Surface 706 is generally flat and leads to a cap mount 752, which has a first stem 756, a third stem 750, a first pocket 754, a second stem 762, a fourth stem 760, and a second pocket 758.

Operation

Shutter 6100 is first connected to body 6012 by aligning projections 6112 with spaces (or slots) 6050A and then pressing shutter 6100 and body 6012 together. Connecting component 6070 is pushed through passage 6126 and clasps 6078 move into passage 6126. Legs 6077 of connecting component 6070 are each formed at an outward angle and are thus biased outwards so clasps 6078 snap or move outward past the rim 6128 in passage 6126 to engage the bottom of rim 6128 and retain shutter 6100 in base 6012. The cap 6000 is then in its first, closed position (shown, for example, in FIGS. 86-87) and ready for use. In this position, the shutter openings 6134 are aligned with body walls 6076 and ribs 6138 seal against walls 6076 so fluid cannot readily pass through the cap 6000.

If utilized, the soft portion 6138X of over mold 6100X that forms all or part of rims 6138 of shutter openings 6134, helps to form a tight seal against walls 6076. Further the portion 6102X of over mold 6100X at the top 6102 of the shutter 6100 helps to seal against upper annular surface 6033 of body 6012.

Then, preferably, top closure 200 is attached to threads 6030 of cap 6000. Container 300 is attached to internal threads 6024 of cap 6000. Security structure 1300, comprising portions 1320 and 1350, is then attached to secure top closure 200 and container 300 to cap 6000.

To attach the cap 6000 to a mounting structure 700 or 700A in a fluid-dispensing device (such as a housing or hand pump), the top portion 1320 of the security structure and the top closure 200 are removed from cap 6000. Then the cap 6000 is threaded onto the mounting structure 700 or 700A with threads 6030 engaging threads 770. As it is threaded the cap 6000 moves upwards until the opening 6040 of body 6012 receives mount 750 and a first flange 6136 rides over third stem 752, is received in pocket 754, and contacts first flange 756. Simultaneously, a second stem 6136 rides over fourth stem 762, into pocket 758, and contacts second stem 760. This contact and engagement of respective flanges 6136 with the first stem 756 and the second stem 760 prevents the shutter 6100 from moving and the body 6012 continues to rotate until the cap 6000 is fully tightened on the mounting structure 700 or 700A. As the body 6012 rotates while the shutter 6100 remains stationary, the cap 6000 moves from its first, closed position to a second, open position (shown, for example, in FIGS. 88-89) in which the one or more shutter openings 6134 align with the one or more body openings 6072 and permit the passage of fluid through the cap 6000 and into the container 300. As shown, for example, in FIG. 89, when in the second position, each of the stops 6118A of projections 6118 are in contact with one of the respective mating abutments 6050.

Once a fluid sample is collected inside of the container 300, the cap 6000 is unscrewed from the mounting structure 700 or 700A, which causes the cap 6000 to move from the second, open position to a third, closed and locked position. As the cap 6000 is unscrewed the first flange 6136 moves away from the first stem 756 and contacts third stem 752, and the second flange 6136 moves away from the second stem 760 and contacts fourth stem 762, which holds shutter 6100 stationary and prevents it from rotating farther in the closing direction. A side 6072A of each opening 6072 in the body 6012 contacts each flange 6136.

As cap 6000 continues to be loosened it lowers and is no longer in contact with mount 750. The engagement of body opening sides 6072A with respective flanges 6136, however, causes the shutter 6100 and body 6012 to move together in the loosening direction. Further, as the respective shutter flanges 6136 moved from the first stem 756 to the third stem 7052, and from the second stem 760 to the fourth stem 762, the one or more shutter openings 6134 moved and are no longer aligned with the one or more body openings 6072 and are instead aligned with body walls 6076, so fluid cannot readily pass through the cap 6000.

Additionally, as the cap 6000 is unscrewed, the one or more projections 6118 each move past an abutment protrusion 6052 inside of the body 6012, and the respective shapes of the one or more stops 6118A and abutment protrusions 6052 prevent the stops 6118A and projections 6118 from moving back in the opposite direction (the tightening direction). This prevents movement of the body 6012 relative the shutter 6100 in the tightening direction.

Hence, the cap 6000 is closed and locked because the respective one or more shutter openings 6134 and body openings 6072 are not aligned, and the shutter 6100 and body 6012 cannot move (in any significant amount) relative each other in either the tightening direction or the loosening direction without breaking cap 6000.

Once the cap 6000 is unscrewed from the mounting structure 700 or 700A the top closure 200 is preferably screwed onto threads 6030 of body 6012. The container 300 with cap 6000 on it and top closure 200 on the cap 6000 is then sent to a laboratory or similar facility. The top closure 200 and security structure 1350 can be removed, and cap 600 is unscrewed from container 300 to access the fluid sample inside.

Adapter Closure

FIGS. 114-117 show a hand-pump closure 800. Closure 800 is any suitable structure for sealing the collar 3002 when a cap is not attached to it. Closure 800 has an annular side 802 with a side surface 805, a top surface 804, and a bottom surface 810. Closure 800 has a threaded stem 806 with threads 808 that are configured to be received in a threaded opening of collar 3002.

Top Closure

Top closure 200 is preferably comprised of plastic or metal but can be comprised of any suitable material and be of any configuration suitable to connect to and seal cap 10, cap 1000, or cap 5000. Top closure 200 as shown has a top surface 201, an annular side surface 202 with (in this embodiment) alternating ridges 204 and grooves 206 to permit users to better grip top closure 200, a bottom edge 208, and an internal cavity (not shown) with one or more threads that mate with one or more threads 28, 1028, or 5028 when top closure is attached to one of the caps 10, 1000, or 5000.

Adapter

Turning now to FIGS. 74-79, cap 10, or cap 1000, or cap 5000 could be used with an adaptor 400 configured so that the cap 10, cap 1000, or cap 5000 could be utilized with a hand-operated fluid extraction device 3000, the structure of which is known to those skilled in the art.

Adapter 400 has a first section 402 configured to be connected to cap 10 and a second section 450 configured to be connected to hand-operated fluid extraction device 3000. First section 402 has an outer annular surface 404, a bottom edge 406, and outer ledge 408, and an inner cavity 410. Inner cavity 410 has an upper surface 412 with an opening 414, and an inner annular wall 416 with threads 418. Threads 418 are configured to receive threads 28 of cap 10.

Second section 450 has an outer annular wall 452 having a thread 454 that is configured to be received in an opening of hand-operated fluid extraction device 3000. Second section 450 further comprises a top 456 and an opening 458 that leads to a passageway 460, and a stem 462.

Adapter 400 may also include a stationary projection, such as stationary projection 5, to be received in a channel such as channel 1140 or channel 5140.

Communications

Turning now to FIG. 81, a cap 10, cap 1000, or cap 5000 may include a radio frequency identification (RFID) tag or label 15 to identify the cap and fluid sample. Alternatively or additionally, an RFID label or tag may be attached to sample container 300. As shown in FIG. 81, any suitable device such as a housing 1, computer or portable electronic device 11, adapter 400, and/or a hand pump 3000 may communicate with the RFID tag.

Container

Sample container 300 has one or more threads 302, a body 308, and a top opening 306. One or more threads 302 are configured to mate with threads 28, 1028, or 5028 on bottom portion 12, 1012, or 5012, so container 300 can be screwed onto bottom portion 12, 1012, or 5012. An outer, protective covering (not shown), such as a metal container or mesh, may cover and protect sample container 300.

Some non-limiting examples of this disclosure follow:

Example 1: A sample container cap comprising: (a) a bottom portion having a top surface, a bottom cavity, and a bottom opening configured to permit fluid to flow therethrough; and (b) a top portion connected to the bottom portion, wherein the top portion has a channel and a top opening configured to permit fluid to flow therethrough; wherein the cap has (c) a first position in which the bottom opening and the top opening are not aligned and the cap is not configured to permit the passage of fluid therethrough, and (d) a second position in which a stationary projection is positioned in the channel and the bottom opening and top opening are aligned and the cap is configured to permit the passage of fluid therethrough.

Example 2: The sample container cap of example 1 that further includes a third position in which the stationary projection is positioned in the channel and the bottom opening and the top opening are not aligned and the cap is not configured to permit the passage of fluid therethrough.

Example 3: The sample container cap of any one of examples 1 or 2, wherein the top portion has a top surface and the channel is in the top surface.

Example 4: The sample container cap of any one of examples 1-3, wherein the channel includes an insert positioned therein.

Example 5: The sample container cap of example 4, wherein the channel has a first end and a second end.

Example 6: The sample container cap of any one of examples 4 or 5, wherein the insert has a first end having a first width and a second end having a second width, wherein the second width is less the first width.

Example 7: The sample container cap of any one of examples 1-6, wherein the stationary projection has a first end having a first projection width and a second end having a second projection width, wherein the second projection width is greater than the first projection width.

Example 8: The sample container cap of example 7, wherein the second projection width is greater than the second channel width.

Example 9: The sample container cap of any one of examples 7 or 8, wherein the first projection width is less than the first channel width and less than the second channel width.

Example 10: The sample container cap of any one of examples 1-9, wherein the bottom portion and top portion are configured to rotate relative one another.

Example 11: The sample container cap of any one of examples 1-10, wherein the bottom portion is configured to be in the first position before the sample container cap is attached to a housing, adapter, or other structure.

Example 12: The sample container cap of any examples 1-11 that is configured to move from the first position to the second position by rotating the bottom portion in a first direction and causing the projection to enter the channel and move from the first end of the channel to the second end of the channel.

Example 13: The sample container cap of any one of examples 2-12 that is configured to move from the second position to either the first position or to a third position by rotating the bottom portion in a second direction and causing the second end of the projection to press against the second end of the insert.

Example 14: The sample container cap of any of examples 1-13, wherein the cavity of the bottom portion has an inner, annular surface with threads configured to receive threads of the sample container.

Example 15: The sample container cap of example 14 that further includes a sample container threaded to the bottom portion.

Example 16: The sample container cap of any one of examples 1-15, wherein the bottom portion further includes a connective aperture configured to receive a connective stem of the top portion.

Example 17: The sample container cap of example 16, wherein the connective stem is over-molded to the top portion.

Example 18: The sample container cap of any one of examples 1-17 that further includes a gasket between the bottom portion and the top portion.

Example 19: The sample container cap of example 18, wherein the gasket includes an outer, annular portion positioned between the top opening and the bottom opening.

Example 20: The sample container cap of example 18 or 19, wherein the outer, annular portion of the gasket is positioned against a top surface of a plate of the bottom portion.

Example 21: The sample container cap of any one of examples 1-20, wherein the bottom portion has an upper cavity above a plate of the bottom portion, wherein the upper cavity has an annular wall that includes one or more protrusions that are configured to permit independent rotation of the bottom portion relative the top portion in one direction and impede the independent rotation of the bottom portion relative the top portion in the opposite direction.

Example 22: The sample container cap of example 21 that includes a plurality of protrusions.

Example 23: The sample container cap of example 16 or example 17, wherein the stem is comprised of flexible elastomer.

Example 24: The sample container cap of any one of examples 18-20, wherein the gasket is comprised of flexible elastomer.

Example 25: The sample container cap of any one of examples 20-21 or 24, wherein the stem and gasket are a single structure.

Example 26: The sample container cap of any one of examples 1-25, wherein the bottom portion further comprises an outer, annular wall comprising one or more outer threads, wherein the one or more outer threads are configured to mate with one or more threads of a housing in order to attach the sample container cap to the housing.

Example 27: The sample container cap of example 26, wherein the housing includes an inner, annular surface that is threaded and configured to receive the one or more outer threads on the outer, annular surface of the bottom portion of the sample container cap.

Example 28: A sample container unit comprising a (a) housing, and (b) the sample container cap of any one of examples 1-27.

Example 29: The sample container unit of example 28 that further includes a fluid sample tube positioned above the sample container cap.

Example 30: The sample container unit of example 29, wherein the fluid sample tube projects downward at an angle.

Example 31: The sample container unit of any one of examples 29 or 30, wherein the fluid sample tube has a first end positioned and configured to allow sample fluid to enter it, and a second end positioned and configured such that it aligns with the top opening of the top portion of the sample container cap when the sample container cap is in its second, open position.

Example 32: The sample container cap of any one of examples 1-27 that further comprises a sample container positioned in the bottom portion and a tamper-proof structure between the sample container and the bottom portion.

Example 33: The sample container cap of any one of examples 1-27 or 32 that further includes a stop positioned on the top surface of the bottom portion.

Example 34: The sample container cap of any one of examples 1-27 or 32-33 that further includes two slots in the top portion.

Example 35: The sample container cap of any one of examples 1-27 or 32-34 in which the projection is biased to a position at which the top opening and bottom opening are not aligned.

Example 36: The sample container cap of example 35, in which a channel is in the bottom portion and the projection is a cam biased by a spring.

Example 37: The sample container cap of any one of examples 35-36, in which the channel further includes an angled section juxtaposed the first end of the channel and the projection enters the angled portion when in its third position.

Example 38: The sample container cap of example 36, wherein the spring is retained on a post of the top surface of the bottom portion.

Example 39: The sample container cap of example 37, wherein the angled section is lower than a bottom of the channel.

Some further non-limiting examples of this disclosure are as follows:

Example 1: A sample container cap comprising (a) a top portion having a top opening configured to allow liquid to pass therethrough, and (b) a bottom portion having a bottom opening configured to allow liquid to pass therethrough and the bottom portion further being configured to attach to a sample container, wherein the sample container cap has a first position in which the top opening and bottom opening are not aligned and a second position in which the top opening and bottom opening are aligned and the cap is configured to permit liquid to pass therethrough.

Example 2: The sample retainer cap of example 1, wherein fluid cannot flow therethrough when the sample retainer cap is in its first position.

Example 3: The sample container cap of any one of examples 1-2, wherein one or both of the top portion and the bottom portion rotate from the first position to the second position.

Example 4: The sample container cap of any one of examples 1-4, wherein the top portion can rotate independently of the bottom portion.

Example 5: The sample container cap of any one of examples 1-4, wherein the bottom portion can rotate independently of the top portion.

Example 6: The sample container cap of example 4 that further includes a seal between the top position and the bottom portion.

Example 7: The sample container cap of any one of examples 1-6, wherein the seal includes an outer perimeter portion that seals between the top portion and a stop surface of a plate of the bottom portion.

Example 8: The sample container cap of any one of examples 6-7, wherein the seal further includes a bottom opening seal configured to the seal between the bottom opening and the top portion when the sample container cap is in the first position.

Example 9: The sample container cap of any one of examples 1-8 that further comprises a third position in which the top opening and the bottom opening are not aligned and the cap is configured so that liquid cannot pass therethrough.

Example 10: The sample container cap of example 9, wherein one or both of the top portion and the bottom portion are configured to rotate to the third position.

Example 11: The sample container cap of any one of examples 9-10 that is configured so that is cannot be rotated to its second position once placed in its third position.

Example 12: The sample container cap of any one of examples 1-11 that further comprises an external connective structure on the bottom portion to connect the sample container cap to a housing on a machine from which a fluid sample is to be taken, or to an adapter, or to the machine from which the fluid sample will be taken.

Example 13: The sample container cap of example 12, wherein the bottom portion has an outer surface and the housing connective structure is one or more threads on the outer surface.

Example 14: The sample container cap of example 13, wherein the connective structure is one helical thread on the outer surface.

Example 15: The sample container cap of any one of examples 1-14, wherein the bottom portion further includes a bottom cavity having a connective structure configured to connect to a sample container.

Example 16: The sample container cap of example 15, wherein the connective structure is one or more threads.

Example 17: The sample container cap of any one of examples 1-16 that further includes a sample container connected to the sample container cap.

Example 18: The sample container cap of any one of examples 15-17 that further includes a sample container connected to the connective structure.

Example 19: The sample container cap of example 18, wherein the sample container includes one or more threads connected to the connective structure.

Example 20: The sample container cap of any one of examples 6-8, wherein the bottom portion has a plate with an upper surface and the seal comprises a top opening seal and a bottom opening seal, wherein the bottom opening seal is configured to seal between the bottom opening and the top portion when the sample container cap is in its first position, and the top opening seal is configured to seal between the top opening and the top portion where the sample container cap is in its first position.

Example 21: The sample container cap of any one of examples 4, 6-8, or 20, wherein the seal further includes an extension configured to extend downward from a bottom surface of the top portion.

Example 22: The sample container cap of example 21, wherein the extension has a tip, a cylindrical body, and a hub that is wider than the tip and wider than the cylindrical body.

Example 23: The sample container cap of example 21 or example 22, wherein the bottom portion has an aperture configured to receive the extension.

Example 24: The sample container cap of any one of examples 1-23, wherein the bottom portion includes a plate having a top surface and a track in the top surface.

Example 25: The sample container cap of any one of examples 4, 6-8, or 20-24, wherein the seal further comprises one or more outer ridges on its outer portion.

Example 26: The sample container cap of any one of examples 1-20, wherein the top portion is further connected to the bottom portion by a fastener.

Example 27: The sample container cap of example 26, wherein the fastener has threads, the bottom portion has a non-threaded aperture, and the top portion has an aperture, and the fastener is positioned through the non-threaded aperture, and threaded into the aperture of the top portion.

Example 28: The sample container cap of example 26, wherein the fastener has one or more threads and a thread diameter, the non-threaded aperture has a second diameter larger than the thread diameter, and the aperture of the top portion has a third diameter that is less than the thread diameter.

Example 29: The sample container cap of any one of examples 1-28, wherein the bottom portion comprises steel and the top portion comprises plastic.

Example 30: The sample container cap of any one of examples 1-29, wherein the top portion is comprised of a rigid plastic component having a flexible seal integrally attached to it.

Example 31: The sample container cap of example 30, wherein the flexible seal is over-molded to the top portion.

Example 32: The sample container cap of any one of examples 30-31, wherein the flexible seal comprises an outer perimeter to seal between the top portion and the bottom portion.

Example 33: The sample container cap of example 32, wherein the bottom portion includes a plate having a top surface and the outer perimeter of the flexible seal is positioned against the top surface of the plate.

Example 34: The sample container cap of any one of examples 30-33, wherein the flexible seal further comprises a bottom opening seal configured to seal between the top portion and the bottom opening.

Example 35: The sample container cap of any one of examples 30-34, wherein the flexible seal comprises a plurality of opening seals and each of the plurality of opening seals is configured to seal either between the top portion and the top surface of the plate.

Example 36: The sample container cap of any one of examples 30-35, wherein the flexible seal further comprises a channel configured to receive either a projection or a cam.

Example 37: The sample container cap of any one of examples 30-36, wherein the flexible seal further comprises a stem that is positioned in an aperture of a plate of the bottom portion in order to connect the top portion to the bottom portion.

Example 38: The sample container cap of any one of examples 1-35 or 37 that further includes a cam positioned in a channel, wherein the channel is in a top surface of a plate of the bottom portion.

Example 39: The sample container cap of example 38, wherein the cam is in (a) a first track position when the sample container cap is in its first, closed position, and (b) a second track position when the sample container cap is in its second, open position.

Example 40: The sample container cap of example 38 or 39, wherein the cam is in a third position when the sample container cap is moved from its second, open position back to its first, closed position or moved from its second, open position to a third, closed position.

Example 41: The sample container cap of any one of examples 1-40, wherein a top surface of a plate of the bottom portion has a channel with a first end, a second end and a locking section juxtaposed the first end.

Example 42: The sample container cap of example 41, wherein the locking section of the channel is formed at an angle of 30°-90° relative the rest of the channel.

Example 43: The sample container cap of any one of examples 41-42, wherein a cam is (a) positioned in a first side of the channel when the sample container cap is in a first, closed position, (b) positioned in the second side of the channel when the sample container is in a second, open position, and (c) positioned in the locking section when the sample container cap is in a third, closed position.

Example 44: The sample container cap of any one of examples 38-43, wherein the top portion has a bottom surface and a stem extending from the bottom surface, the cam has a cam aperture, and the stem is positioned in the cam aperture.

Example 45: The sample container cap of any one of examples 38-44, wherein the bottom portion has a plate with a top surface and the channel is positioned on the top surface of the plate.

Example 46: The sample container cap of any one of examples 1-43, wherein the top portion has a top surface with a channel in the top surface of the top opening, and the channel has a first end and a second end.

Example 47: The sample container cap of example 46, wherein an insert is positioned in the channel.

Example 48: The sample container cap of example 47, wherein the insert has a first end having a first width and a second end having a second width and the first end width is greater than the second width.

Example 49: The sample container cap of any one of examples 47-48, wherein the channel is configured to receive a projection having a first end having a first end width and a second end having a second end width, wherein the second end width is greater than the first end width.

Example 50: The sample container cap of example 49, wherein the first end is rounded in plan view, and the second end is square or rectangular in plan view.

Example 51: The sample container cap of any one of examples 1-50, wherein the top opening is configured to engage a fluid sample tube of a structure to which the sample container cap is attached.

Example 52: The sample container cap of example 51, wherein the fluid sample tube is stationary and the top portion is configured to rotate independently from the bottom portion, and the top portion is held stationary while the bottom portion rotates when the fluid sample tube engages the top opening and the sample container cap is rotated to move it farther into the housing.

Example 53: The sample container cap of any one of examples 49-52, wherein the projection is (a) in the first end of the channel when the sample container is in the first, closed position, (b) in the second end of the channel when the sample container cap is in the second, open position, and (c) positioned against the second end of the insert when the sample container cap is in its third, closed position.

Example 54: The sample container cap of example 53, wherein the second end of the projection is positioned against the second end of the insert when the sample container cap is in its third, closed position.

Example 55: The sample container cap of any one of examples 1-54, wherein a top surface of a plate of the bottom portion has an outer rim that includes a raised lip having an inner, annular wall with outwardly-extending ribs that engage the detents and help prevent rotation of the bottom portion independently of the top portion.

Example 56: The sample container cap of any one of examples 1-55 that further includes a top closure attached to the cap.

Example 57: The sample container cap of example 56, wherein the top closure is threaded onto the cap.

Example 58: The sample container cap of any one of examples 1-57 that further includes a radio frequency identification (RFID) tag or label.

Example 59: The sample container cap of example 58 that further includes an antenna configured to receive and transmit a radio frequency (RF) signal.

Example 60: The sample container cap of any one of examples 1-59 that further includes a tamper-resistant structure between a sample container and the sample container cap.

Example 61: The sample container of example 60, wherein the tamper resistant structure is shrink-wrap plastic.

Example 62: The sample container cap of any one of examples 60-61, wherein the tamper-resistant structure is positioned between the sample container and the bottom portion of the sample container cap.

Example 63: The sample container cap of any one of examples 1-62 that further includes a second tamper-resistant structure between a top closure and the sample container cap.

Example 64: The sample container cap of example 63, wherein the second tamper-resistant structure is shrink-wrap plastic.

Example 65: The sample container cap of any one of the examples 62-63, wherein the tamper-resistant structure is between the top closure and the bottom portion.

Example 66: The sample container cap is any one of examples 1-65 that further includes an adapter having a first end having a first opening that is connected to the sample container cap and a second portion having a second opening that is configured to attach to a fluid collection device, and the adapter further includes a passage between the first opening and the second opening, wherein the passage is configured to allow the passage of fluid therethrough.

Example 67: The sample container cap of example 66, wherein the first end of the adapter is offset from the second end of the adapter.

Example 68: The sample container cap of any one of examples 66-67, wherein the fluid collection device is a hand pump.

Example 69: The sample container cap of any one of examples 66-68 that further includes a stem extending downward from the first opening of the adapter, wherein the stem is configured to engage the top opening of the top portion of the sample container cap.

Example 70: The sample container cap of any one of examples 66-69, wherein the first opening is threaded and is threaded onto one or more threads of the outside surface of the bottom portion of the sample container cap.

Example 71: The sample container cap of any one of examples 1-70 that further includes a leg on a top surface of the top portion, wherein the leg is configured to engage a fluid sample tube in order to prohibit the rotation of the top portion.

Example 72: The sample container cap of any one of examples 1-21 that is configured so that it cannot be moved to its first position after being placed in its second position.

Example 73: The sample container cap of any one of examples 9-11 or 72, wherein the third position is different from the first position.

Some further non-limiting examples of this disclosure are as follows:

Example 1: A method for assembling and using a cap for a sample container, the method comprising the steps of:
  (a) aligning a top portion of the cap with a bottom portion of the cap;
  (b) pressing the top portion and bottom portion together to form an assembled cap;
  (c) connecting a sample container to the bottom portion; and
  (d) applying a first security structure that at least partially covers the assembled cap and that at least partially covers the sample container.

Example 2: The method of example 1, wherein the top portion has a top opening and the bottom portion has a bottom opening and the step of aligning the top portion and the bottom portion comprises not aligning the top opening and the bottom opening so that the assembled cap is configured so that fluid cannot pass therethrough.

Example 3: The method of example 1 or example 2, wherein the top portion comprises a slot having an indentation and the bottom portion comprises a locator pin and the top portion and bottom portion are aligned when the indentation in the slot and the locator pin are aligned.

Example 4: The method of any one of examples 1-3, wherein the top portion has a bottom surface and the top portion has a plate with an upper surface and there is a first seal between the top opening and the upper surface of the bottom portion and a second seal between the bottom opening and the top portion.

Example 5: The method of any one of examples 1-4, wherein the security structure is plastic and that further includes the step of shrink-wrapping the plastic around at least part of the assembled cap and at least part of the sample container.

Example 6: The method of any one of examples 1-5 that further includes attaching a top closure to the assembled cap.

Example 7: The method of any one of examples 6 that further includes the step of attaching a second security structure over at least part of the top closure and over at least part of the assembled cap.

Example 8: The method of example 7, where the second security structure is plastic and that further includes the step of shrink-wrapping the plastic on the at least part of the top closure and the at least part of the assembled cap Example 9: The method of any one of examples 6-8 that further includes the step of removing the top closure.

Example 10: The method of example 7 or example 8 that further includes the steps of removing the second security feature and removing the top closure.

Example 11: The method of any one of examples 1-10, wherein the step of aligning the top portion and the bottom portion comprises aligning a top indicia on the top portion with a bottom indicia on the bottom portion.

Example 12: The method of any one of examples 1-5 or 9-11 that further includes the step of directly or indirectly attaching the assembled cap to a machine, an adapter, or another structure.

Example 13: The method of example 12 that further includes the step of aligning the assembled cap with a cavity of the machine, adapter, or another structure prior to attaching the assembled cap.

Example 14: The method of example 12 or 13, wherein the assembled cap is indirectly attached to the machine by directly attaching the assembled cap to a fluid sample housing that is connected to the machine or to an adapter that is connected to the machine.

Example 15: The method of example 14, wherein the assembled cap is attached to a first end of an adapter and a second end of the adapter is connected to the machine.

Example 16: The method of example 15, wherein the machine is a hand pump.

Example 17: The method of any one of examples 12-16, wherein the step of directly or indirectly attaching the assembled cap comprises threading the assembled cap into a cavity.

Example 18: The method of example 17, wherein the assembled cap has one or more outer threads and the cavity has one or more cavity threads and at least one of the one or more outer threads engages at least one of the one or more cavity threads.

Example 19: The method of any one of examples 12-18 that further include the step of rotating the bottom portion relative the top portion to move the assembled cap into a second position in which the top opening and the bottom opening align and the cap is configured to allow fluid to pass therethrough and into the sample container.

Example 20: The method of example 19, wherein the top portion is maintained in position during at least part of the time the bottom portion is rotated.

Some further non-limiting examples of this disclosure are as follows:

Example 1: A top portion of a sample container cap comprising:
  (a) a top surface;
  (b) a bottom surface;
  (c) a top opening offset from a center of the top portion;

(d) wherein the top portion is configured to connect to a bottom portion.

Example 2: The top portion of example 1 that further includes an insert in the channel, wherein the insert has a first end having a first width and a second end having a second width, wherein the first width is greater than the second width.

Example 3: The top portion of example 1 that further comprises an outer wall having an inward-facing extension, wherein the outer wall is configured to flex outwards.

Example 4: The top portion of example 3, wherein the inward-facing extension has an end including a chamfer.

Example 5: The top portion of examples 3 or 4, wherein (a) the top portion has an outer perimeter, and (b) the outer wall has (i) a top connected to the top surface, and (ii) a downwardly-extending portion spaced apart from the outer perimeter.

Example 6: The top portion of any one of examples 1-5 that further includes a seal on the bottom.

Example 7: The top portion of example 6, wherein the seal is integrally connected to the top portion.

Example 8: The top portion of any one of examples 6 or 7, wherein the seal comprises an outer perimeter.

Example 9: The top portion of any one of examples 6-8, wherein the seal further comprises a top opening seal configured to seal between the top opening and a surface on a bottom portion of the sample container cap.

Example 10: The top portion of any one of examples 6-9, wherein the seal further comprises a bottom opening seal configured to seal between the top opening and a bottom opening in a bottom portion of the cap.

Example 11: The top portion of any one of examples 6-10, wherein the seal further comprises a center stem configured to be received in an aperture of a bottom portion of the cap.

Example 12: The top portion of any one of examples 1-11 that is circular in plan view.

Example 13: The top portion of any one of examples 1 or 3-12 that further includes a channel in the top surface, wherein the channel has a first end, a second end, and is configured to receive a projection Example 14: The top portion of example 13 that further comprises an insert positioned in the channel.

Example 15: The top portion of example 14, wherein the insert has a first end having a first width and a second end having a second width, wherein the first width is greater than the second width.

Example 16: The top portion of any one of examples 1-12 that further includes a screw boss in the bottom surface.

Example 17: The top portion of example 11, wherein the stem extends downward from the bottom surface of the top portion, wherein the stem has a hub, and a bottom portion has a plate comprising a top surface and a bottom surface and the hub is configured to be passed through the aperture and be positioned against the bottom surface of the bottom portion.

Example 18: The top portion of any one of examples 2-17 wherein the second end of the insert in the channel is configured to move between the second width and a width wider than the second width.

Example 19: The top portion of any one of examples 3-18, wherein inward-facing extension is configured to be received in a groove of a bottom portion of the cap.

Example 20: The top portion of any one of examples 2-19, wherein the channel has an arcuate shape.

Example 21: The top portion of any one of examples 1-20 that is connected to a bottom portion.

Example 22: The top portion of example 7, wherein the seal is over-molded to the top portion.

Example 23: The top portion of any of examples 3-22, wherein the outer wall and the inward-facing extension are on only part of the top portion.

Example 24: The top portion of example 23, wherein the outer wall and the inward-facing extension are on less than ½ of the top portion.

Some further non-limiting examples of this disclosure are as follows:

Example 1: A bottom portion of a cap for use with a sample container, the bottom portion comprising:
  (a) a body;
  (b) a plate juxtaposed the top of the body, wherein the plate has a top surface and a bottom surface;
  (c) a cavity beneath the plate, wherein the cavity has an annular surface;
  (d) one or more threads on an outside surface of the body;
  (e) one or more threads on the annular surface of the cavity; and
  (f) a bottom opening in the plate.

Example 2: The bottom portion of example 1, that further comprises a channel in the top surface of the plate.

Example 3: The bottom portion of example 2, wherein the channel comprises a first end and a second end.

Example 4: The bottom portion of example 3, wherein the channel further comprises a recessed channel bottom and a locking section juxtaposed the first end, wherein the locking section has a bottom that is lower than the channel bottom.

Example 5: The bottom portion of any one of examples 3 or 4, wherein the locking section is formed at an angle relative a remainder of the channel.

Example 6: The bottom portion of any one of examples 2-5 that further includes a cam in the channel.

Example 7: The bottom portion of any one of examples 1-5 that further includes an aperture in the plate, wherein the aperture is configured to receive a stem in order to connect a top portion to the bottom portion.

Example 8: The bottom portion of any one of examples 1-7 that further includes a stop projecting upwards from the top surface, wherein the stop is configured to contact a structure on a top portion when the top portion is connected to the bottom portion in order to prevent rotation of the bottom portion relative the top portion.

Example 9: The bottom portion of any one of examples 1-8 that further includes alignment indicia on an outside surface of the body, where the alignment indicia are configured to align with indicia on a top portion or on a machine.

Example 10: The bottom portion of any one of examples 1-9 that is attached to a sample container.

Example 11: The bottom portion of example 10 wherein the sample container is threaded into the cavity of the bottom portion.

Example 12: The bottom portion of any one of examples 1-11 that is connected to a top closure.

Example 13: The bottom portion of example 12, wherein the top closure is threaded onto one or more threads on the outside of the body of the bottom portion.

Example 14: The bottom portion of any one of examples 1-13 that is connected to a top portion.

Example 15: The bottom portion of any one of examples 12-14 that further comprises a first security structure between the top closure and the bottom portion.

Example 16: The bottom portion of example 15, wherein the first security structure is shrink-wrap plastic.

Example 17: The bottom portion of any one of examples 10-11 that further includes a second security feature between the bottom portion and the sample container.

Example 18: The bottom portion of example 17, wherein the second security feature is shrink-wrap plastic.

Some additional, non-limiting examples of this disclosure are as follows:

Example 1: A sample container cap (or "cap") comprising: (a) a bottom portion having a plate with a top surface and a bottom surface, a bottom cavity, and a bottom opening in the plate; and (b) a top portion attached to the bottom portion, wherein the top portion has a top opening; wherein the sample container cap has (c) a first position in which the bottom opening and the top opening are not aligned and the cap is configured so that fluid cannot pass through the sample container cap, and (d) a second position in which the bottom opening and top opening are aligned and the cap is configured to permit the passage of fluid therethrough.

Example 2: The sample container cap of example 1 that further includes a third position in which the bottom opening and the top opening are not aligned and are configured so that fluid cannot pass through the cap.

Example 3: The example cap of one of example 1, wherein the top portion has a top surface and a channel is in the top surface of the top portion.

Example 4: The cap of any of examples 1-3, wherein each of the bottom portion and the top portion include one or more structures configured to prevent over rotation of the bottom portion relative the top portion.

Example 5: The cap of example 1, wherein the bottom portion has a top surface and a channel is in the top surface of the bottom portion.

Example 6: The cap of example 4, wherein one of the structures to prevent over rotation is part of an insert positioned in the channel.

Example 7: The cap of example 4, wherein an insert is positioned in the channel, wherein the insert has a first end having a first width and a second end having a second width, wherein the second width is less the first width.

Example 8: The cap of any one of examples 3-7, wherein the channel is configured to receive a projection, and the projection has a first end having a first projection width and a second end having a second projection width, wherein the second projection width is greater than the first projection width.

Example 9: The cap of example 8, wherein the second projection width is greater than the second width of the second end of the insert.

Example 10: The cap of example 8, wherein the first projection width is less than the first width of the first end of the insert and less than the second width of the second end of the insert.

Example 11: The cap of any one of examples 1-10, wherein the cap is configured to be in the first, closed position before being attached to a housing, adapted, or other structure.

Example 12: The cap of any one of examples 3 or 7-11, wherein the channel is engaged with a projection and the cap is configured to move from the first, closed position to the second, open position by rotating the bottom portion in a first direction and causing the projection to move from the first end of the channel to the second end of the channel.

Example 13: The cap of any one of examples 1-12 that further includes a sample container attached to the bottom portion.

Example 14: The cap of any one of examples 1013, wherein the bottom portion has one or more extensions that are configured to permit independent rotation of the bottom portion relative the top portion in one direction and impede the independent rotation of the bottom portion relative the top portion in the opposite direction.

Example 15: The cap of example 1, wherein the bottom portion further comprises an outer, annular wall having outer threads, wherein the outer threads are configured to mate with the threads of a housing, an adapter, a top closure, or other structure.

Example 16: The cap of example 13 that further comprises a first security structure positioned over at least part of the bottom portion and over at least part of the sample container.

Example 17: The cap of any one of examples 1-16 that further comprises a seal between the top portion and the bottom portion.

Example 18: The cap of any one of examples 1-17 that further comprises a third position in which the top opening and the bottom opening are not aligned and the cap is configured so that liquid cannot pass therethrough.

Example 19: The cap of example 18, wherein the bottom portion rotates to the third, closed position.

Example 20: The cap of any one of examples 18-19, wherein the cap is configured so that it cannot be moved to its second position once its placed in its third position.

Example 21: The cap of any one of examples 1-20 that further comprises a connective structure to connect the cap directly or indirectly to a machine from which a fluid sample is to be taken.

Example 22: The cap of example 21, wherein the bottom portion has an outer wall and the connective structure is one or more threads on the outer wall.

Example 23: The cap of any one of examples 1-22, wherein the bottom portion further includes an inner cavity having a cavity connector structure configured to connect to a sample container.

Example 24: The cap of example 23, wherein the cavity connective structure is one or more threads.

Example 25: The cap of any one of examples 23-24 that further includes a container connected to the cap.

Example 26: The cap of example 17, wherein the bottom portion has a plate with an upper surface and the seal comprises a top opening seal and a bottom opening seal, wherein the bottom opening seal is configured to seal between the bottom opening and the top portion when the cap is in its first, closed position or its third, closed position, and the top opening seal is configured to seal between the top opening and the upper surface of the plate of the bottom portion when the cap is in its first, closed position or its third, closed position.

Example 27: The cap of any one of examples 17 or 26, wherein the seal further includes an extension configured to extend downward from a bottom surface of the top portion.

Example 28: The cap of example 27, wherein the extension has a first end, a second end, a body including a hub, wherein the hub is wider than the rest of the body.

Example 29: The cap of any of examples 27-28, wherein the bottom portion has a plate that includes an aperture configured to receive the second end of the hub of the extension.

Example 30: The cap of any one of examples 17, or 26-29, wherein the seal further comprises an outer portion configured to be positioned on a top surface of a plate of the bottom portion.

Example 31: The cap of any one of examples 17, or 26-30, wherein the seal further comprises ridges on an outer portion of the seal.

Example 32: The cap of any one of examples 17, 26, or 31, wherein the top portion is connected to the bottom portion by a fastener.

Example 33: The cap of example 32, wherein the fastener has threads, the bottom portion has a plate with a non-threaded aperture, and the top portion has a bottom surface with a fastener aperture, and the fastener is positioned in the non-threaded aperture, and threaded into the fastener aperture.

Example 34: The cap of any one of examples 1-33, wherein the top position is comprised of a rigid plastic component having the seal over-molded to it.

Example 35: The cap of any one of examples 1-34 that further includes a cam or a projection positioned in the channel.

Example 36: The cap of example 35, wherein the cam or projection is in (a) a first channel position when the cap is in its first, closed position, and (b) a second channel position when the cap is in its second, open position.

Example 37: The cap of example 36, wherein the cam or projection is in a third position when the cap is moved from its second, open position to its first, closed position or to a third, closed position.

Example 38: The cap of any one of examples 35-37, wherein the channel has a first end, a second end, and a locking section juxtaposed the first end.

Example 39: The cap of example 38, wherein the locking section of the channel is formed at an angle of 30°-90° relative a portion of the channel to which the locking section is connected.

Example 40: The cap of any one of examples 35-39, wherein the cam is (a) positioned in the first side of the channel when the cap is in its first position, (b) positioned in the second side of the channel when the cap is in its second position, and (c) positioned in the locking section when the cap is moved from its second, open position to a third, closed position.

Example 41: The cap of any one of examples 35-40, wherein the top portion has a bottom surface and a stem extending from the bottom surface, the cam has a cam aperture, and the stem is positioned in the cam aperture.

Example 42: The cap of any one of examples 35-41, wherein the bottom portion has a plate comprising a top surface and the channel is positioned in the top surface of the plate.

Example 43: The cap of any one of examples 1-34, wherein the top portion has a top surface and the channel is positioned I the top surface of the top portion.

Example 44: The cap of example 43, wherein the channel is configured to receive a projection.

Example 45: The cap of any one of examples 1-44 that includes a channel and an insert positioned in the channel, wherein the insert has a first end having a first end width and a second end having a second end width and the first end width is greater than the second end width.

Example 46: The cap of any one of examples 43-45, wherein the projection has a first end having a first end width and a second end having a second end width, wherein the second end width is greater than the first end width.

Example 47: The cap of example 46, wherein the first end is of the projection rounded in plan view, and the second end of the projection is square or rectangular in plan view.

Example 48: The cap of any one of examples 44-47, wherein the projection is (a) in the first end of the channel when the cap is in its first, closed position, and (b) in the second end of the channel when the cap is in its second, open position.

Example 49: The cap of example 48, wherein the second end of the projection is positioned against the second end of the insert when the cap is in its third, closed position.

Example 50: The cap of any one of examples 1-49 that further includes a top closure attached to the cap.

Example 51: The cap of any one of examples 1-50 that further includes a radio frequency identification (RFID) code structure, such as a label or tag.

Example 52: The cap of example 51 that further includes an antenna configured to receive and transmit a radio frequency (RF) signal.

Example 53: The cap of example 16, wherein the first security structure is shrink-wrap plastic.

Example 54: The cap of any one of examples 1-53 that further includes an adapter having (a) a first end with a first adapter opening that is connected to the cap, and (b) a second end with a second adapter opening that is configured to attach to a fluid collection device, and the adapter further includes a passage between the first opening and the second opening, wherein the passage is configured to allow the passage of fluid therethrough.

Example 55: The cap of example 54, wherein the first end of the adapter is offset from the second end of the adapter.

Example 56: The cap of any one of examples 54-55, wherein the fluid collection device is a hand pump, a machine, or a housing connected to a machine.

Example 57: The cap of any one of examples 54-55, wherein the adapter further includes a stem extending downward from the first adapter opening, wherein the stem is configured to engage the top opening of the top portion of the cap.

Example 58: The cap of any one of examples 54-57, wherein the first adapter opening has one or more internal threads and the cap is threaded into the first adapter opening.

Example 59: The cap of example 58, wherein the threaded portion of the sample container cap is on an outside surface of the bottom portion of the cap.

Some further, non-limiting examples of this disclosure are as follows:

Example 1: A cap for a container, the cap comprising:
(a) a top portion having a top opening and a first connective structure;
(b) a bottom portion having a bottom opening and a second connective structure;
wherein the top portion is connected to the bottom portion by the first connective structure being connected to the second connective structure and the bottom portion is moveable relative the top portion to (i) a position at which the top opening and bottom opening align and the cap is configured to permit the passage of fluid therethrough, and (ii) a position at which the top opening and bottom opening are not aligned and the cap is configured to not permit the passage of fluid therethrough.

Example 2: The cap of example 1 that further comprises a seal between the top portion and the bottom portion.

Example 3: The cap of any one of examples 1 or 2, wherein the top portion has an annular outer wall and the bottom portion had an annular outer wall.

Example 4: The cap of any one of examples 1-3, wherein the bottom portion has a plate with a top surface and a bottom surface and a friction track on the top surface of the plate.

Example 5: The cap of example 4, wherein the seal has an outer, annular portion that seals against the top surface of plate.

Example 6: The cap of any one of examples 2-5, wherein the seal is attached to the top portion.

Example 7: The cap of any one of examples 2-6, wherein the bottom portion includes a body, a lower cavity, an upper cavity, and the plate is between the lower cavity and the upper cavity, wherein the top surface of the plate is juxtaposed the upper cavity and a bottom surface of the plate is juxtaposed the lower cavity.

Example 8: The cap of any one of examples 1-7, wherein the top portion has a top surface and a bottom surface.

Example 9: The cap of example 8, wherein the bottom surface of the top portion is positioned in the upper cavity of the bottom portion.

Example 10: The cap of any one of examples 8 or 9, wherein the seal is connected to the bottom surface of the top portion.

Example 11: The cap of any one of examples 2-10, wherein the seal further comprises a top opening seal that is configured to seal between the top opening and the upper surface of the plate of the bottom portion.

Example 12: The cap of example 11, wherein the top opening seal at least partially surrounds the top opening.

Example 13: The cap of example 12, wherein the top opening seal entirely surrounds the top opening.

Example 14: The cap of any one of examples 12-13, wherein the top opening seal presses against the top surface of the plate of the bottom portion.

Example 15: The cap of any one of examples 2-14, wherein the seal further comprises a bottom opening seal that is configured to seal between the bottom opening and the top portion.

Example 16: The cap of example 15, wherein the bottom opening seal is attached to the bottom surface of the top portion.

Example 17: The cap of any one of examples 15-16, wherein the bottom opening seal at least partially surrounds the bottom opening when the top opening and bottom opening are not aligned and the cap is configured to not permit the passage of fluid therethrough.

Example 18: The cap of example 17, wherein the bottom opening seal completely surrounds the bottom opening when the bottom opening and top opening are not aligned and the cap is configured to not permit the passage of fluid therethrough.

Example 19: The cap of any one of examples 2-18, wherein the seal is comprised of flexible elastomer.

Example 20: The cap of any one of examples 15-19, wherein the top opening seal and the bottom opening seal are each configured to slide across the top surface of the plate of the bottom portion.

Example 21: The cap of any one of examples 15-20, wherein the outer annular sealing portion, the bottom opening seal, and the top opening seal are connected.

Example 22: The cap of anyone of examples 7-21, wherein the plate of the bottom portion has an aperture passing therethrough.

Example 23: The cap of any one of examples 1-22 that further includes a stem that connects the top portion to the bottom portion.

Example 24: The cap of example 23, wherein the stem is connected to the top portion and connected to the bottom portion.

Example 25: The cap of any one of examples 23-24, wherein the stem is over-molded to the top portion.

Example 26: The cap of any one of examples 23-25, wherein the stem is positioned in the aperture in the plate of the bottom portion.

Example 27: The cap of any one of examples 23-26, wherein the stem comprises flexible elastomer.

Example 28: The cap of any one of examples 23-27, wherein the stem is integrally formed with the seal.

Example 29: The cap of any one of examples 23-28, wherein the stem has a first end connected to the top portion, a second end, and a center hub, wherein the second end and center hub are positioned below the bottom surface of the plate of the bottom portion.

Example 30: The cap of any one of examples 21-29, wherein the aperture is in the center of the plate of the bottom portion.

Example 31: The cap of any one of examples 1-22, wherein the top portion and the bottom portion are connected by a fastener.

Example 32: The cap of example 31, wherein the bottom surface of the top portion comprises a fastener boss configured to receive and retain the fastener.

Example 33: The cap of any one of examples 31-32, wherein an aperture in the plate of the bottom portion is configured to permit the fastener to pass through and be retained in.

Example 34: The cap of example 33, wherein the fastener is not threaded to or otherwise attached to the aperture.

Example 35: The cap of any one of examples 31-34 that further includes a washer between a head of the fastener and the bottom surface of the plate of the bottom portion.

Example 36: The cap of any one of examples 1-22, wherein the top portion has a body, a top surface, an outer annular wall and a space in the top surface, wherein the space extends between the body and the outer annular wall.

Example 37: The cap of example 36, wherein the outer annular wall has an inward-facing extension.

Example 38: The cap of any one of examples 36-37, wherein the bottom portion further comprises an annular side groove.

Example 39: The cap of example 38, wherein the inward-facing extension is positioned in the annular side groove.

Example 40: The cap of any one of examples 37-39, wherein the inward-facing extension has a chamfered tip.

Example 41: The cap of any one of examples 38-40, wherein the annular side groove comprises a chamfered edge.

Example 42: The cap of any one of examples 1-41 that is configured so that the top opening and bottom opening are not aligned when the cap is first assembled and the cap is not configured to permit fluid to pass therethrough when first assembled.

Example 43: The cap of any one of examples 2-7, wherein the seal is connected to the top portion.

Example 44: The cap of example 12, wherein the top opening seal is attached to the bottom surface of the top portion.

Example 45: The cap of any one of examples 1-41, wherein the top opening and bottom opening are aligned when the cap is first assembled and the cap is configured to permit fluid to pass therethrough.

Example 46: The cap of any one of examples 1-45, wherein the bottom portion further includes an alignment feature.

Example 47: The cap of any one of examples 1-46, wherein the top portion further included an alignment feature.

Example 48: The cap of any one of examples 46-47, wherein the alignment feature of the bottom portion is indicia on an outer surface of the bottom portion.

Example 49: The cap of any one of examples 46-48, wherein the alignment feature of the top portion is on either a side or the top surface of the top portion.

Example 50: The cap of any one of examples 1-50, wherein the bottom is moveable relative the top portion by rotating the bottom portion while maintaining the top portion stationary.

Example 51: The cap of any one of examples 1-50, wherein the cap is moveable from (a) a first position at which the top opening and the bottom opening are not aligned and the cap is not configured to permit the passage of fluid therethrough, to (b) a second position at which the top opening and the bottom opening are aligned and the cap is configured to permit the passage of fluid therethrough, and to (c) a position at which the top opening and bottom opening are not aligned and the cap is not configured to permit the passage of fluid therethrough.

Example 52: The cap of any one of examples 1-50, wherein the cap is moveable from (a) a first position at which the top opening and the bottom opening are not aligned and the cap is not configured to permit the passage of fluid therethrough, to (b) a second position at which the top opening and the bottom opening are aligned and the cap is configured to permit the passage of fluid therethrough, and to (c) a third position at which the top opening and bottom opening are not aligned and the cap is not configured to permit the passage of fluid therethrough.

Example 53: The cap of example 52, wherein the first position is different from the third position.

Example 54: The cap of any one of examples 1-53, wherein the top portion is configured to be maintained in stationary position and the bottom portion is configured to move while the top portion is maintained in the stationary position.

Example 55: The cap of any one of examples 1-54 that further includes channel configured to receive a fixed-position projection.

Example 56: The cap of any one of examples 1-55 wherein the top portion includes a top protrusion and the bottom portion includes a bottom protrusion and the top protrusion and bottom protrusion touch when the cap is in its second position in order to help prevent over rotation.

Example 57: The cap of any one of examples 1-56, where the top surface of the bottom portion includes a stop and the bottom surface of the top portion includes a structure configured to press against the stop when the cap is in its second position in order to help prevent over rotation.

Example 58: The cap of any one of examples 1-57, wherein the cap locks so that it cannot be moved to the open position when moved from the open position to the closed position.

Example 59: The cap of example 58, wherein the cap is locked when in the third, closed position so that it cannot be moved to the second, open position.

Example 60: The cap of example 59 that further includes an edge on an outer track of the top portion and an edge on an outer track of the bottom portion, wherein the edges are configured to press against one another to prevent moving the cap to its open position after the cap has been moved from its open position to a closed position in order to lock the cap so it cannot be moved to the open position.

Example 61: The cap of any one of example 1-60, wherein the seal comprises an outer seal, a top opening seal configured to seal between the top opening and a top surface of the plate of the bottom portion, and a bottom opening seal configured to seal between the bottom opening and the top portion.

Example 62: The cap of example 61, wherein the seal is attached to the top portion.

Example 63: The cap of example 62, wherein the seal is integrally formed to the top portion.

Example 64: The cap of example 62 or example 63, wherein the seal is over-molded to the top portion.

Example 65: The cap of any one of examples 61-64, wherein the top opening seal and the bottom opening seal are each configured to slide across the top surface of the plate of the bottom portion.

Example 66: The cap of any one of examples 61-65, wherein the outer seal is configured to slide across the top surface of the plate of the bottom portion.

Example 67: The cap of any one of examples 1-66 that further includes a stem and the bottom portion has a plate with an aperture configured to receive part of the stem.

Example 68: The cap of example 67, wherein the aperture is in the center of the plate of the bottom portion.

Example 69: The cap of example 67 or example 68, wherein the stem has a first end, a second end, and a central hub between the first end and the second end, wherein the central hub is positioned in a bottom cavity of the bottom portion.

Example 70: The cap of any of examples 67-69, wherein the stem is attached to the top portion.

Example 71: The cap of example 70, wherein the stem is molded to the top portion.

Example 72: The cap of any one of examples 1-71, wherein the top portion has a top surface and a channel in the top surface.

Example 73: The cap of any one of examples 1-71, wherein the bottom portion has a top surface and a channel in the top surface.

Example 74: The cap of example 72, wherein the channel has a first end and a second end.

Example 75: The cap of example 73, wherein the channel has a first end and a second end.

Example 76: The cap of anyone of examples 72 or 74, wherein there is an insert positioned in the channel and the insert has a first end having a first width and a second end having a second width, wherein the first width is greater than the second width.

Example 77: The cap of example 76, wherein the second end of the insert is configured to flex outward to a third width that is greater than the second width in response to a structure that has a width greater than the second width moving through the insert.

Example 78: The cap of example 27, wherein the second end of the insert is configured to flex inward from the third width to the second width.

Example 79: The cap of any one of examples 1-78, wherein the top portion has an outer wall with an inward-facing extension, and the bottom portion has an outer wall with a groove, and the inward-facing extension is positioned in the groove.

Example 80: The cap of example 79, wherein the inward-facing extension has a chamfered end.

Example 81: The cap of example 80, wherein the outer wall has an outer wall chamfer above the groove and the outer wall chamfer is configured to engage the chamfered end prior to the inward-facing extension being reviewed in the groove.

Some further non-limiting examples of this disclosure follow:

Example 1: A cap for a fluid sample container, the cap comprising:

(a) a top portion having a top opening and a top connective structure; and (b) a bottom portion having a bottom opening and a bottom connective structure;
wherein the top portion is connected to the bottom portion by the top connective structure being connected to the bottom connective structure and the cap is moveable to (i) a second position at which the top opening and bottom opening align and the cap is configured to permit the passage of fluid therethrough, and (ii) a third position at which the top opening and bottom opening are not aligned and the cap is configured to not permit the passage of fluid therethrough.

Example 2: The cap of example 1 that further comprises a seal between the top portion and the bottom portion.

Example 3: The cap of any one of examples 1-2, wherein the bottom portion includes a body, a lower cavity, an upper cavity, and a plate between the lower cavity and the upper cavity, wherein the plate has a top surface juxtaposed the upper cavity and a bottom surface juxtaposed the lower cavity.

Example 4: The cap of example 3, wherein the top portion is at least partially positioned in the upper cavity of the bottom portion.

Example 5: The cap of any one of examples 3 or 4 that further comprises a top opening seal that (a) surrounds the top opening, and (b) presses against the upper surface of the plate.

Example 6: The cap of any one of examples 1-5 that further comprises a bottom opening seal that is configured to seal between the bottom opening and the top portion when Example 1: The cap is in the third position.

Example 7: The cap of example 6, wherein the bottom opening seal is configured to surround the bottom opening when Example 1: The cap is in the third position.

Example 8: The cap of any one of examples 1-7, wherein the top portion has a body, a top surface, an outer wall, and a slot in the top surface, wherein the slot extends below the top surface to create a space between the body and the outer wall.

Example 9: The cap of any one of examples 1-8, wherein the bottom portion further comprises an annular side groove.

Example 10: The cap of any one of examples 8-9, wherein the outer wall has an inward-facing extension.

Example 11: The cap of example 10, wherein the inward-facing extension is positioned in the annular side groove of the bottom portion.

Example 12: The cap of any one of examples 1-11, wherein the bottom portion is configured to be moveable relative the top portion by rotating the bottom portion while maintaining the top portion in a stationary position.

Example 13: The cap of any one of examples 1-12, wherein the cap is moveable from (a) a first position at which the top opening and the bottom opening are not aligned and the cap is not configured to permit the passage of fluid therethrough, to (b) the second position, and to (c) the third position, wherein the third position is different from the first position.

Example 14: The cap of any one of examples 3-5, wherein the top surface of the plate includes a stop and a bottom surface of the top portion includes a structure configured to press against the stop when the cap is in the second position in order to help prevent over rotation past the second position.

Example 15: The cap of any one of examples 3-5, wherein the top surface of the plate includes a stop and the bottom surface of the top portion includes a second structure configured to press against the stop when the cap is in the third position in order to help prevent over rotation past the third position.

Example 16: The cap of any one of examples 9-11 that further includes a protrusion on the inward-facing extension and a protrusion in the annular side groove, wherein the protrusion on the inward-facing extension and the protrusion in the groove are configured to press against one another in order to help prevent the cap from moving to the second position after the cap has been moved to the third position.

Example 17: The cap of any one of examples 1-16, wherein the top portion comprises a channel configured to receive a stationary projection of a housing, adapter, or machine to which the cap is attached.

Example 18: The cap of example 17 that further includes an insert positioned in the channel and the insert has a first end having a first width and a second end having a second width, wherein the first width is greater than the second width.

Example 19: The cap of example 18, wherein the second end of the insert is configured to flex outward to a third width that is greater than the second width in response to the second end of the insert moving past the stationary projection when the cap is rotated.

Example 20: The cap of any one of examples 10 or 11, wherein the inward-facing extension has a chamfered end.

Example 21: The cap of any one of examples 17-19, wherein the channel has an annular shape.

Example 22: The cap of example 13, wherein the bottom portion is configured to be in the first position when the top portion is first connected to the bottom portion and before the sample container cap is attached to a housing, adapter, or other structure.

Example 23: The cap of any one of examples 17-19 or 21, wherein when the cap is in the second position the stationary projection is positioned in a second end of the channel.

Example 24: The cap of example 23, wherein when the cap is in the third position the stationary projection is pressed against the second end of the insert.

Example 25: The cap of any one of examples 3-24, wherein the lower cavity of the bottom portion has an inner, annular surface with threads configured to receive threads of a sample container.

Example 26: The cap of example 25 that further includes a sample container threaded into the cavity of the bottom portion.

Example 27: The cap of any one of examples 2-26, wherein the seal is over-molded to the top portion.

Example 28: The cap of any one of examples 3-27, wherein the seal includes an outer, annular portion positioned between the top portion and the top surface of the plate.

Example 29: The cap of any one of examples 1-28 that further comprises a sample container connected to the bottom portion and a tamper-proof structure between the sample container and the bottom portion.

Example 30: The cap of any one of examples 1-29 that further comprises an external connective structure on the bottom portion, wherein the external connective structure is configured to connect the cap to a housing on a machine from which a fluid sample is to be taken, or to an adapter, or to the machine from which the fluid sample will be taken, or to a top closure.

Example 31: The cap of example 30, wherein the bottom portion has an outer surface and the external connective structure is one or more threads on the outer surface.

Example 32: The cap of any one of examples 8-11 that has a plurality of slots, wherein each of the plurality of slots extends below the top surface to create a space between the body and the outer wall.

Example 33: The cap of example 32, wherein the outer wall is juxtaposed each of the slots.

Example 34: The cap of example 33, wherein each outer wall has an inwardly-facing projection positioned in the annular side groove.

Example 35: The cap of example 16, wherein the protrusion aligns with and is received in an indentation on the bottom portion in order to properly align the top portion and the bottom portion when they are connected.

Example 36: The cap of example 35 that is in a first position in which the top opening and bottom opening are not aligned and the cap is not configured to permit the passage of fluid therethrough when the top portion and the bottom portion are connected.

Example 37: The cap of example 14, wherein the bottom surface of the top portion further includes a second structure configured to press against the stop when the cap is in the third position in order to help prevent over rotation past the third position.

The present invention has been described above with reference to exemplary embodiments and examples. The particular embodiments shown and described herein are illustrative only, and are not intended to limit the scope of the claims. Changes and modifications are intended to be included within the scope of the claims and the legal equivalents thereof.

What is claimed is:

1. A cap for use on a container for collecting fluid samples, the cap comprising:
    (a) a body having a top portion with an interior top surface, a top opening in the top portion, and a support extending from the interior top surface into a cavity of the body, wherein the support has at least one wall and at least one body opening; and
    (b) a shutter connected to the body and positioned at least partially in the cavity, wherein the shutter has at least one shutter opening,
    wherein the cap has (i) a first, closed position in which the at least one shutter opening aligns with the at least one wall and fluid cannot pass through the cap, (ii) a second, open position in which the at least one shutter opening aligns with the at least one body opening and fluid can pass through the cap, and (iii) a third, closed and permanently locked position in which in which the at least one shutter opening aligns with the at least one wall and fluid cannot pass through the cap, and the cap is further configured to not be moved to an open position.

2. The cap of claim 1, wherein the top portion comprises (a) outer threads configured to mate with threads of a fluid dispensing device, and (b) a top surface with an annular groove configured to retain debris, wherein the annular groove at least partially surrounds the opening.

3. The cap of claim 2, wherein the body further includes a first, annular rim on the top surface and outside of the annular groove, and a second, annular rim on the top surface around the opening, wherein each of the first, annular rim and the second, annular rim extend upwards from the top surface and are configured to seat against a surface of the fluid dispensing device when the cap is connected to the fluid dispensing device.

4. The cap of claim 1, wherein the cavity includes threads configured to connect to threads of a fluid sample container.

5. The cap of claim 4, wherein the cavity further includes a reduced-diameter portion that does not include the threads and the reduced-diameter portion includes at least one pair of positioning protrusions that defines a space between them, wherein the space is configured to receive an extension on the shutter in order to position the cap and shutter in the first, closed position when the two are connected.

6. The cap of claim 5, wherein the cavity includes two pairs of positioning protrusions and each pair defines a space between them, wherein each space is configured to receive an extension on the shutter in order to position the cap and shutter in the first, closed position when the two are connected.

7. The cap of claim 5, wherein the reduced-diameter portion further includes at least one abutment protrusion configured to (a) permit a stop on the shutter to move past it in a first direction, and (b) not permit the stop on the shutter move past it in a second direction.

8. The cap of claim 7, wherein the reduced-diameter portion includes two abutment protrusions and the shutter includes two stops.

9. The cap of claim 5, wherein the body further includes a plurality of tactile protrusions in the reduced-diameter portion, wherein each of the plurality of tactile protrusions are configured to provide a bump feel and/or a click sound when a stop or extension on the shutter moves past it.

10. The cap of claim 1, wherein the body further includes an extension in the cavity and the extension includes a first prong having a barb, and a second prong having a barb, wherein the first prong is spaced apart from the second prong, and each of the first prong and the second prong is formed at an outwardly-extending angle.

11. The cap of claim 1, wherein the shutter has an outer edge and a plurality of retention structures on the outer edge, wherein each retention structure comprises an extension configured to fit into a space between a pair of positioning protrusions in the cavity in order to position the cap in the first, closed position when the body and the shutter are connected, and wherein each of the plurality of retention structures has a first, non-compressed position and a second, compressed position.

12. The cap of claim 1, wherein the shutter has an outer edge and a plurality of connection structures, wherein each of the plurality of retention structures has a stop, and each stop is configured to move past an abutment protrusion in the cavity when moving in a first direction and is configured to not move past the abutment protrusion when moved in a second direction.

13. The cap of claim 1, wherein the shutter comprises at least one shutter opening that leads to a passage, wherein the shutter opening is in communication with the top opening.

14. The cap of claim 13, wherein the shutter further comprises two shutter openings in fluid communication with the passage, wherein the two shutter openings are configured to be positioned so as to (a) permit fluid to pass through, and into the cavity when the cap is in the second, open position, and (b) not permit fluid to pass through when the cap is in its first, closed position or its third, closed and permanently locked position.

15. The cap of claim 14, wherein the two shutter openings have exterior rims that are configured to seal against a wall of the body extension when the cap is in its (a) first, closed position, or (b) third, closed and permanently locked position.

16. The cap of claim 15, wherein the exterior rims comprise a softer material than the material that forms the two shutter openings.

17. The cap of claim 14, wherein the body has an extension in the cavity, wherein the extension comprises two extension openings and two walls, and wherein the two shutter openings of the shutter align with (a) the two extension openings of the extension when the cap is in the second, open position in order to permit the passage of fluid therethrough, and (b) the two walls of the extension when the cap is in its first, closed position or its third, closed and permanently locked position in order to prevent the passage of fluid therethrough.

18. The cap of claim 1, wherein the shutter further comprises at least one flange that extends at least partially through an extension opening and that is configured to contact a static structure on the fluid dispensing device and cause the shutter to remain stationary as the body is rotated.

19. The cap of claim 18, wherein the shutter includes two flanges and one flange extends through a first body opening and a second flange that extends through a second body opening that further comprises a fluid-dispenser connector, wherein the fluid-dispenser connector includes: (a) threads configured to mate with the outer threads on the body, (b) a first flange stop configured to contact one of the flanges when the cap is being tightened in order to prevent further rotation of the shutter and cause the cap to move from its first, closed position to its second, open position as the cap is turned and tightened onto the connector, and (c) a second flange stop configured to contact one of the flanges and prevent further rotation of the shutter and cause the cap to move from its second, open position to its third, closed and permanently locked position as the cap is turned and loosened and removed from the connector.

20. The cap of claim 1, wherein the shutter has an outer, top periphery having an interior periphery and an exterior periphery and the interior periphery comprises a softer materials than the material that forms the remainder of the exterior periphery, in order to form a seal between the shutter and an upper, annular surface of the body.

* * * * *